(12) United States Patent
Settleman et al.

(10) Patent No.: US 10,933,058 B2
(45) Date of Patent: Mar. 2, 2021

(54) COMBINATION THERAPY FOR THE TREATMENT OF PANCREATIC CANCER

(71) Applicant: Genentech, Inc., South San Francisco, CA (US)

(72) Inventors: Jeff Settleman, South San Francisco, CA (US); Nisebita Sahu, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 16/283,203

(22) Filed: Feb. 22, 2019

(65) Prior Publication Data
US 2019/0175576 A1    Jun. 13, 2019

Related U.S. Application Data

(63) Continuation of application No. PCT/US2017/047985, filed on Aug. 22, 2017.

(60) Provisional application No. 62/378,322, filed on Aug. 23, 2016.

(51) Int. Cl.
| | |
|---|---|
| *A61K 31/4523* | (2006.01) |
| *A61K 31/519* | (2006.01) |
| *A61P 35/00* | (2006.01) |
| *A61K 31/166* | (2006.01) |
| *A61K 31/18* | (2006.01) |
| *A61K 31/4184* | (2006.01) |
| *A61K 31/44* | (2006.01) |
| *A61K 45/06* | (2006.01) |
| *A61K 31/5025* | (2006.01) |
| *A61K 31/437* | (2006.01) |

(52) U.S. Cl.
CPC ........ *A61K 31/4523* (2013.01); *A61K 31/166* (2013.01); *A61K 31/18* (2013.01); *A61K 31/4184* (2013.01); *A61K 31/437* (2013.01); *A61K 31/44* (2013.01); *A61K 31/5025* (2013.01); *A61K 31/519* (2013.01); *A61K 45/06* (2013.01); *A61P 35/00* (2018.01)

(58) Field of Classification Search
CPC .... A61K 31/4523; A61K 31/519; A61P 35/00
See application file for complete search history.

(56) References Cited

FOREIGN PATENT DOCUMENTS

| | | | |
|---|---|---|---|
| WO | WO 2016/130917 A1 | 8/2016 | |
| WO | WO-2016123054 A2 * | 8/2016 | ............. A61K 45/06 |
| WO | WO-2016130917 A1 * | 8/2016 | ........... C07D 471/04 |

OTHER PUBLICATIONS

Anonymous, "Mutant p53 Promotes Pancreatic Cancer Metastasis via PDGFRβ Upregulation," Cancer Discovery, 4(6):4 pages, (2014).

Chang et al., "Antitumour activity of a potent MEK inhibitor RDEA119/ BAY 869766 combined with rapamycin in human orthotopic primary pancreatic cancer xenografts," BMC Cancer, 10(1):515, 11 pages, (2010).

Juntilla et al., "Modeling Targeted Inhibition of MEK and PI3 Kinase in Human Pancreatic Cancer," Mol Cancer Ther, 14(1):40-47, (2015).

Manchado et al., "A combinatorial strategy for treating KRAS-mutant lung cancer," Nature, 534(7609):647-651 and Extended Data, (2016).

Sahu et al., "Cotargeting of MEK and PDGFR/STAT3 Pathways to Treat Pancreatic Ductal Adenocarcinoma," Mol Cancer Ther, 16(9):1729-1738, (2017).

Zhao et al., "Rational combination of MEK inhibitor and the STAT3 pathway modulator for the therapy in K-Ras mutated pancreatic and colon cancer cells," Oncotarget, 6(16):14472-14487, (2015).

WIPO Application No. PCT/US2017/047985, PCT International Search Report and Written Opinion of the International Searching Authority dated Nov. 7, 2017.

Baines et al., "Inhibition of Ras for cancer treatment: the search continues," Future Medicinal Chemistry, 3(14):1787-1808, (2011).

Biankin et al., "Pancreatic cancer genomes reveal aberrations in axon guidance pathway genes," Nature, 491(7424):399-405, (2012).

Bronte et al., "Understanding local macrophage phenotypes in disease: modulating macrophage function to treat cancer," Nature Medicine, 21(2):117-119, (2015).

Chen et al., "Distribution and clinical significance of TAMs in pancreatic ductal adenocarcinoma: a retrospective analysis in China," Curr. Oncol., 22(1):e11-9, (2015).

Cid-Arregui et al., "Perspectives in the treatment of pancreatic adenocarcinoma," World Journal of Gastroenterology, 21(31):9297-9316, (2015).

Corcoran et al., "STAT3 Plays a Critical Role in KRAS-Induced Pancreatic Tumorigenesis," Cancer Research, 71(14):5020-5029, (2011).

Corcoran et al., "Synthetic lethal interaction of combined BCL-XL and MEK inhibition promotes tumor regressions in KRAS mutant cancer models," Cancer Cell, 23(1):121-128, (2013).

(Continued)

*Primary Examiner* — Yong L Chu
(74) *Attorney, Agent, or Firm* — Alston & Bird LLP

(57) ABSTRACT

The subject matter described herein is directed to compositions comprising a MEK inhibitor, or a pharmaceutically acceptable salt thereof, and a multi-kinase inhibitor that targets PDGFRα, S6 and STAT3 or a pharmaceutically acceptable salt thereof, and their use in treating pancreatic cancer. In another aspect, disclosed herein are methods of treating pancreatic cancer by administering a MEK inhibitor, or a pharmaceutically acceptable salt thereof, and a multi-kinase inhibitor, or a pharmaceutically acceptable salt thereof. In another aspect, the combination of cobimetinib, or a pharmaceutically acceptable salt thereof, and ponatinib or a pharmaceutically acceptable salt thereof is administered in a composition or the combination is administered separately to treat pancreatic cancer.

16 Claims, 36 Drawing Sheets
Specification includes a Sequence Listing.

(56) References Cited

OTHER PUBLICATIONS

Corcoran et al., "TORC1 suppression predicts responsiveness to RAF and MEK inhibition in BRAF-mutant melanoma," Science Translational Medicine, 5(196):196ra98, 13 pages, (2013).
Dai et al., "STAT3 mediates resistance to MEK inhibitor through microRNA miR-17," Cancer Research, 71(10):3658-3668, (2011).
Deng et al., "S1PR1-STAT3 signaling is crucial for myeloid cell colonization at future metastatic sites," Cancer Cell, 21(5):642-654, (2012).
Di Caro et al., "Dual prognostic significance of tumour-associated macrophages in human pancreatic adenocarcinoma treated or untreated with chemotherapy," Gut, 65:1710-1720, (2016).
Drake, C. G., "Combination immunotherapy approaches," Annals of Oncology, 23(Suppl 8): viii41-viii46, (2012).
Duncan et al., "Dynamic reprogramming of the kinome in response to targeted MEK inhibition in triple-negative breast cancer," Cell, 149(2):307-321, (2012).
Hidalgo, Manuel, "Pancreatic cancer," The New England Journal of Medicine, 362(17):1605-1617, (2010).
Inman et al., "Complex role for the immune system in initiation and progression of pancreatic cancer," World Journal of Gastroenterology, 20(32):11160-11181, (2014).
Jones et al., "Core signaling pathways in human pancreatic cancers revealed by global genomic analyses," Science, 321(5897):1801-1806, (2008).
Korc, Murray, "Pancreatic cancer-associated stroma production," American Journal of Surgery, 194(Suppl to Oct. 2007):S84-S86, (2007).
Lee et al., "Drug resistance via feedback activation of Stat3 in oncogene-addicted cancer cells," Cancer Cell, 26(2):207-221, (2014).
Lesina et al., "Stat3/Socs3 activation by IL-6 transsignaling promotes progression of pancreatic intraepithelial neoplasia and development of pancreatic cancer," Cancer Cell, 19(4):456-469, (2011).
McCubrey et al., "Ras/Raf/MEK/ERK and PI3K/PTEN/Akt/mTOR cascade inhibitors: how mutations can result in therapy resistance and how to overcome resistance," Oncotarget, 3(10):1068-1111, (2012).
Melero et al., "Therapeutic vaccines for cancer: an overview of clinical trials," Nature Reviews Clinical Oncology, 11(9):509-524, (2014).
Moses et al., "Pro-inflammatory cytokine release by peripheral blood mononuclear cells from patients with advanced pancreatic cancer: relationship to acute phase response and survival," Oncology Reports, 21(4):1091-1095, (2009).
Noy et al., "Tumor-associated macrophages: from mechanisms to therapy," Immunity, 41(1):49-61, (2014).
Silvestris et al., "Target therapies in pancreatic carcinoma," Current Medicinal Chemistry, 21(8):948-965, (2014).
Tjomsland et al., "The desmoplastic stroma plays an essential role in the accumulation and modulation of infiltrated immune cells in pancreatic adenocarcinoma," Clinical & Developmental Immunology, 2011:212810, 12 pages, (2011).
Tuveson et al., "Understanding metastasis in pancreatic cancer: a call for new clinical approaches," Cell, 148(1-2):21-23, (2012).
Vaccaro et al., "Metastatic pancreatic cancer: Is there a light at the end of the tunnel?", World Journal of Gastroenterology, 21(16):4788-4801, (2015).
Vonderheide et al., "Inflammatory networks and immune surveillance of pancreatic carcinoma," Current Opinion in Immunology, 25(2):200-205, (2013).
Weden et al., "Long-term follow-up of patients with resected pancreatic cancer following vaccination against mutant K-ras," International Journal of Cancer, 128(5):1120-1128, (2011).
Weissmueller et al., "Mutant p53 drives pancreatic cancer metastasis through cell-autonomous PDGF receptor beta signaling," Cell, 157(2):382-394, (2014).
Wormann et al., "The immune network in pancreatic cancer development and progression," Oncogene, 33(23):2956-2967, (2014).
Yen et al., "Myofibroblasts are responsible for the desmoplastic reaction surrounding human pancreatic carcinomas," Surgery, 131(2):129-134, (2002).
European Application No. 17761408.8, Article 94(3) Communication dated Jan. 28, 2020.

* cited by examiner

SEQUENCE LISTING

<160> NUMBER OF SEQ ID NOS: 1

<210> SEQ ID NO 1
<211> LENGTH: 21
<212> TYPE: DNA
<213> ORGANISM: artificial
<220> FEATURE:
<223> OTHER INFORMATION: Synthetic

<400> SEQUENCE: 1
aatcttagca ggaaggtgcc t                    21

COMBINATION THERAPY FOR THE TREATMENT OF PANCREATIC CANCER

CROSS-REFERENCE TO RELATED APPLICATIONS

This application is a continuation of International Application No. PCT/US2017/047985, filed on Aug. 22, 2017, which claims the benefit of priority to U.S. provisional Application No. 62/378,322 filed Aug. 23, 2016, each of which is herein incorporated by reference in its entirety for all purposes.

FIELD OF THE INVENTION

The subject matter described herein relates to the treatment of pancreatic cancer with a combination of a MEK inhibitor and a multi-target agent that targets RTKs, S6 and JAK/STAT.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 526149SEQLIST.TXT, created on Feb. 22, 2019, and having a size 521 bytes and is filed concurrently with the specification. The sequence listing contained in this ASCII formatted document is part of the specification and is herein incorporated by reference in its entirety.

BACKGROUND

Pancreatic ductal adenocarcinoma (PDAC) is one of the most malignant cancers, and numerous therapeutic approaches have been explored based on drug response findings from pancreatic cancer cells tested in culture models. The majority of PDAC tumors are driven by KRAS mutation-driven activation of MAPK signaling (Jones S, Zhang X, Parsons D W, Lin J C, Leary R J, Angenendt P, Core signaling pathways in human pancreatic cancers revealed by global genomic analyses, *Science,* 2008; 321 (5897):1801-6, Epub 2008/09/06; Biankin A V, Waddell N, Kassahn K S, Gingras M C, Muthuswamy L B, Johns A L, Pancreatic cancer genomes reveal aberrations in axon guidance pathway genes, *Nature,* 2012; 491(7424):399-405, Epub 2012/10/30; Cid-Arregui A, Juarez V, Perspectives in the treatment of pancreatic adenocarcinoma, *World Journal of Gastroenterology,* 2015; 21(31):9297-316, Epub 2015/08/27), thereby highlighting MEK as an important candidate target for therapeutic intervention in PDAC patients. However, pre-clinical and clinical studies have largely revealed a lack of efficacy upon MAPK pathway inhibition alone, potentially due to the rapid development of resistance to MAPK inhibitors through various compensatory mechanisms, thereby limiting the efficacy of the inhibitors and leading to emergence of drug resistant tumors. (Baines A T, Xu D, Der C J, Inhibition of Ras for cancer treatment: the search continues, *Future Medicinal Chemistry,* 2011; 3(14): 1787-808, Epub 2011/10/19; McCubrey J A, Steelman L S, Chappell W H, Abrams S L, Franklin R A, Montalto G, Ras/Raf/MEK/ERK and PI3K/PTEN/Akt/mTOR cascade inhibitors: how mutations can result in therapy resistance and how to overcome resistance, *Oncotarget,* 2012; 3(10): 1068-111, Epub 2012/10/23; Junttila M R, Devasthali V, Cheng J H, Castillo J, Metcalfe C, Clermont A C, Modeling targeted inhibition of MEK and PI3 kinase in human pancreatic cancer, *Molecular Cancer Therapeutics,* 2015; 14(1): 40-7, Epub 2014/11/08).

An enhanced understanding of the underlying mechanisms of sensitivity and resistance to MEK inhibitors can identify inhibitors to use in combination with MEK inhibitors that are effective for targeting pancreatic cancer cells.

BRIEF SUMMARY

In one aspect, the subject matter described herein is directed to a method of treating pancreatic cancer, in a subject in need thereof, comprising: administering to said subject a therapeutically effective amount of a combination of active agents, wherein said combination comprises a MEK inhibitor and a multi-kinase agent that targets PDGFRα, S6 and STAT3.

In another aspect, the subject matter described herein is directed to a combination of a) a MEK inhibitor, or a pharmaceutically acceptable salt thereof, and b) a multi-kinase inhibitor that targets PDGFRα, S6 and STAT3 or a pharmaceutically acceptable salt thereof for the treatment of pancreatic cancer.

In another aspect, the subject matter described herein is directed to a pharmaceutical composition comprising an effective amount of a combination of a MEK inhibitor or a pharmaceutically acceptable salt thereof and a multi-kinase agent that targets PDGFRα, S6 and STAT3, or a pharmaceutically acceptable salt thereof, and a pharmaceutically acceptable excipient, wherein said composition is for the treatment of pancreatic cancer In another aspect, the subject matter described herein is directed to a kit for treating pancreatic cancer, comprising: a) a MEK inhibitor or a pharmaceutically acceptable salt thereof and a multi-kinase inhibitor that targets PDGFRα, S6 and STAT3, or a pharmaceutically acceptable salt thereof; and b) a package insert or label indicating a treatment for pancreatic cancer.

These and other aspects are fully described below.

BRIEF DESCRIPTION OF THE DRAWINGS

(FIG. 6A) Immunoblot validating activation of PDGFRα, S6 and STAT3 upon cobimetinib treatment in KP4 cells. (FIG. 6B) Validation of the p-STAT3 increase upon cobimetinib treatment in PDAC cell lines and KPP GEMM-derived cell lines by western blot.

(FIG. 20A) Tumor growth curves (mean±S.E.M) of KP4 xenograft models treated every 24 hrs with cobimetinib (5 mg/kg, PO, QD) and/or ponatinib (30 mg/kg, PO, QD) (n=10 for each cohort); (FIG. 20B) Tumor growth curves (mean±S.E.M) of KPP xenograft models treated as in (FIG. 20A).

Figure 1:
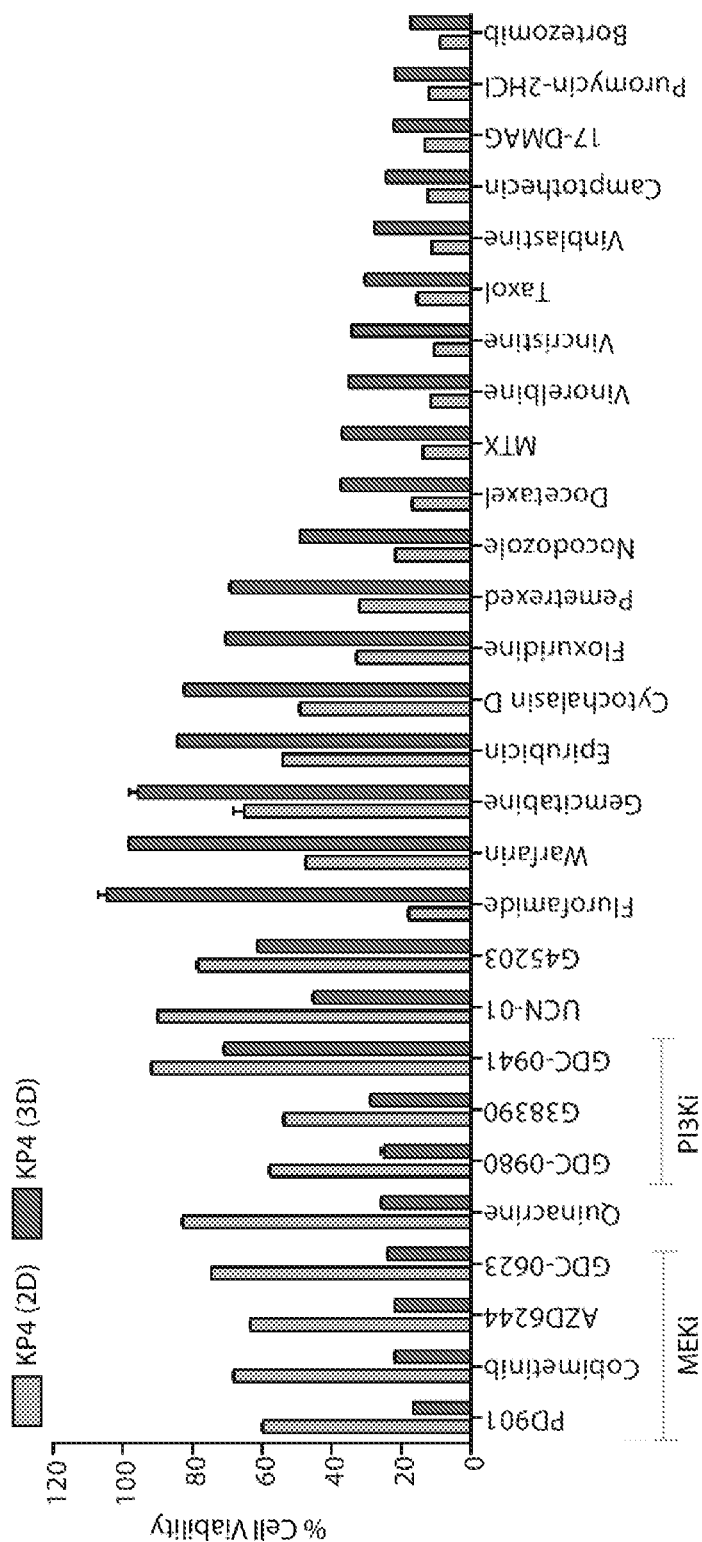
FIG. 1 depicts differential response to MEK inhibition by KP4 PDAC cells in 2D monolayer and 3D spheroid cultures: Small molecule inhibitor screen of KP4 cancer cells in 2D and 3D cultures.

The Data in FIGS. 6-23 are represented as mean±S.E.M. *P<0.05, Student's t-test.

DETAILED DESCRIPTION

Pancreatic ductal adenocarcinoma (PDAC) is among the most lethal human diseases and remains largely refractory to available drug treatments. The KRAS-driven MEK pathway is mutationally activated in most pancreatic cancers and is an important target for therapeutics. However, insufficient targeting of the known oncogenic drivers and activation of compensatory feedback loops and inability to prevent metastatic spread contribute to poor prognosis for this disease.

Activation of transmembrane receptor tyrosine kinases (RTKs) leads to numerous biochemical cascades that culminate in regulation of cell fate. This activation is regulated by molecules in the extracellular environment, primarily growth factors, extracellular matrix (ECM) proteins and adhesion molecules presented on the surface of neighboring cells. A cellular response to these signals occurs when the molecules bind to specific receptors present at the surface of the cell. Many growth factors (GFs) bind and activate transmembrane glycoproteins of the receptor tyrosine kinase (RTK) family.

RTKs contain an extracellular ligand binding domain, a single transmembrane domain, and an intracellular component that contains a tyrosine kinase domain and several regulatory tyrosines. RTKs can phosphorylate and activate cytoplasmic STAT-family transcription factors. These activated STATs translocate to the nucleus. Once inside the nucleus, STATs elevate transcription of genes involved in cell proliferation.

Platelet-derived growth factor receptors (PDGFR) are cell surface tyrosine kinase receptors for members of the platelet-derived growth factor (PDGF) family. PDGFRα and PDGFRβ isoforms are factors that regulate cell proliferation, cellular differentiation, cell growth and development. Upon binding, two isoforms dimerize to activate kinase activity and phosphorylation of the PDGFR. Tyrosine phosphorylation sites in growth factor receptors control the level of activity of the kinase and are binding sites for downstream signal transduction, which in many cases also are substrates for the kinase. This signaling cascade, which includes downstream signaling molecules such as S6 ribosomal protein, is implicated in many diseases, including cancer.

As described herein, using a 2-dimensional monolayer culture system as well as 3-dimensional spheroid culture system, it has been found that combination treatment with a MEK inhibitor or a pharmaceutically acceptable salt thereof and a multi-target agent that targets PDGFRα, S6 and STAT3, or a pharmaceutically acceptable salt thereof was effective in targeting pancreatic cancer cells both in monolayer and spheroids. Without being bound to theory, the combination can effectively block signaling via the PDGFRα and MEK kinases, while also preventing the activation of STAT3- and S6-mediated compensatory feedback loops in cancer cells. Furthermore, as set forth herein, using xenograft models, it has been found that co-treatment with a MEK inhibitor and ponatinib causes tumor regression and simultaneously inhibits myeloid populations that foster PDAC tumor progression by targeting tumor-associated macrophages in the pancreatic tumor microenvironment, thereby promoting tumor regression via dual mechanisms. PDAC patient samples revealed increased STAT3 activation in tumors and Erk activation in liver metastases, implicating STAT3 and Erk as critical drivers in PDAC tumors and liver metastases, respectively. As set forth herein, these results show a combination drug treatment strategy for effective treatment of pancreatic cancer. Additionally, the active agents when administered alone may not show efficacy towards pancreatic cancer.

While survival pathways identified as PDGFRβ, MEK, S6 and STAT3 are reportedly involved in tumorigenesis and metastasis in various cancer models (Lesina M, Kurkowski M U, Ludes K, Rose-John S, Treiber M, Kloppel G, Stat3/Socs3 activation by IL-6 transsignaling promotes progression of pancreatic intraepithelial neoplasia and development of pancreatic cancer, *Cancer Cell*, 2011; 19(4):456-69, Epub 2011/04/13; Yen T W, Aardal N P, Bronner M P, Thorning D R, Savard C E, Lee S P, Myofibroblasts are responsible for the desmoplastic reaction surrounding human pancreatic carcinomas, *Surgery*, 2002; 131(2):129-34, Epub 2002/02/21; Weissmueller S, Manchado E, Saborowski M, Morris J Pt, Wagenblast E, Davis C A, et al. Mutant p53 drives pancreatic cancer metastasis through cell-autonomous PDGF receptor beta signaling, *Cell*, 2014; 157(2):382-94, Epub 2014/04/15; Corcoran R B, Rothenberg S M, Hata A N, Faber A C, Piris A, Nazarian R M, TORC1 suppression predicts responsiveness to RAF and MEK inhibition in BRAF-mutant melanoma, *Science Translational Medicine*, 2013; 5(196):196ra98, Epub 2013/08/02; Corcoran R B, Cheng K A, Hata A N, Faber A C, Ebi H, Coffee E M, Synthetic lethal interaction of combined BCL-XL and MEK inhibition promotes tumor regressions in KRAS mutant cancer models, *Cancer Cell*, 2013; 23(1):121-8, Epub 2012/12/19; Deng J, Liu Y, Lee H, Herrmann A, Zhang W, Zhang C, S1PR1-STAT3 signaling is crucial for myeloid cell colonization at future metastatic sites, *Cancer Cell*, 2012; 21(5): 642-54, Epub 2012/05/26; Corcoran R B, Contino G, Deshpande V, Tzatsos A, Conrad C, Benes C H, STAT3 plays a critical role in KRAS-induced pancreatic tumorigenesis, *Cancer Research*, 2011; 71(14):5020-9, Epub 2011/05/19), it has now been found that MEK inhibition in primary pancreatic tumors triggers the activation of alternate signaling pathways through PDGFRα, S6 and STAT3, which contribute to resistance to single agent MEK inhibition. In particular, it has been shown that individual agents that showed no effect on cell viability individually, when combined inhibit cell growth in both 2D and 3D cultures. Accordingly, inhibition of PDGFRα, S6 and STAT3 activation in combination with MEK inhibition prevented the induction of resistance to the MEK inhibitor cobimetinib or a pharmaceutically acceptable salt thereof in pancreatic tumors. In an embodiment, treatment with the multi-RTK and JAK2 inhibitor ponatinib or a pharmaceutically acceptable salt thereof in combination with cobimetinib or a pharmaceutically acceptable salt thereof was highly effective in targeting pancreatic tumors, which as noted above, are generally refractory to drug treatment regimens currently being explored in the clinic.

Pancreatic ductal carcinoma (PDAC) is associated with a notable involvement of various stromal elements that contribute to aggressive tumor growth, metastasis, immune suppression, and drug resistance. (Cid-Arregui A, et al., (2015); Hidalgo M. Pancreatic cancer, *The New England Journal of Medicine*, 2010; 362(17):1605-17, Epub 2010/04/30; Korc M. Pancreatic cancer-associated stroma production, *American Journal of Surgery*, 2007; 194(4 Suppl):S84-6, Epub 2007/12/06; Inman K S, Francis A A, Murray N R. Complex role for the immune system in initiation and progression of pancreatic cancer, *World Journal of Gastroenterology*, 2014; 20(32):11160-81, Epub 2014/08/30; Wormann S M, Diakopoulos K N, Lesina M, Algul H, The immune network in pancreatic cancer development and progression, *Oncogene*, 2014; 33(23):2956-67, Epub 2013/

07/16; Moses A G, Maingay J, Sangster K, Fearon K C, Ross J A, Pro-inflammatory cytokine release by peripheral blood mononuclear cells from patients with advanced pancreatic cancer: relationship to acute phase response and survival, *Oncology Reports,* 2009; 21(4):1091-5, Epub 2009/03/17; Tjomsland V, Niklasson L, Sandstrom P, Borch K, Druid H, Bratthall C, The desmoplastic stroma plays an essential role in the accumulation and modulation of infiltrated immune cells in pancreatic adenocarcinoma, *Clinical & Developmental Immunology,* 2011; 2011:212810, Epub 2011/12/23; Silvestris N, Gnoni A, Brunetti A E, Vincenti L, Santini D, Tonini G, et al. Target therapies in pancreatic carcinoma, *Current Medicinal Chemistry,* 2014; 21(8):948-65, Epub 2013/09/03; Vaccaro V, Sperduti I, Vari S, Bria E, Melisi D, Garufi C, Metastatic pancreatic cancer: Is there a light at the end of the tunnel? *World Journal of Gastroenterology,* 2015; 21(16):4788-801. Epub 2015/05/07; Tuveson D A, Neoptolemos J P, Understanding metastasis in pancreatic cancer: a call for new clinical approaches, *Cell,* 2012; 148(1-2):21-3, Epub 2012/01/24). Tumor-associated macrophages are one of the most prevalent stromal cell types that infiltrate the pancreatic tumors and correlate with poor outcome in patients. (Vonderheide R H, Bayne L J, Inflammatory networks and immune surveillance of pancreatic carcinoma, *Current Opinion in Immunology,* 2013; 25(2):200-5, Epub 2013/02/21; Di Caro G, Cortese N, Castino G F, Grizzi F, Gavazzi F, Ridolfi C, Dual prognostic significance of tumour-associated macrophages in human pancreatic adenocarcinoma treated or untreated with chemotherapy, *Gut,* 2015. Epub 2015/07/15; Chen S J, Zhang Q B, Zeng L J, Lian G D, Li J J, Qian C C, Distribution and clinical significance of tumour-associated macrophages in pancreatic ductal adenocarcinoma: a retrospective analysis in China, *Curr. Oncol.* 2015; 22(1): e11-9, Epub 2015/02/17). Recent studies further suggest an important role for TAMs in tumor progression as well as metastasis. (Noy R, Pollard J W. Tumor-associated macrophages: from mechanisms to therapy, *Immunity,* 2014; 41(1):49-61, Epub 2014/07/19; Melero I, Gaudernack G, Gerritsen W, Huber C, Parmiani G, Scholl S, Therapeutic vaccines for cancer: an overview of clinical trials, *Nature Reviews Clinical Oncology,* 2014; 11(9):509-24, Epub 2014/07/09; Drake C G. Combination immunotherapy approaches, *Annals of oncology: official journal of the European Society for Medical Oncology/ESMO,* 2012; 23 Suppl 8:viii41-6, Epub 2012/08/29; Weden S, Klemp M, Gladhaug I P, Moller M, Eriksen J A, Gaudernack G, Long-term follow-up of patients with resected pancreatic cancer following vaccination against mutant K-ras, *International Journal of Cancer, Journal International du Cancer,* 2011; 128(5):1120-8, Epub 2010/05/18; Bronte V, Murray P J. Understanding local macrophage phenotypes in disease: modulating macrophage function to treat cancer, *Nature Medicine,* 2015; 21(2):117-9, Epub 2015/02/06). Our findings implicate the role of STAT3 signaling axis in both tumor cells and TAMs in PDAC in response to MEK inhibition. Our results further suggest that a MEK inhibitor, e.g., cobimetinib/multikinase inhibitor that targets PDGFRα, S6 and STAT3, e.g., ponatinib, co-treatment can target both myeloid and cancer cells within the primary tumor, causing increased cell death and tumor regression.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

The term "pancreatic cancer" refers to a neoplasm that originates in the pancreas. Pancreatic cancer includes exocrine and endocrine cancers. Most pancreatic cancers are exocrine tumors. Pancreatic endocrine tumors are also called islet cell tumors. Unfortunately, currently the prognosis for pancreatic cancer is poor even when detected early. Pancreatic cancers that can be treated with methods described herein include, but are not limited to, exocrine pancreatic cancers and endocrine pancreatic cancers. Exocrine pancreatic cancers include, but are not limited to, adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In some embodiments, the exocrine pancreatic cancer is pancreatic ductal carcinoma. Endocrine pancreatic cancers include, but are not limited to, insulinomas and glucagonomas.

In some embodiments, the pancreatic cancer is any of early stage pancreatic cancer, non-metastatic pancreatic cancer, primary pancreatic cancer, resected pancreatic cancer, advanced pancreatic cancer, locally advanced pancreatic cancer, metastatic pancreatic cancer, unresectable pancreatic cancer, pancreatic cancer in remission, recurrent pancreatic cancer, pancreatic cancer in an adjuvant setting, or pancreatic cancer in a neoadjuvant setting. In some embodiments, the pancreatic cancer is locally advanced pancreatic cancer, unresectable pancreatic cancer, or metastatic pancreatic ductal carcinoma. In some embodiments, the pancreatic cancer is resistant to gemcitabine-based therapy. In some embodiments, the pancreatic cancer is refractory to gemcitabine-based therapy.

The methods described herein can be used for any one or more of the following purposes: alleviating one or more symptoms of pancreatic cancer, delaying progression of pancreatic cancer, shrinking pancreatic cancer tumor size, disrupting (such as destroying) pancreatic cancer stroma, inhibiting pancreatic cancer tumor growth, prolonging overall survival, prolonging disease-free survival, prolonging time to pancreatic cancer disease progression, preventing or delaying pancreatic cancer tumor metastasis, reducing (such as eradiating) preexisting pancreatic cancer tumor metastasis, reducing incidence or burden of preexisting pancreatic cancer tumor metastasis, preventing recurrence of pancreatic cancer, and/or improving clinical benefit of a patient with pancreatic cancer.

The pancreatic cancer treatment method described herein involves administering a therapeutically effective amount of a combination of a MEK inhibitor or a pharmaceutically acceptable salt thereof and a multi-kinase inhibitor that targets PDGFRα, S6 and STAT3 or a pharmaceutically acceptable salt thereof to a subject (human or animal) in need of it in order to inhibit, slow or reverse the growth, development or spread of pancreatic cancer, including primary tumor(s) and metastatic tumor(s). Such administration constitutes a method for the treatment or prophylaxis of diseases mediated by one or more kinases and or survival pathways inhibited by one of the administered active agents. "Administration" or "administering" of a compound as disclosed herein encompasses the delivery to a recipient of active agents, or prodrugs or other pharmaceutically acceptable derivatives thereof, using any suitable formulation or route of administration, as discussed herein. The MEK inhibitor and the multi-kinase inhibitor can be administered consecutively, sequentially, or a combination of both, in either order.

The term "subject" refers to animals such as mammals, including, but not limited to, primates (e.g., humans), cows, sheep, goats, horses, dogs, cats, rabbits, rats, mice and the like. In certain embodiments, the subject is a human.

The term "prophylaxis" or "prophylactic" refers to the continued absence of symptoms of the disease or condition that would be expected had the combination not been administered.

The term "synergistic" as used herein refers to a therapeutic combination which is more effective than the additive effects of the two or more single agents. A determination of a synergistic interaction between a MEK inhibitor and a multi-kinase inhibitor that targets PDGFRα, S6 and STAT3 can be based on the results obtained from the assays described herein. For example, the in vivo or in vitro methods disclosed herein. The results of these assays can be analyzed using the Chou and Talalay combination method and Dose-Effect Analysis with CalcuSyn software in order to obtain a Combination Index (Chou and Talalay, 1984, *Adv. Enzyme Regul.* 22:27-55). The combinations provided can be evaluated in one or more assay systems, and the data can be analyzed utilizing a standard program for quantifying synergism, additivism, and antagonism among anticancer agents. An example program is that described by Chou and Talalay, in *New Avenues in Developmental Cancer Chemotherapy*, Academic Press, 1987, Chapter 2. Combination Index values less than 0.8 indicate synergy, values greater than 1.2 indicate antagonism and values between 0.8 to 1.2 indicate additive effects. The combination therapy may provide "synergy" and prove "synergistic", i.e., the effect achieved when the active agents used together is greater than the sum of the effects that results from using the compounds separately. A synergistic effect may be attained when the active agents are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active agent is administered sequentially, i.e., serially, whereas in combination therapy, effective dosages of two or more active agents are administered together. Combination effects can be evaluated using both the BLISS independence model and the highest single agent (HSA) model (Lehar et al., *Molecular Systems Biology*, 3:80 (2007)). BLISS scores quantify degree of potentiation from single agents and a positive BLISS score (greater than 0) suggests greater than simple additivity. A cumulative positive BLISS score greater than 250 is considered strong synergy observed within the concentration ranges tested. An HSA score (greater than 0) suggests a combination effect greater than the maximum of the single agent responses at corresponding concentrations.

A "spheroid" refers to a cell culture as it is known in the art as a three-dimensional (3D) cell culture in an artificial environment in which biological cells grow or interact with their surroundings in all three dimensions. Unlike 2D environments, e.g. a petri dish, a 3D cell culture allows cells in vitro to grow in all directions, similar to how they would grow in vivo. The artificial environment contains a media that provides certain nutrients and other factors that allow the cells to grow. The media described herein provides an environment for rapid cell culture. The term "rapid" refers to a time period that is less than that required for the same cell expansion in a comparative media.

The term "contact" or "contacting" refers to allowing the active agent to be within close enough proximity to the target the enzyme or survival pathway such that the active agent is able to bind to and inhibit, diminish or reduce the activity of the target.

As used herein the term "mammal" refers to humans as well as all other mammalian animals. As used herein, the term "mammal" includes a "subject" or "patient" and refers to a warm blooded animal. It is understood that guinea pigs, dogs, cats, rats, mice, horses, goats, cattle, sheep, zoo animals, livestock, primates, and humans are all examples of animals within the scope of the meaning of the term.

As used herein "a mammal in need thereof" is a subject whom has been diagnosed as suffering from the specific condition intended to be treated, e.g., pancreatic cancer or a specific type of pancreatic cancer.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

Use of the word "inhibitor" herein is meant to mean a molecule that inhibits activity of the target enzyme. By "inhibit" herein is meant to decrease the activity of the target enzyme, as compared to the activity of that enzyme in the absence of the inhibitor. In some embodiments, the term "inhibit" means a decrease in MEK activity or a decrease of a specific survival pathway of the cancer cell, of at least about 5%, at least about 10%, at least about 20%, at least about 25%, at least about 50%, at least about 60%, at least about 70%, at least about 80%, at least about 90%, or at least about 95%. In other embodiments, inhibit means a decrease of activity of about 5% to about 25%, about 25% to about 50%, about 50% to about 75%, or about 75% to 100%. In some embodiments, inhibit means a decrease of activity of about 95% to 100%, e.g., a decrease in activity of 95%, 96%, 97%, 98%, 99%, or 100%. Such decreases can be measured using a variety of techniques that would be recognizable by one of skill in the art, including in vitro kinase assays.

As used herein, a "MEK inhibitor" is a molecule that reduces, inhibits, or otherwise diminishes one or more of the biological activities of MEK (MEK1 and/or MEK2). The activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of MEK compared to an appropriate control.

As used herein, a "multi-kinase inhibitor" is a molecule that reduces, inhibits, or otherwise diminishes the biological activities of PDGFRα, S6 and STAT3. Suitable multi-kinase inhibitors show activity against each of these three targets, and may have activity against additional targets. For example, in embodiments, a multi-kinase inhibitor additionally acts on tumor associated macrophages associated with a pancreatic tumor. The ability of the multi-kinase inhibitor to act on each of these targets when in combination with a MEK inhibitor provides excellent efficacy against pancreatic cancer. The activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of the targets as compared to an appropriate control.

The presently disclosed compounds may or may not be a specific inhibitor. By "specific inhibitor" is intended an agent that reduces, inhibits, or otherwise diminishes the activity of a defined target greater than that of an unrelated target. For example, a MEK specific antagonist reduces at least one biological activity of MEK by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. A specific MEK inhibitor reduces the biological activity of one or more family members of MEK by an amount that is statistically greater than the inhibitory effect of the antagonist on any other protein (e.g., other serine/threonine kinases). In some of these embodiments, the $IC_{50}$ of the MEK inhibitor for a RAF is about 90%, 80%, 70%, 60%, 50%, 40%, 30%, 20%, 10%, 0.1%, 0.01%, 0.001%, or less of the $IC_{50}$ of the MEK inhibitor for another serine/threonine kinase, other MEK family member or other type of kinase (e.g., tyrosine kinase).

The term "targets" or "target" refers to the ability of the active agent to act on a specific towards a specific MEK enzyme or a specific enzyme associated with a survival pathway. The ability of an active agent to target an enzyme can be determined through routine experimentation as described herein or using other known methods.

As used herein, a "survival pathway" refers to a cancer cell's adaptive mechanism or ability to promote their survival and proliferation and become resistant to an active agent. As used herein, the survival pathways are associated with PDGFRα, S6 and STAT3.

The phrase "therapeutically effective amount" means an amount of an active agent that (i) treats or prevents pancreatic cancer, (ii) attenuates, ameliorates, or eliminates one or more symptoms of pancreatic cancer, or (iii) prevents or delays the onset of one or more symptoms of pancreatic cancer. The therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith. The phrase "pharmaceutically acceptable salt," as used herein, refers to pharmaceutically acceptable organic or inorganic salts of a molecule. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion. Examples include, but are not limited to, the fumarate salt or hemifumarate salt of cobimetinib and ponatinib HCl.

Additional definitions are provided below as appropriate.

II. In Vivo Methods

The presently disclosed combinations of a MEK inhibitor and a multi-kinase inhibitor that targets PDGFRα, S6 and STAT3 are useful in treating pancreatic cancer.

In embodiments disclosed herein is a method of treating pancreatic cancer, in a subject in need thereof, comprising: administering to said subject a therapeutically effective amount of a combination of active agents, wherein said combination comprises a MEK inhibitor or a pharmaceutically acceptable salt thereof and a multi-kinase agent that targets PDGFRα, S6 and STAT3 or a pharmaceutically acceptable salt thereof. This embodiment can further comprise inhibiting the proliferation of tumor associated macrophages.

Examples of MEK inhibitors that may be used include cobimetinib, GDC-0623, trametinib, binimetinib, selumetinib, pimasertinib, refametinib, PD-0325901 and BI-847325, or a pharmaceutically acceptable salt thereof. In an embodiment, the MEK inhibitor is cobimetinib or a pharmaceutically acceptable salt thereof. Cobimetinib has the following structure:

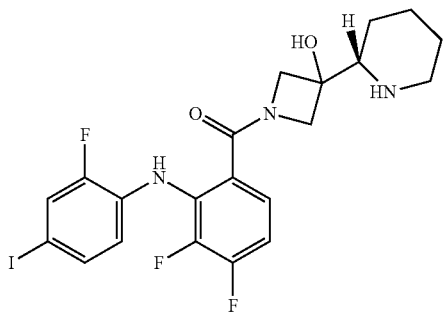 [SMILES: O=C(c1ccc(F)c(F)c1Nc1ccc(I)cc1F)N1CC(O)([C@@H]2CCCCN2)C1]

Cobimetinib is sold as Cotellic® and is found in the commercial formulation as the hemifumarate salt.

A useful multi-kinase agent that target PDGFRα, S6 and STAT3 is ponatinib. Ponatinib has the following structure:

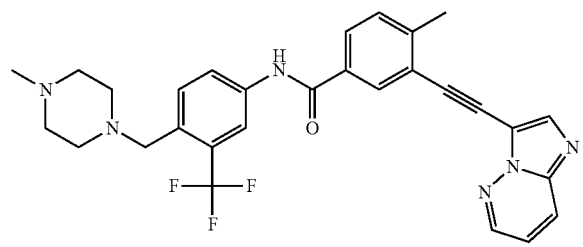 [SMILES: Cc1ccc(C(=O)Nc2ccc(CN3CCN(C)CC3)c(C(F)(F)F)c2)cc1C#Cc1cnc2cccnn12]

Ponatinib is sold as Iclusig® and is found in the commercial formulation as the hydrochloride salt.

Pancreatic cancers include endocrine and exocrine cancers. In embodiments, the pancreatic cancer is selected from the group consisting of adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas. In an embodiment, the pancreatic cancer is pancreatic ductal adenocarcinoma.

In embodiments, the MEK inhibitor or a pharmaceutically acceptable salt thereof and the multi-kinase inhibitor that targets PDGFRα, S6 and STAT3 or a pharmaceutically acceptable salt thereof are synergistic. That is, the combination provides a level of efficacy that is greater than the additive effect of both agents. In embodiments, one or both of the active agents alone does not show desired efficacy against pancreatic cancer. In the example of cobimetinib or a pharmaceutically acceptable salt thereof and ponatinib or a pharmaceutically acceptable salt thereof, neither agent alone is known to be effective against pancreatic cancer.

In embodiments, the MEK inhibitor or a pharmaceutically acceptable salt thereof and said multi-kinase inhibitor or a pharmaceutically acceptable salt thereof are administered as a combined formulation. In embodiments, the combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities The methods of treating pancreatic cancer reduce, inhibit, or otherwise diminish the activity of one or more target enzymes or survival pathways. Tumor associated macrophages associated with a pancreatic tumor can also be targeted. Any method known in the art to measure the MEK activity or the level of PDGFRα, S6, STAT3 and tumor associated macrophage activation may be used to determine the activity of the combination, including in vitro kinase assays, immunoblots with antibodies specific for phosphorylated targets, or the measurement of a downstream biological effect of activity.

The pancreatic cancer can be at early stage or at late stage and may have also metastasized. The combinations described herein can be used to treat cancers at any stage, including cancers that have metastasized.

Treatment of a subject with an effective amount of a combination MEK inhibitor and a multi-kinase inhibitor that targets PDGFRα, S6 and STAT3 can include a single treatment or can include a series of treatments.

Useful amounts of the active agents are as described elsewhere herein. In particular embodiments, the MEK inhibitor is administered in an amount of from about 5 mg to about 100 mg, or from about 45 mg to about 75 mg, and the multi-kinase inhibitor is administered in an amount of from about 5 mg to about 100 mg, or from about 30 mg to about 60 mg. In embodiments, the MEK inhibitor is administered in an amount of about 60 mg, and the multi-kinase inhibitor is administered in an amount of about 45 mg. In embodiments, the administration of the combination therapy is once daily oral administration. In embodiments, it is preferred that the MEK inhibitor is cobimetinib or a pharmaceutically acceptable salt thereof and the multi-kinase inhibitor is ponatinib or a pharmaceutically acceptable salt thereof. In some embodiments, each active agent is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 30 mg/kg, 40 mg/kg, 50 mg/kg, 100 mg/kg, and 200 mg/kg. The amount of each active agent present in the combination composition to be administered can be from about 1 mg to about 1000 mg, or from about 5 mg to about 100 mg, or from about 10 mg to about 80 mg, or from about 45 mg to about 75 mg, or from about 30 mg to about 60 mg. It is understood that appropriate doses of the active compound depends upon a number of factors within the knowledge of the ordinarily skilled physician or veterinarian. The dose(s) of the active agent will vary, for example, depending upon the age, body weight, general health, gender, and diet of the subject, the time of administration, the route of administration, the rate of excretion, and any drug combination. It will also be appreciated that the effective dosage used for treatment may increase or decrease over the course of a particular treatment. Changes in dosage may result and become apparent from the results of diagnostic assays.

In some embodiments, described herein is a method for treating a pancreatic cancer in a subject in need thereof comprising administering to the subject a therapeutically effective amount of a combination MEK inhibitor or a pharmaceutically acceptable salt thereof and multi-kinase inhibitor that targets PDGFRα, S6 and STAT3 or a pharmaceutically acceptable salt thereof, further comprising administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of an anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation.

In some embodiments, the treatment results in a sustained response in the subject after cessation of the treatment. "Sustained response" refers to the sustained effect on reducing tumor growth after cessation of a treatment. For example, the tumor size may remain the same or smaller as compared to the size at the beginning of the administration phase. In some embodiments, the sustained response has a duration at least the same as the treatment duration, at least 1.5×, 2.0×, 2.5×, or 3.0× length of the treatment duration.

The treatment methods disclosed herein may result in a partial or complete response. As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started. As used herein, "overall response rate" (ORR) refers to the sum of complete response (CR) rate and partial response (PR) rate.

The treatment methods disclosed herein can lead to an increase in progression free survival and overall survival of the subject administered the combination therapy. As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" refers to the percentage of subjects in a group who are likely to be alive after a particular duration of time.

In some embodiments, the subject that is administered the combination is a mammal, such as domesticated animals (e.g., cows, sheep, cats, dogs, and horses), primates (e.g., humans and non-human primates such as monkeys), rabbits, and rodents (e.g., mice and rats). In some embodiments, the subject treated is a human.

The subject in need of treatment for pancreatic cancer may be a person demonstrating symptoms of cancer, one that has been diagnosed with cancer, a subject that is in remission from pancreatic cancer, or a subject having an increased risk for developing cancer (e.g., a genetic predisposition, certain dietary or environmental exposures).

Many combinations described herein will be determined to be synergistic.

The in vitro methods described herein use a method of preparing a spheroid cell culture comprising culturing the cells in a media containing serum that has been boiled prior to adding to the culture media for said culturing. It has been found that a media can be modified to culture 3-D spheroids in a rapid manner. The modified media is prepared by boiling the fetal bovine serum (FBS) prior to its contact with the cells to be cultured. In embodiments, the FBS has been boiled at 95-100° C. for 10 minutes at which point the color of the serum turns yellow. The boiled FBS is then centrifuged at 8000×g for 20 minutes and filtered through sterile Corning vacuum filter unit with filter pore size of 0.22 µm. Useful media comprise from about 5% to about 20% (v/v) fetal bovine serum. The media for spheroid culture is prepared by adding 10% (v/v) of boiled FBS to RPMI media supplemented with 2 mM L-glutamine, 100 units ml$^{-1}$ of penicillin and streptomycin. The spheroid culture media needs to be freshly prepared prior to using it. The boiled FBS can be stored at 4° C. for 2-3 months. The media for monolayer culture is prepared by adding 10% (v/v) of normal FBS to RPMI media supplemented with 2 mM L-glutamine, 100 units ml$^{-1}$ of penicillin and streptomycin. The media for migration assay is prepared by adding 20% (v/v) of normal FBS to RPMI media supplemented with 2 mM L-glutamine, 100 units ml$^{-1}$ of penicillin and streptomycin.

III. Combination Pharmaceutical Compositions

In embodiments, the subject matter described herein is directed to a combination of a) a MEK inhibitor or a pharmaceutically acceptable salt thereof, and b) a multi-kinase inhibitor that targets PDGFRα, S6 and STAT3 or a pharmaceutically acceptable salt thereof for the prophylactic or therapeutic treatment of pancreatic cancer.

In embodiments, the subject matter described herein is directed to a pharmaceutical composition comprising an effective amount of a combination of a MEK inhibitor or a pharmaceutically acceptable salt thereof, and a multi-kinase agent that targets PDGFRα, S6 and STAT3 or a pharmaceutically acceptable salt thereof, and a pharmaceutically acceptable excipient. In a particular embodiment, the pharmaceutical composition is for the treatment of pancreatic cancer.

In embodiments, the composition comprises a MEK inhibitor selected from the group consisting of cobimetinib, GDC-0623, trametinib, binimetinib, selumetinib, pimasertinib, refametinib, PD-0325901 and BI-847325, or a pharmaceutically acceptable salt thereof. In an embodiment, the MEK inhibitor is cobimetinib, or a pharmaceutically acceptable salt thereof. In a particular embodiment, the MEK inhibitor is cobimetinib hemifumarate.

In embodiments, the multi-kinase agent is ponatinib, or a pharmaceutically acceptable salt thereof. In an embodiment, the multi-kinase inhibitor is ponatinib hydrochloride.

In embodiments, the composition comprises cobimetinib or a pharmaceutically acceptable salt thereof and ponatinib or a pharmaceutically acceptable salt thereof. In embodiments, the composition comprises cobimetinib hemifumarate and ponatinib hydrochloride.

The amount of each active agent present in the combination can be from about 1 mg to about 1000 mg, or from about 5 mg to about 100 mg, or from about 10 mg to about 80 mg, or from about 45 mg to about 75 mg, or from about 30 mg to about 60 mg. In embodiments, the MEK inhibitor is present in an amount of from about 45 mg to about 75 mg and said multi-kinase inhibitor is present in an amount of from about 30 mg to about 60 mg.

The combination therapy may provide "synergy" and prove "synergistic", i.e., the effect achieved when the active agents used together is greater than the sum of the effects that results from using the active agents separately. A synergistic effect may be attained when the active agents are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the active agents are administered or delivered sequentially, e.g., by different injections in separate syringes, separate pills or capsules, or separate infusions. In general, during alternation therapy, an effective dosage of each active agent is administered sequentially, i.e., serially, whereas in combination therapy, effective dosages of two or more active agents are administered together.

MEK inhibitors and/or multi-kinase inhibitors, each are also referred to herein as an active agent, can be formulated in accordance with standard pharmaceutical practice as a pharmaceutical composition. An exemplary multi-kinase inhibitor, ponatinib is available as a tablet for oral administration in 15 mg, 30 mg and 45 mg strengths. An exemplary MEK inhibitor, cobimetinib is available as a tablet for oral administration in 20 mg strength. However, according to this aspect, there is provided other pharmaceutical compositions comprising a MEK inhibitor or a multi-kinase inhibitor or both in association with a pharmaceutically acceptable excipient, such as a carrier or diluent.

A typical formulation is prepared by mixing an active agent and one or more excipients. Suitable excipients are well known to those skilled in the art and include materials such as carbohydrates, waxes, water soluble and/or swellable polymers, hydrophilic or hydrophobic materials, gelatin, oils, solvents, water and the like. The particular excipients used will depend upon the means and purpose for which the active agent is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the active agent or aid in the manufacturing of the pharmaceutical product (i.e., medicament). The formulations may be prepared using conventional dissolution and mixing procedures.

For example, the bulk drug substance (i.e., active agent or stabilized form of the active agent (e.g., complex with a cyclodextrin derivative or other known complexation agent) is dissolved in a suitable solvent in the presence of one or more of the excipients described above. The active agent is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. In one embodiment, the container is a blister pack.

Pharmaceutical formulations may be prepared for various routes and types of administration. For example, an active agent having the desired degree of purity may optionally be mixed with pharmaceutically acceptable excipients (*Remington's Pharmaceutical Sciences* (1980) 16$^{th}$ edition, Osol, A. Ed., Mack Publishing Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The active agent can be sterile. In particular, formulations to be used for in vivo administration must be sterile. Such sterilization is readily accomplished by filtration through sterile filtration membranes.

The active agent ordinarily can be stored as a solid composition, a lyophilized formulation or as an aqueous solution.

The pharmaceutical compositions comprising an active agent can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations. Acceptable excipients are nontoxic to recipients at the dosages and concentrations employed, and may include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polysorbates (e.g., TWEEN™), poloxamers (e.g., PLURONICS™) or polyethylene glycol (PEG). The active agents may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences*.

Sustained-release preparations of an active agent may be prepared. Suitable examples of sustained-release preparations include semipermeable matrices of solid hydrophobic polymers containing an active agent, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as injectable microspheres composed of lactic acid-glycolic acid copolymer and leuprolide acetate (LUPRON DEPOT™) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences*. Such methods include the step of bringing into association the active agent with the carrier which constitutes one or more accessory ingredients. In general the formulations are prepared by uniformly and intimately bringing into association the active agent(s) with liquid carriers or finely divided solid carriers or both, and then, if necessary, shaping the product.

Formulations of an active agent suitable for oral administration may be prepared as discrete units such as pills, capsules, cachets or tablets each containing a predetermined amount of an active agent.

Compressed tablets may be prepared by compressing in a suitable machine the active agent in a free-flowing form such as a powder or granules, optionally mixed with a binder, lubricant, inert diluent, preservative, surface active or dispersing agent. Molded tablets may be made by molding in a suitable machine a mixture of the powdered active agent moistened with an inert liquid diluent. The tablets may optionally be coated or scored and optionally are formulated so as to provide slow or controlled release of the active agent therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of active agents intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active agent in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Aqueous suspensions of an active agent contain the agent in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of an active agent(s) may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active agent that may be combined with the carrier material to produce a single dosage form will vary depending upon the host treated and the particular mode of administration. For example, a time-release formulation intended for oral administration to humans may contain approximately 1 to 1000 mg of active agent compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active agent per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active agent. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active agent such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active agent.

The subject matter further provides veterinary compositions comprising at least one active agent as above defined together with a veterinary carrier therefore. Veterinary carriers are materials useful for the purpose of administering the composition and may be solid, liquid or gaseous materials which are otherwise inert or acceptable in the veterinary art and are compatible with the active agent(s). These veterinary compositions may be administered parenterally, orally or by any other desired route.

IV. Articles of Manufacture

In another aspect, described herein are articles of manufacture, for example, a "kit" containing materials useful for the treatment of pancreatic cancer. The kit comprises a container comprising a combination of a MEK inhibitor or a pharmaceutically acceptable salt thereof and a multi-kinase inhibitor that targets PDGFRα, S6 and STAT3 or a pharmaceutically acceptable salt thereof, for the treatment of pancreatic cancer. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a combination of a MEK inhibitor or a pharmaceutically acceptable salt thereof and a multi-kinase inhibitor or a pharmaceutically acceptable salt thereof or a formulation thereof which is effective for treating the condition and may have a sterile access port (for example, the container may be an intravenous solution bag or a vial having a stopper pierceable by a hypodermic injection needle). The label or package insert indicates that the composition is used for treating pancreatic cancer. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the MEK inhibitor or a pharmaceutically acceptable salt thereof and, if separately formulated, the multi-kinase inhibitor or a pharmaceutically acceptable salt thereof formulation. For example, if the kit comprises a first composition comprising a MEK inhibitor or a pharmaceutically acceptable salt thereof, and a second pharmaceutical formulation comprising a multi-kinase inhibitor or a pharmaceutically acceptable salt thereof, the kit may further comprise directions for the simultaneous, sequential or separate administration of the first and second pharmaceutical compositions to a patient in need thereof.

In another embodiment, the kits are suitable for the delivery of solid oral forms of the combination of MEK inhibitor or a pharmaceutically acceptable salt thereof and multi-kinase inhibitor or a pharmaceutically acceptable salt thereof. Such a kit preferably includes a number of unit dosages. Such kits can include a card having the dosages oriented in the order of their intended use. An example of such a kit is a "blister pack." Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a MEK inhibitor or a pharmaceutically acceptable salt thereof contained therein; and optionally (b) a second container with a multi-kinase inhibitor or a pharmaceutically acceptable salt thereof formulation contained therein. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of a MEK inhibitor or a pharmaceutically acceptable salt thereof and a multi-kinase inhibitor or a pharmaceutically acceptable salt thereof, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

In yet another embodiment, the subject matter described herein is directed to a media that uses serum that has been pre-boiled, i.e., boiled for a certain amount of time prior to its use in a culture media. The media provides rapid formation of spheroids as compared to media that uses normal serum which has not been boiled. In embodiments, the media for culturing cells comprising about 10% boiled fetal bovine serum, wherein said serum has been boiled for 10 minutes at 95-100° C. prior to adding it to culture media.

The subject matter described herein includes the following specific embodiments:
1. A method of treating pancreatic cancer, in a subject in need thereof, comprising: administering to said subject an effective amount of a combination of active agents, wherein said combination comprises a MEK inhibitor or a pharmaceutically acceptable salt thereof and a multi-kinase agent that targets PDGFRα, S6 and STAT3 or a pharmaceutically acceptable salt thereof.
2. The method of embodiment 1, wherein said MEK inhibitor is selected from the group consisting of cobimetinib, GDC-0623, trametinib, binimetinib, selumetinib, pimasertinib, refametinib, PD-0325901 and BI-847325, or a pharmaceutically acceptable salt thereof.
3. The method of any above embodiment, wherein said MEK inhibitor is selected from the group consisting of cobimetinib, and trametinib, or a pharmaceutically acceptable salt thereof.
4. The method of any above embodiment, wherein said MEK inhibitor is cobimetinib, or a pharmaceutically acceptable salt thereof.
5. The method of any above embodiment, wherein said multi-kinase agent is ponatinib or a pharmaceutically acceptable salt thereof.
6. The method of any above embodiment, wherein said pancreatic cancer is endocrine.
7. The method of any above embodiment, wherein said pancreatic cancer is exocrine.
8. The method of any above embodiment, wherein said pancreatic cancer is adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, and undifferentiated carcinomas.
9. The method of any above embodiment, wherein said pancreatic cancer is pancreatic ductal adenocarcinoma.
10. The method of any above embodiment, wherein said combination is synergistic.
11. The method of any above embodiment, wherein said active agents are administered sequentially.
12. The method of any above embodiment, wherein said active agents are administered concomitantly.
13. The method of any above embodiment, wherein said MEK inhibitor and said multi-kinase inhibitor are administered as a combined formulation.
14. The method of any above embodiment, wherein said MEK inhibitor is administered in an amount of from about 45 mg to about 75 mg and said multi-kinase inhibitor is administered in an amount of from about 30 mg to about 60 mg.
15. The method of any above embodiment, wherein said amounts are administered once daily.
16. The method of any above embodiment, wherein said MEK inhibitor is cobimetinib, or a pharmaceutically acceptable salt thereof, such as cobimetinib hemifumarate, and said multi-kinase inhibitor is ponatinib, or a pharmaceutically acceptable salt thereof, such as ponatinib HCl.
17. A combination of a) a MEK inhibitor or a pharmaceutically acceptable salt thereof, and b) a multi-kinase inhibitor that targets PDGFRα, S6 and STAT3 or a pharmaceutically acceptable salt thereof for the prophylactic or therapeutic treatment of pancreatic cancer.
18. A pharmaceutical composition comprising an effective amount of a combination of a MEK inhibitor, or a pharmaceutically acceptable salt thereof, and a multi-kinase agent, or a pharmaceutically acceptable salt thereof, that targets PDGFRα, S6 and STAT3, and a pharmaceutically acceptable excipient, wherein said composition is for the treatment of pancreatic cancer.
19. The composition of any above embodiment, wherein said MEK inhibitor is selected from the group consisting of cobimetinib, GDC-0623, trametinib, binimetinib, selumetinib, pimasertinib, refametinib, PD-0325901 and BI-847325, or a pharmaceutically acceptable salt thereof.
20. The composition of any above embodiment, wherein said MEK inhibitor is selected from the group consisting of cobimetinib, and trametinib, or a pharmaceutically acceptable salt thereof.
21. The composition of any above embodiment, wherein said MEK inhibitor is cobimetinib or a pharmaceutically acceptable salt thereof.
22. The composition of any above embodiment, wherein said multi-kinase agent is ponatinib or a pharmaceutically acceptable salt thereof.
23. The composition of any above embodiment, comprising cobimetinib, or a pharmaceutically acceptable salt thereof and ponatinib, or a pharmaceutically acceptable salt thereof.
24. The composition of any above embodiment, wherein said MEK inhibitor, or a pharmaceutically acceptable salt thereof, is present in an amount of from about 45 mg to about 75 mg and said multi-kinase inhibitor, or a pharmaceutically acceptable salt thereof, is present in an amount of from about 30 mg to about 60 mg.
25. A kit comprising a MEK inhibitor, or a pharmaceutically acceptable salt thereof, and a multi-kinase agent, or a pharmaceutically acceptable salt thereof, that targets PDGFRα, S6 and STAT3, a container, and a package insert or label.

The following examples are offered by way of illustration and not by way of limitation.

EXAMPLES

Materials and Methods

Cell Lines and Reagents:

All cell lines were from ATCC except for PA-TU-8988T cells, which were from DSMZ, and SUIT-2 cells, which were from JCRB. All cell lines were banked at the Genentech cell line core facility that routinely performs SNP and STR analysis to confirm cell line identity. All cell lines were routinely cultured in RPMI medium (Gibco) supplemented with 10% FBS, 2 mM L-glutamine, 100 units ml$^{-1}$ of penicillin and streptomycin. Rapamycin and ponatinib were from Selleckchem, crenolanib was from Arog Pharmaceuticals, and cobimetinib, GDC-0941 and GDC-0980 were synthesized at Genentech. The human phospho-kinase array kit was from R&D Systems (ARY003B), the Cignal-45-Pathway reporter array was from Qiagen (CCA-901L), the human tyrosine kinases RT$^2$ Profiler PCR array was from Qiagen (PAHS-161Z), and the MDSC isolation kit was from Miltenyi Biotec. All assays with these kits were performed according to manufacturer's instructions.

Western Blotting and Cell Viability Assays:

Cells were seeded in 10 cm dishes and treated with 1 μM of small molecule inhibitors for 24 hrs. Cell lysates were prepared in RIPA lysis buffer (Thermo Scientific) containing a protease inhibitor cocktail (Thermo Scientific), SDS-PAGE was performed and proteins were transferred to nitrocellulose membranes. Immunoblotting was performed using standard methods. Protein bands were quantified using ImageJ software. Primary antibodies: p-Erk, p-STAT3, p-S6, total-S6, p-PDGFRα, p-PDGFRβ, p-RSK3, cleaved PARP, Bcl-xL, Mcl, survivin, Rab11, p-Akt, β-Actin, GAPDH (Cell Signaling), total-STAT3, total-PDGFRα (Santa Cruz Biotechnology), p-EphA7 (Gene Tex) and p-EphA2/3, EphA2/5 (MyBioscource).

Cell viability assays were performed by treating cells with a dose titration (0.001 to 10 μM) or fixed dose (1 μM) of the various pharmacologic inhibitors for 72 hrs and measuring viability using CellTiter Glo (Promega). Bliss scores were calculated as described previously. (Borisy A A, Elliott P J, Hurst N W, Lee M S, Lehar J, Price E R, Systematic discovery of multicomponent therapeutics, *Proceedings of the National Academy of Sciences of the United States of America,* 2003; 100(13):7977-82, Epub 2003/06/12).

Lentiviral Infection:

Lentiviral particles for shSTAT3 were generated as described previously. (Moffat J, Grueneberg D A, Yang X, Kim S Y, Kloepfer A M, Hinkle G, A lentiviral RNAi library for human and mouse genes applied to an arrayed viral high-content screen, *Cell,* 2006; 124(6):1283-98. Epub 2006/03/28). shSTAT3 in a Dox-inducible system were obtained from LakePharma Inc. The target sequence used for shSTAT3 was AATCTTAGCAGGAAGGTGCCT. KP4 and MIA-PACA2 cells were transduced with optimized titers of lentiviruses and selected using 1 μg/ml puromycin.

Luminex Assay and ELISA:

Luminex assays on culture supernatants from cancer cells cultured for 72 hrs or plasma samples collected at end points from animal studies were performed using a multiplex kit (Bio-Rad) according to manufacturer's instructions. The PDGFα ELISA was performed using a kit from R&D Systems.

Invasion Assays:

Cells in RPMI containing 2% FBS were seeded on the inverted inserts of BD BioCoat Matrigel invasion chambers (BD Biosciences). The lower chambers were filled with RPMI supplemented with 10% FBS as chemoattractant and the number of cells that entered the bottom chamber after 18 hrs of incubation was measured using a SpectraMax M5 (Molecular Devices).

Animal Studies:

All animal studies were carried out in compliance with National Institutes of Health Guide for the Care and Use of Laboratory Animals. All dosing regimens were well tolerated in xenografts. Two xenograft models were used: the human PDAC-derived cell line KP4 and cells derived from tumors isolated from KPP GEMM mice. $5 \times 10^6$ cells were subcutaneously implanted into the right flanks of immune-deficient mice (Charles River Laboratories) without using any Matrigel. Mice were randomized after tumors reached ~200 mm³ and then treated with Vehicle (MCT+25 mM Citrate Buffer, pH 2.75), cobimetinib (5 mg/kg)+/− ponatinib (30 mg/kg), PO, QD. Tumor volumes were measured using Ultra-Cal IV calipers at the indicated intervals. To appropriately analyze the repeated measurement of tumor volumes from the same animals over time, a mixed modeling approach was used. (Jose Pinheiro D B, Saikat DebRoy, Deepayan Sarkar, R Core team. Linear and Nonlinear mixed effects models. Package 'nlme'2008). This approach addresses both repeated measurements and modest dropouts due to any non-treatment-related deaths of animals before the study end. Cubic regression splines were used to fit a non-linear profile to time courses of $\log_2$ tumor volume at each dose level. These non-linear profiles were then related to the dose within the mixed model. Tumor growth inhibition as a percentage of vehicle (% TGI) was calculated as the percentage of the area under the fitted curve (AUC) for the respective dose group per day in relation to the vehicle, using the following formula:

% $TGI = 100 \times (1 - AUC_{dose}/AUC_{veh})$.

To determine the uncertainty intervals (UIs) for % TGI, the fitted curve and the fitted covariance matrix were used to generate a random sample as an approximation to the distribution of % TGI. The random sample was composed of 1,000 simulated realizations of the fitted-mixed model, where the % TGI has been recalculated for each realization. The reported UIs were the values for which 95% of the time the recalculated values of % TGI would fall in this region given the fitted model. The 2.5 and 97.5 percentiles of the simulated distribution were used as the upper and lower UIs. Tumor growth inhibition >60% was considered meaningful. (Wong H, Choo E F, Alicke B, Ding X, La H, McNamara E, Antitumor activity of targeted and cytotoxic agents in murine subcutaneous tumor models correlates with clinical response, *Clinical Cancer Research: an official journal of the American Association for Cancer Research,* 2012; 18(14):3846-55. Epub 2012/06/01).

Plotting was performed and generated using R, version 2.8.1 (R Development Core Team 2008; R Foundation for Statistical Computing; Vienna, Austria) and Excel, version 12.0.1 (Microsoft Corporation). Data were analyzed using R, version 2.8.1, and the mixed models were fit within R using the nlme package, version 3.1-89 (41).

Immunohistochemistry and Immunofluorescence:

Immunohistochemistry and immunofluorescence were performed on 4 μm thick sections cut from formalin-fixed paraffin-embedded cell pellets, whole tissue sections, and TMA blocks (US Biomax, Inc.). Slides were deparaffinized and antigen unmasking was performed on PT Module (Thermo Scientific) with Target Retrieval Solution (Dako). Endogenous peroxidase activity was blocked with 3% $H_2O_2$ and 3% BSA was used for blocking endogenous immunoglobulins. Primary antibodies against p-Erk and p-STAT3 (Cell Signaling) were used at 1 μg/ml, p-PDGFRα (Cell Signaling) at 0.4 μg/ml, F4/80 (Serotec) at 10 μg/ml, Gr-1 (BD Pharmingen) at 1 μg/ml, cleaved caspase 3 (Cell Signaling) at 0.6 μg/ml and CD8α (Genentech) at 5 μg/ml. Antibody binding was detected using Vecstatin ABC Elite horseradish peroxidase (Vector Laboratories) or PowerVision Poly-HRP (Leica Biosystems) and metal-enhanced 3, 3'-diaminobenzidine (Pierce) for IHC stainings and PowerVision Poly-HRP (Leica Biosystems) along with TSA kits (Life Technologies) for immunofluorescence staining. Counterstaining of IHC slides was performed using Mayer's hematoxylin (Rowley Biochemical).

Histology:

Whole slide images were acquired with a Nanozoomer XR automated slide scanning platform (Hamamatsu, Hamamatsu City. Shizuoka Pref., Japan) at 200× final magnification.

Microarray and RNA Sequencing Analysis:

Gene expression in normal and PDAC human tissues was measured using Affymetrix HGU133P arrays by Gene Logic. Gene expression data were normalized by the robust multichip average (RMA) method. Expression probe set $203131_{at}$ was used for human PDGFRα, 202273_at, for human PDGFRβ, 205945_at, for human IL6-R, and 204171_at was used for PRS6KB1.

Statistical Analysis:

All data are represented as mean±standard error of the mean (S.E.M). A student t-test (two-tailed) was used to compare 2 groups and to calculate P-values using Prism or Excel. P <0.05 was considered significant. Survival curves were plotted using the Kaplan-Meier method.

Example 1: Sensitivity to MEK Inhibition in Pancreatic Cancer Cell Spheroid Cultures To compare how pancreatic cancer cells cultured in 2-dimensional (2D) and 3-dimensional (3D) cultures respond to various cancer therapeutic agents, we treated the KRAS mutant PDAC cancer cell line KP4 with a panel of 203 small molecule inhibitors of cancer-relevant targets and known chemotherapeutics (Table 1).

TABLE 1

| Small molecule inhibitors | |
|---|---|
| Small Molecule Inhibitor | Target |
| Allopurinol | Approved drug in oncology |
| Anastrozole | Approved drug in oncology |
| Bortezomib | Approved drug in oncology |
| Celecoxib | Approved drug in oncology |
| Chloroquine HCl | Approved drug in oncology |
| Dasatinib | Approved drug in oncology |
| Exemestane | Approved drug in oncology |
| Fulvestrant | Approved drug in oncology |
| Imatinib | Approved drug in oncology |
| Imiquimod | Approved drug in oncology |
| Lenalidomide | Approved drug in oncology |
| Meclorethamine | Approved drug in oncology |
| Methoxsalen | Approved drug in oncology |
| Mitotane | Approved drug in oncology |
| MTX | Approved drug in oncology |
| Taxol | Approved drug in oncology |
| Quinacrine | Approved drug in oncology |
| SAHA | Approved drug in oncology |
| Tamoxifen | Approved drug in oncology |
| Temozolomide | Approved drug in oncology |
| Teniposide, VM-26 | Approved drug in oncology |
| Toremifene | Approved drug in oncology |
| Vandetanib | Approved drug in oncology |
| Pamidronate | Approved drug in oncology |
| Zoledronate | Approved drug in oncology |
| Streptozocin | Approved drug in oncology |
| Goserelin acetate | Approved drug in oncology |
| Alprazolam | Approved drug in non-oncology |
| Calcipotriene | Approved drug in non-oncology |
| Darifenacin Hydrobromide | Approved drug in non-oncology |
| Digitoxin | Approved drug in non-oncology |
| Diltiazem HCL | Approved drug in non-oncology |
| Fenofibrate | Approved drug in non-oncology |
| Fluvastatin | Approved drug in non-oncology |
| Hydrocortisone | Approved drug in non-oncology |
| Ibandronate | Approved drug in non-oncology |
| Ibuprofen | Approved drug in non-oncology |
| Ramipril | Approved drug in non-oncology |
| Sisomicin | Approved drug in non-oncology |
| Sulindac | Approved drug in non-oncology |
| Sumatriptan Succinate | Approved drug in non-oncology |
| Telmisartan | Approved drug in non-oncology |
| Triamcinolone acetonide | Approved drug in non-oncology |
| Vardenafil | Approved drug in non-oncology |
| Warfarin | Approved drug in non-oncology |
| Metformin Hydrochloride | Approved drug in non-oncology |
| Diltiazem hydrochloride | Approved drug in non-oncology |
| Dexamethasone | Approved drug in non-oncology |
| SN-38 | DNA and RNA synthesis inhibitor |
| Altretamine | DNA damaging agent |
| Azacitidine | DNA damaging agent |
| Bleomycin | DNA damaging agent |
| Busulfan | DNA damaging agent |
| Camptothecin | DNA damaging agent |
| Capecitabine | DNA damaging agent |
| Carmustine | DNA damaging agent |
| Chlorambucil | DNA damaging agent |
| Cisplatin | DNA damaging agent |
| Cladribine | DNA damaging agent |
| Clofarabine | DNA damaging agent |

TABLE 1-continued

| Small molecule inhibitors | |
|---|---|
| Small Molecule Inhibitor | Target |
| Cyclophosphamide | DNA damaging agent |
| Cytarabine | DNA damaging agent |
| Dacarbazine | DNA damaging agent |
| Docetaxel | DNA damaging agent |
| Doxorubicin | DNA damaging agent |
| Epirubicin | DNA damaging agent |
| Floxuridine | DNA damaging agent |
| Fludarabine | DNA damaging agent |
| Fluorouracil-5-FU | DNA damaging agent |
| Gemcitabine | DNA damaging agent |
| Hydroxyurea | DNA damaging agent |
| Idarubicin | DNA damaging agent |
| Ifosfamide | DNA damaging agent |
| Irinotecan | DNA damaging agent |
| Lomustine | DNA damaging agent |
| Melphalan, L-PAM | DNA damaging agent |
| Mercaptopurine, 6-MP | DNA damaging agent |
| Mitomycin C | DNA damaging agent |
| Oxaliplatin | DNA damaging agent |
| Pemetrexed disodium | DNA damaging agent |
| Procarbazine | DNA damaging agent |
| Puromycin-2HCl | DNA damaging agent |
| Thalidomide | DNA damaging agent |
| Thioguanine, 6-TG | DNA damaging agent |
| Vinorelbine | DNA damaging agent |
| Etoposide phosphate | DNA damaging agent |
| Topotecan | DNA damaging agent |
| Actinomycin D | DNA damaging agent |
| Decitabine | DNA damaging agent |
| Pentostatin | DNA damaging agent |
| Vinblastine | DNA damaging agent |
| Vincristine | DNA damaging agent |
| Carboplatin | DNA damaging agent |
| NU7026 | DNA-PK inhibitor |
| Momentasone Furoate | Corticosteroid |
| AM114 | 20S proteasome inhibitor |
| MG132 | 26S proteasome inhibitor |
| Carvedilol | Beta blocker |
| Donepezil hydrochloride | Cholinesterase inhibitor |
| Desloratadine | Histamine H1-receptor antagonist |
| Bicalutamide | Nonsteroidal antiandrogen |
| Tadalafil | Phosphodiesterase inhibitor |
| Omeprazole | Proton pump inhibitor |
| Raloxifene | Estrogen receptor modulator |
| Sertraline HCl | Serotonin reuptake inhibitor |
| Atorvastatin, Calcium Salt | HMG-CoA reductase inhibitor. |
| Captopril | ACE inhibitor |
| Enalapril maleate-felodipine ER | ACE inhibitor |
| Akt inhibitor 1/2 | Akt inhibitor |
| GDC-0068 | Akt inhibitor |
| Tamsulosin, Hydrochloride | Alpha blocker |
| Irbesartan | Angiotensin II receptor blocker |
| Letrozole | Aromatase inhibitor |
| Rosuvastatin calcium | HMG-CoA reductase inhibitor |
| BAY 11-7082 | Inhibitor of cytokine induced IKB-alpha |
| Valsartan | Angiotensin II receptor antagonist |
| Bexarotene | Anti-neoplastic agent |
| Ezetimibe | Antihyperlipidemic agent |
| Ganciclovir | Antiviral for CMV infections |
| Ku55933 | ATM Inhibitor |
| VX680 | Aurora kinase Inhibitor |
| Sorafenib | Tyrosine Kinase inhibitor |
| Nilotinib | Bcr-Abl, c-Kit, PDGFR inhibitor |
| Cytochalasin D | Inhibits association and dissociation of actin subunits |
| Diazepam | Binds to GAGAa, agonist |
| PLX4032 | BRAF Inhibitor |
| PD166793 | MMP inhibitor |
| G45203 | c-Met inhibitor |
| Mibefradil dihydrochloride hydrate | $Ca^{2+}$ channel blocker |
| z-VAD-FMK | Caspase Inhibitor |
| RO-3306 | CDK1 Inhibitor |
| GW8510 | CDK2 inhibitor (also inhibits CDK5) |
| Flavopiridol | CDK2, CDK9 inhibitor |
| CHR265 | Chiron Raf inhibitor |

TABLE 1-continued

Small molecule inhibitors

| Small Molecule Inhibitor | Target |
| --- | --- |
| PD407824 | Chk1 and Wee1 inhibitor |
| Fluticasone Propionate | Corticosteroid |
| Tenidap | COX/5-LOX inhibitor |
| Zebularine | Cytidine deaminase inhibitor |
| Erlotinib | EGFR inhibitor |
| Gefitinib | EGFR inhibitor |
| Tunicamycin | ER stress inducer |
| Lapatinib | ERbB-2 and EGFR dual kinase inhibitor |
| PD173074 | FGFR inhibitor |
| Trichostatin A | HDAC inhibitor |
| 17-DMAG | Hsp90 inhibitor |
| Mevastatin | Hypolipidemic agent |
| IKK16 | IKK inhibitor |
| FK506 | Immunosuppressant |
| EeyrestatinI | Inhibitor of ERAD |
| FTI-277 | Inhibitor of H- and K-Ras farnesyltransferase |
| Thapsigargin | Inhibitor of SERCA |
| Forskolin | Inhibits adenylate cyclase |
| Roscovitine | Inhibits CDK1/CyclinB, CDK2, CDK5 |
| BML-259 | Inhibits cdk5, cdk2 |
| Folinic Acid | Inhibits DHFR, Enhances 5-FU. |
| Brefeldin A | Inhibits golgi transport |
| Lovostatin | Inhibits HMG-CoA reductase |
| U0126 | Inhibits MEK1 and MEK2 |
| Lonidamine | Inhibits mitochondrial hexokinase |
| S(−)(−)Blebbistatin | Inhibits nonmuscle myosin II ATPase |
| SB202190 | Inhibits p38 MAP kinases |
| Nocodozole | Inhibits polymerization of microtubules |
| PP1 | Inhibits Src fmaily of tyrosine kinases |
| Staurosporine | Kinase inhibitor |
| Nutlin-3 | MDM2 inhibitor |
| PD98059 | MEK/ERK inhibitor |
| GDC-0623 | MEK inhibitor |
| XL-518 | MEK inhibitor |
| AZD6244 | MEK inhibitor |
| PD901 | MEK inhibitor |
| Monastrol | Mitotic agent |
| Rapamycin | mTOR inhibitor |
| Solifenacin Hydrochloride | Muscarinic receptor antagonist |
| Pindolol | Non-specific beta-blocker |
| Vioxx | NSAID |
| (+)-Clopidogrel Hydrogen Sulfate | $P2Y_{12}$ receptor antagonist |
| 3-aminobenzamide | PARP Inhibitor |
| Sildenafil citrate | PDE inhibitor |
| GDC-0980 | PI3K inhibitor |
| G38390 | PI3K inhibitor |
| GDC-0464 | PI3Ki p110alpha-specific |
| GDC-0941 | PI3Ki pan-class I |
| H89 | PKA Inhibitor |
| UCN-01 | PKC inhibitor |
| Anagrelide HCl | PDE3 inhibitor |
| GDC-0879 | Raf inhibitor |
| Megestrol acetate | Progesterone derivative |
| Lactacystin | Proteasome Inhibitor |
| Esomeprazole magnesium | Proton pump inhibitor |
| Lansoprazole | Proton pump inhibitor |
| L-744,832 | Ras farnesyltransferase inhibitor |
| Sunitinib | RTK inhibitor |
| CGK733 | Selective inhibitor of ATR and ATM kinases |
| Chymostatin | Serine and cysteine protease inhibitor |
| Citalopram Oxalate | Serotonin reuptake inhibitor |
| Allocholic Acid | Steroid |
| Progesterone | Steroid |
| BAY 61-3606 | Syk inhibitor |
| Rosiglitazone maleate | Thiazolidinedione |
| Pioglitazone Hydrochloride | Thiazolidinedione |
| Tandutinib | Type III RTK inhibitor |
| Flurofamide | Urease inhibitor |

Figure 27A:
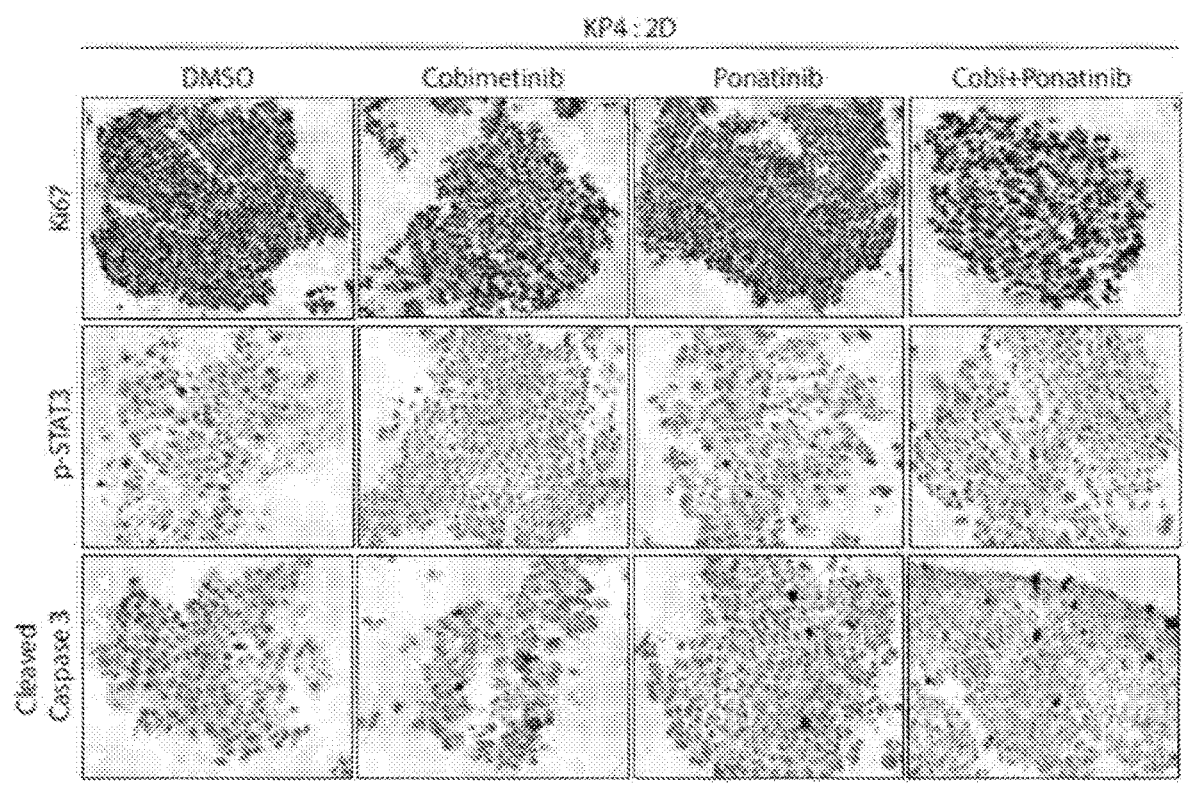
FIGS. 27A-B depict KP4-derived 3D spheroids with histopathological characteristics of micrometastases show differential sensitivity to small molecule inhibitors: KP4 cells were cultured in RPMI media containing 10% normal FBS (for 2D culture) or 10% pre-boiled FBS (for 3D culture) for 3 days and IHC was performed on 2D cell pellets or 3D spheroids for Ki67, p-STAT3 and cleaved caspase-3.
Figure 27B:
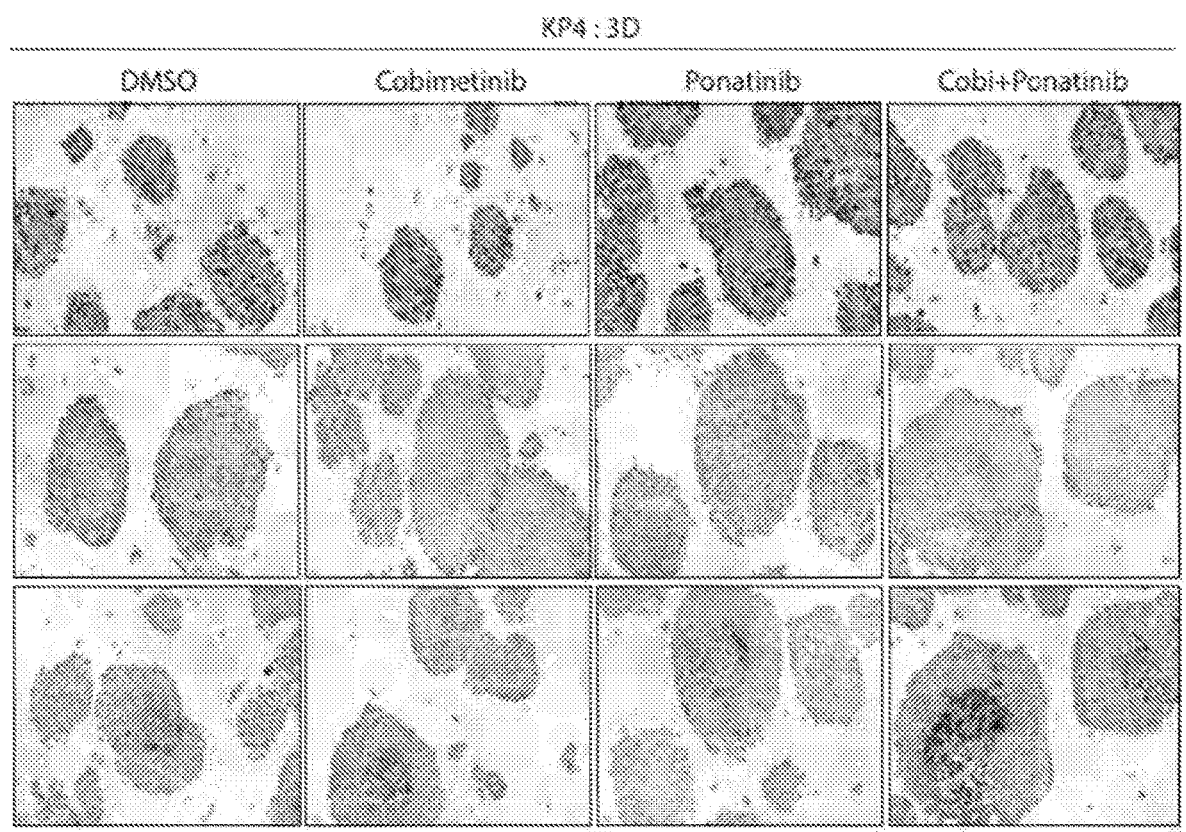
Figure 28:
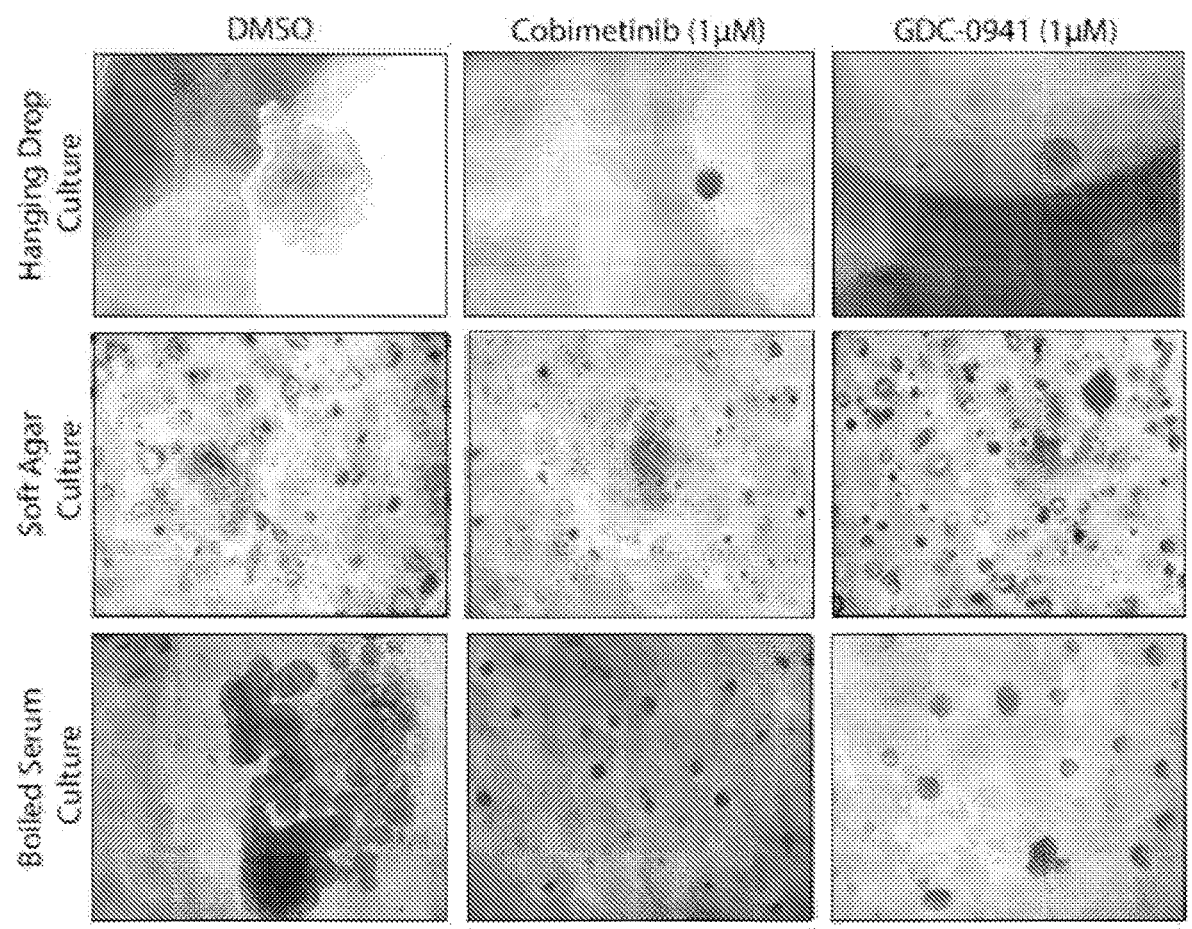
FIG. 28 depicts KP4-derived 3D spheroids with histopathological characteristics of micrometastases show differential sensitivity to small molecule inhibitors: Spheroids formed using 10% pre-boiled FBS show a similar drug sensitivity profile as seen with other conventional 3D culture methods.
Figure 29:
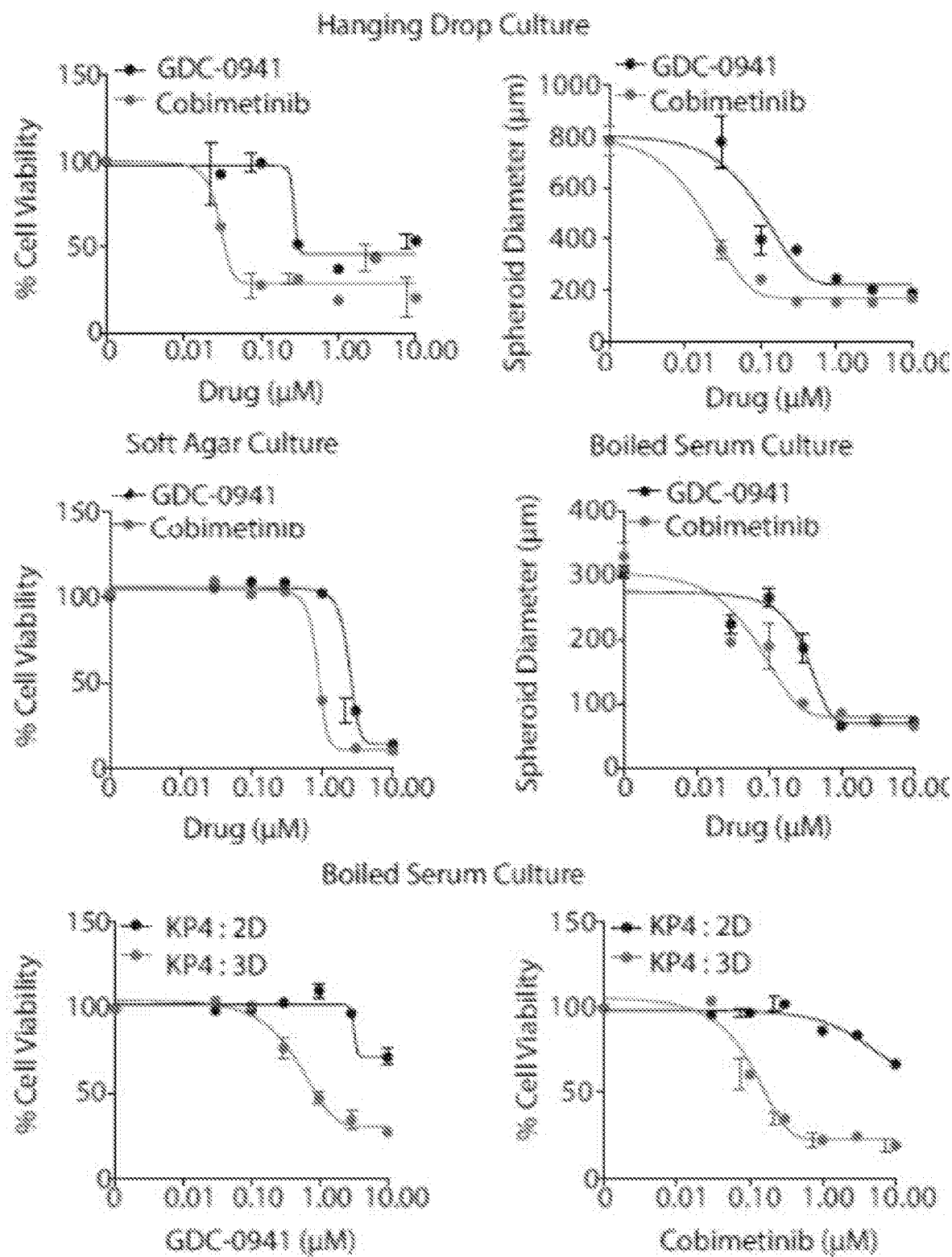
FIG. 29 depicts KP4-derived 3D spheroids with histopathological characteristics of micrometastases show differential sensitivity to small molecule inhibitors: Cell viability assay and colony count assay of spheroids formed from different 3D culture methods.
Figure 30:
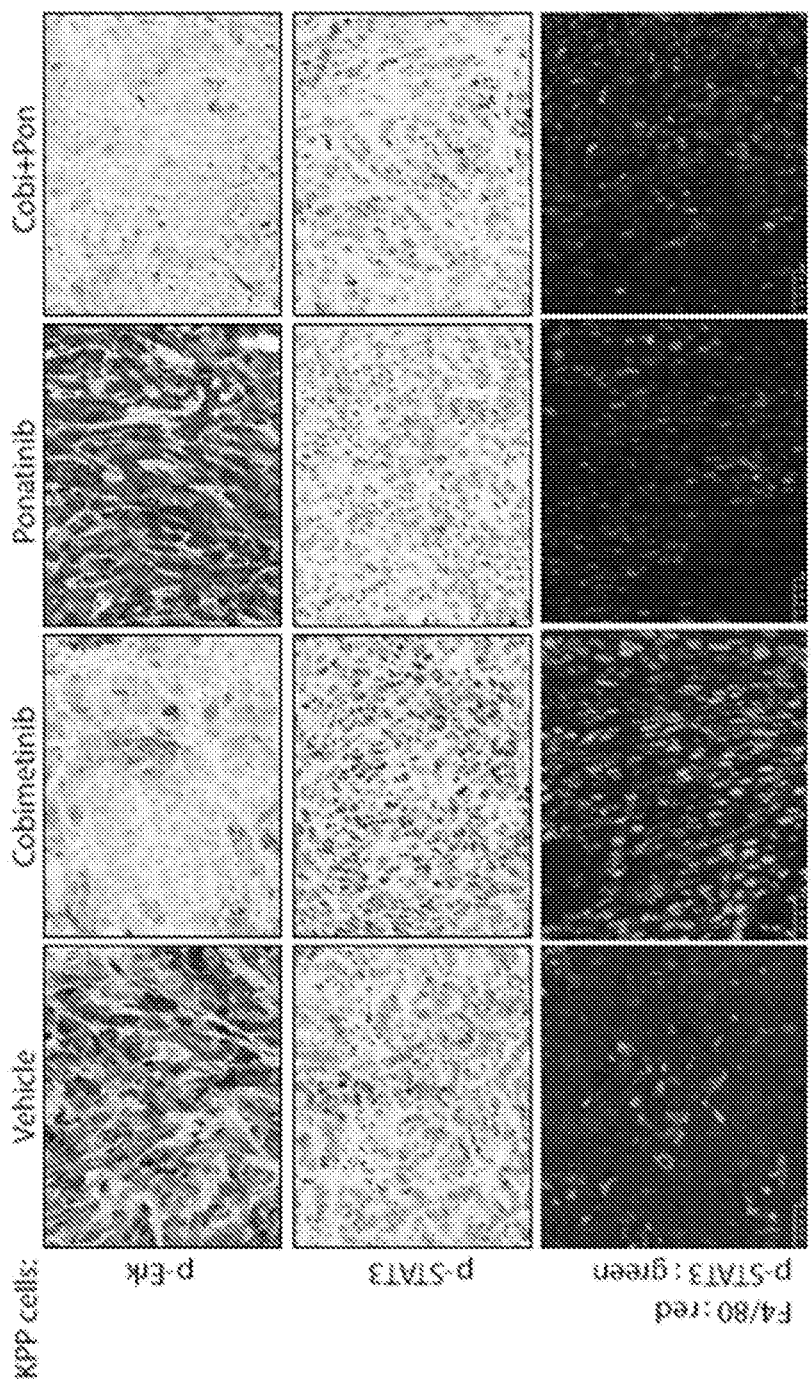
FIG. 30 depicts cobimetinib/ponatinib co-treatment impairs tumor growth and decreases tumor-associated macrophage infiltration: Representative tumor sections from KPP xenografts examined with p-Erk and p-STAT3 antibodies by IHC or co-stained with anti-p-STAT3 and anti-F4/80 by immunofluorescence. Scale bar: 20 μm for IHC slides, 50 μm for IF slides.

For 3D cultures, described herein is a method to facilitate a relatively rapid "high-throughput" analysis. It has been observed that culturing cancer cells in media containing 10% fetal bovine serum that had been pre-boiled for 10 minutes at 95-100° C. prior to adding it to culture media consistently led to the rapid formation of 3D "spheroids." The spheroids formed using this method displayed all the typical characteristics of previously described spheroids, including a low level of proliferation, with predominant localization of Ki67 staining in the outer peripheral layer, as well as necrotic/apoptotic centers with apoptosis marked by cleaved caspase-3 by 72 hrs (FIG. 27). Their drug sensitivity pattern was also similar to previously described spheroids (FIGS. 28 & 29).

Treatment of KP4 cells in 2D and 3D culture conditions with the panel of 203 compounds revealed differential sensitivity to several agents (FIG. 1). The 3D cultures are generally more resistant to drug treatments, KP4 spheroids were indeed significantly more resistant than 2D cultures to a subset of 18 inhibitors from the panel comprised mostly of chemotherapeutics (FIG. 1). Unexpectedly, we also identified 11 inhibitors that were more effective on 3D cultures than the 2D cultures (FIG. 1). These 11 inhibitors comprised of a variety of molecules with reported activities targeting multiple signaling pathways. Four of these inhibitors (Cobimetinib, GDC-0623, AZD6244, PD901) target the MEK pathway, 3 target the PI3K pathway (GDC-0941, GDC-0980, G38390) and one targets the MET pathway (G45203).

Figure 2:
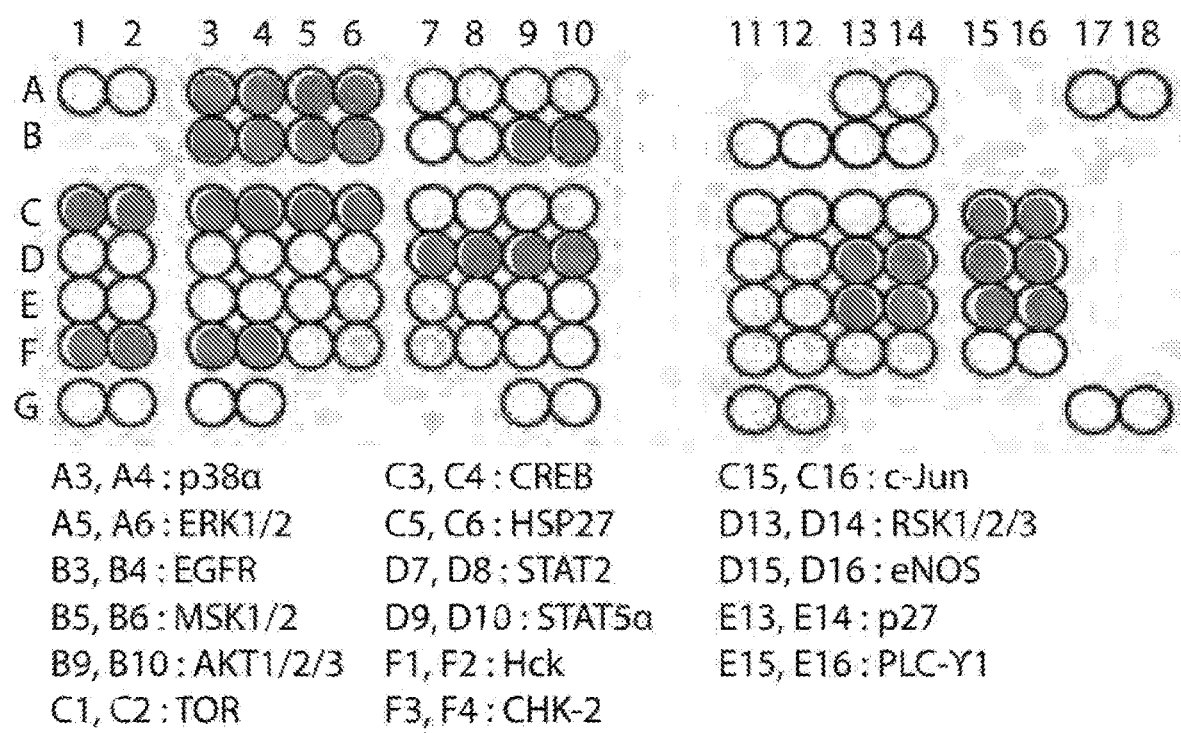
FIG. 2 depicts differential response to MEK inhibition by KP4 PDAC cells in 2D monolayer and 3D spheroid cultures: Phospho-kinase array layout with location of differentially activated proteins in panel C darkened.
Figure 3:
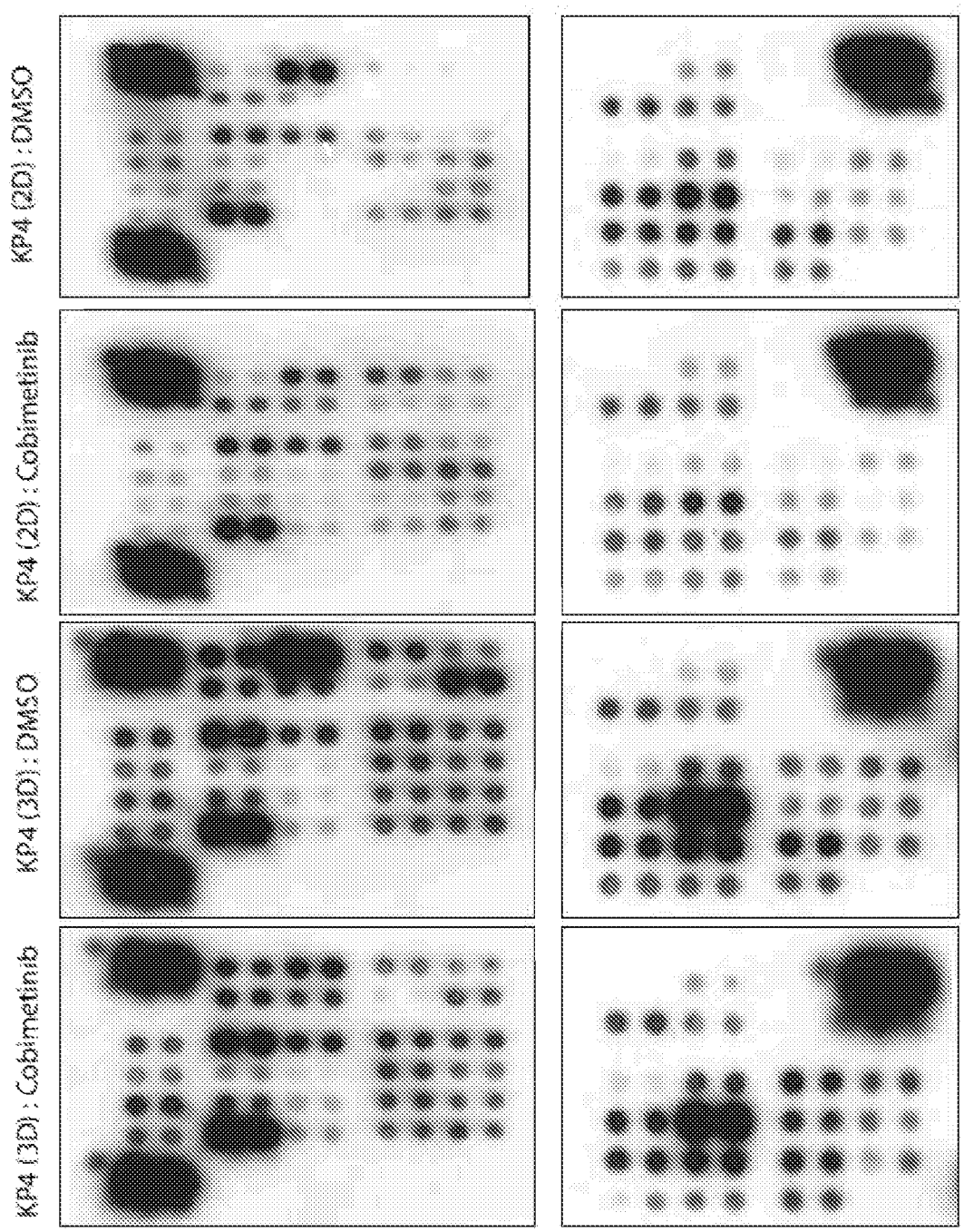
FIG. 3 depicts differential response to MEK inhibition by KP4 PDAC cells in 2D monolayer and 3D spheroid cultures: Phospho-kinase array of KP4 cells in 2D and 3D.
Figure 4:
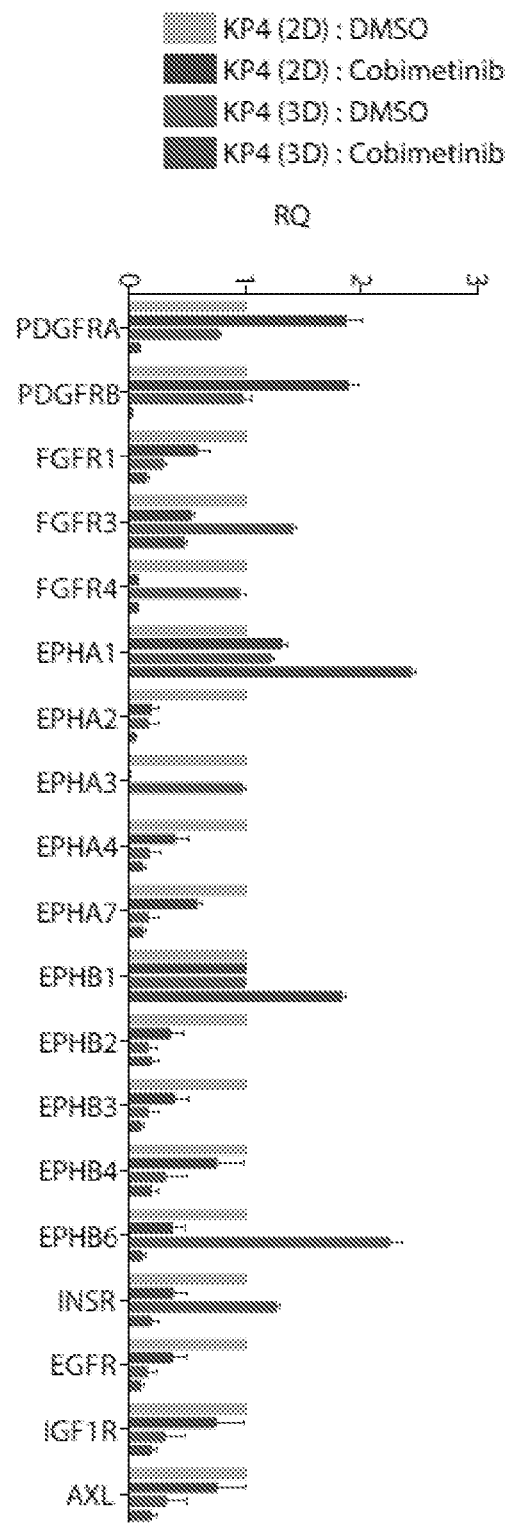
FIG. 4 depicts differential response to MEK inhibition by KP4 PDAC cells in 2D monolayer and 3D spheroid cultures: Protein kinase array by RT-PCR of KP4 cells cultured in 2D or 3D and treated with cobimetinib for 24 hrs. Samples were normalized against DMSO-treated KP4 2D controls.

Example 2: Differentially Regulated Multiple Signaling Pathways in 2D Versus 3D Cultures in Pancreatic Cancer Cells To identify signaling pathways potentially contributing to the observed differential treatment sensitivity of pancreatic cancer cells in 2D versus 3D, we performed phospho-kinase arrays, gene expression arrays, and luciferase expression reporter assays, and compared the changes in the expression levels of signaling proteins in KP4 cells in 2D and 3D conditions. Phospho-kinase arrays showed increased tyrosine phosphorylation of several signaling proteins including p38, ERK, EGFR, MSK, Akt, TOR, CREB, HSP-27, STAT2, STAT5a, Hck, Chk-2, c-Jun, RSK1/2/3, eNOS, p27 and PLC-γ1 in KP4 spheroids in comparison to KP4 cells cultured in 2D, suggesting a substantial "rewiring" of signaling pathways in 3D conditions (FIGS. 2 & 3). In KP4 monolayer cultures, MEK inhibition downregulated ERK, RSK, and PLC-γ1 phosphorylation, and increased activation of STAT family proteins as well as Akt (FIG. 3). In contrast, KP4 spheroids showed decreased activation of Akt and STAT family proteins in addition to ERK, RSK and PLC-γ1 upon MEK inhibition. MEK inhibition only induced activation of c-Jun in KP4 spheroids.

qRT-PCR analysis of expression of mRNAs corresponding to protein kinases in KP4 monolayer and spheroid cultures demonstrated elevated expression in KP4 spheroids for several RTKs; notably, FGFR3, EPHA1, EPHB6 and INSR (FIG. 4). MEK inhibition caused down-regulation of most of these RTK's in both KP4 monolayer and spheroids. However, expression of PDGFRα and PDGFRβ was significantly up-regulated in KP4 monolayer cultures upon cobimetinib treatment. In contrast, expression of EPHA1 and EPHB1 was selectively elevated in KP4 spheroids upon MEK inhibition (FIG. 4). Taken together, these findings reveal a drug response profile specific to 3D culture conditions for PDAC-derived cells that may contribute to the observed differential sensitivity to drug treatment relative to that seen in standard 2D conditions.

Figure 5:
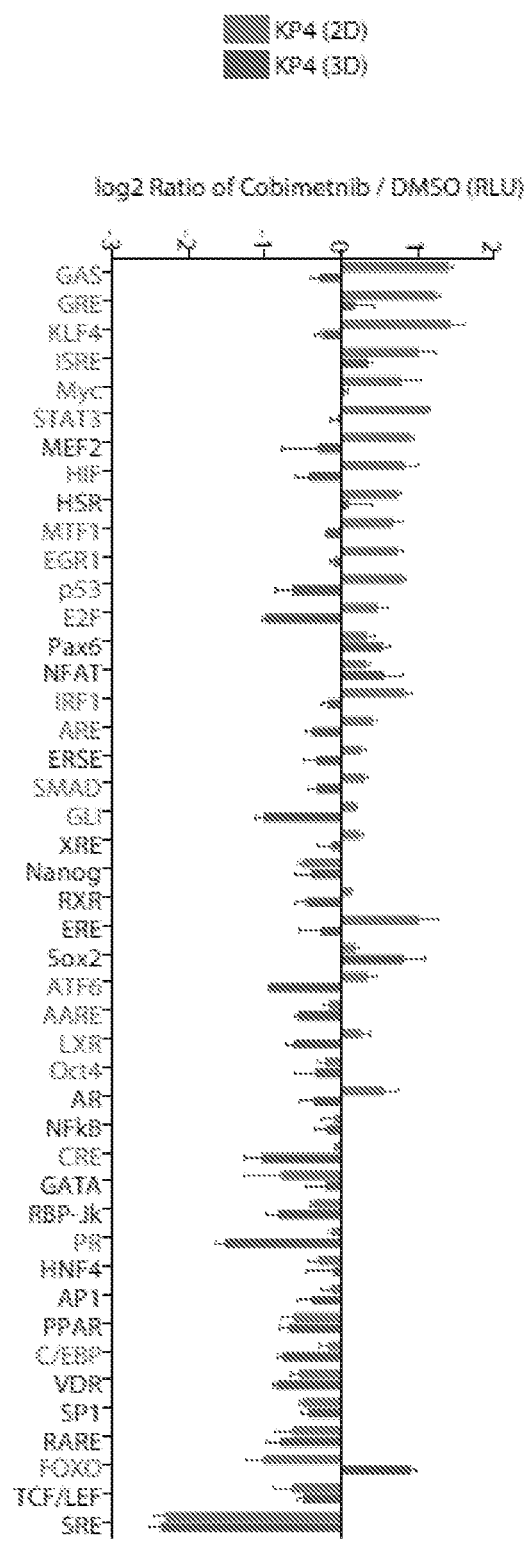
FIG. 5 depicts differential response to MEK inhibition by KP4 PDAC cells in 2D monolayer and 3D spheroid cultures: Luciferase reporter assay of KP4 cells cultured in 2D or 3D and treated with cobimetinib for 24 hrs. The transcription factors with significant difference in fold-change of luciferase activity are shown in red.

Further assessment of alterations in transcription factor pathway activation upon cobimetinib treatment using a large panel of luciferase reporter assays revealed that KP4 monolayer cultures exhibit increased activation of STAT3, c-Myc, GRE, KLF4, ISRE and GAS transcription factors (FIG. 5). In contrast, KP4 spheroids did not demonstrate a similar level of activation of these transcription factors. These results implicate differential regulation of multiple transcription factors that may contribute to the activation of alternate pro-survival signaling pathways in response to MEK pathway inhibition in monolayer versus spheroid conditions.

Figure 6A:
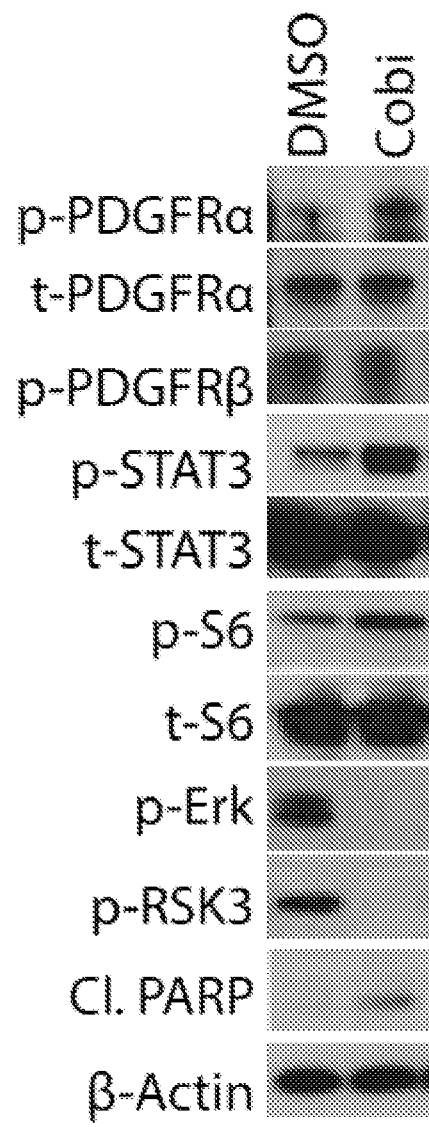
FIGS. 6A-B depict MEK inhibition induces PDGFRα, S6 and STAT3 activation.
Figure 6B:
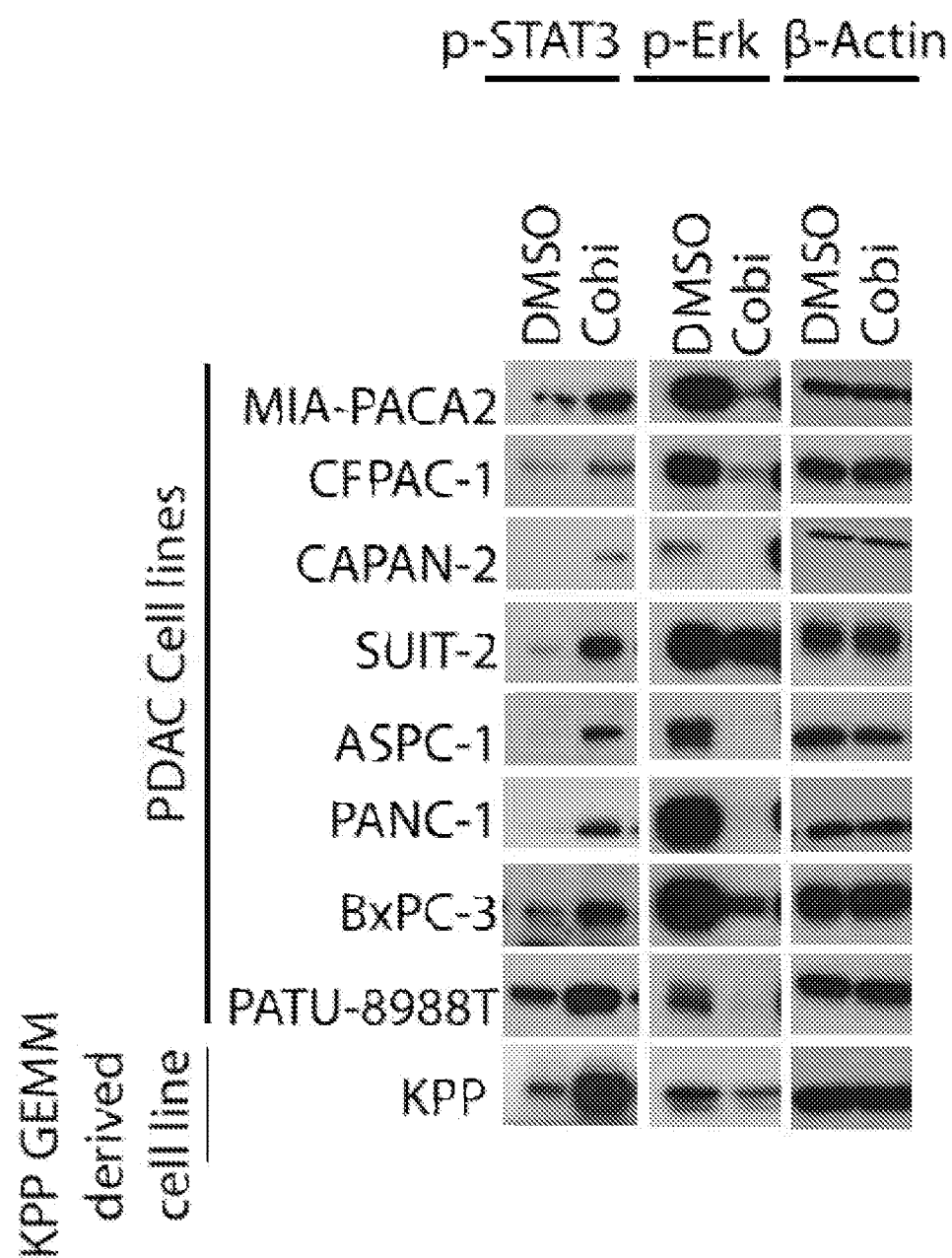
Figure 7:
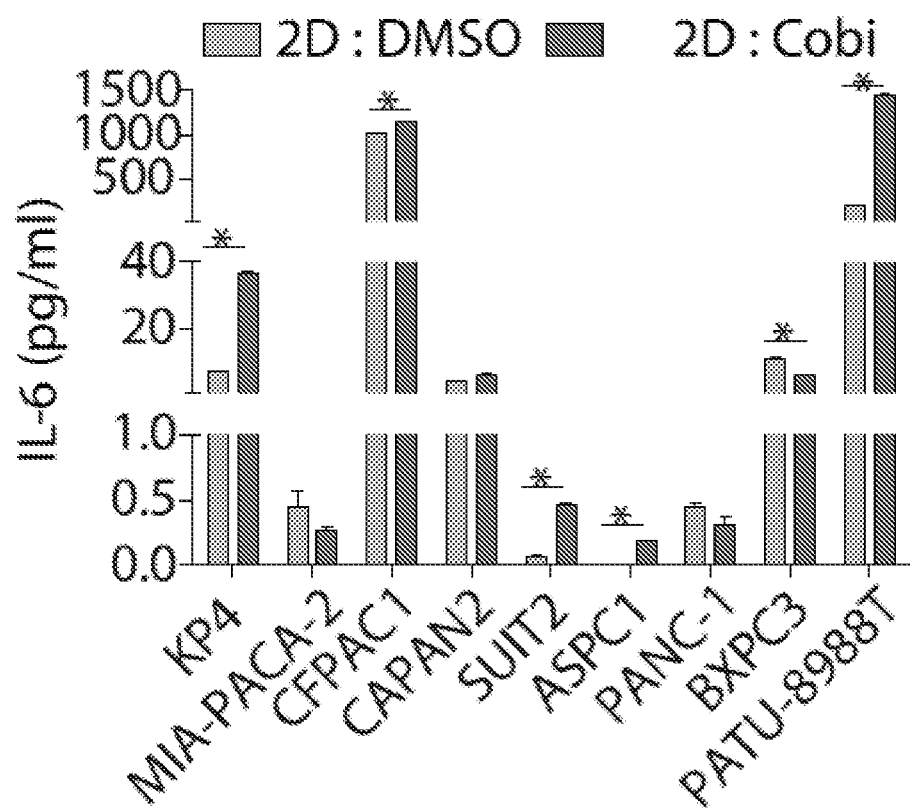
FIG. 7 depicts MEK inhibition induces PDGFRα, S6 and STAT3 activation: Level of IL-6 secretion was measured in 2D culture supernatants of PDAC cell lines treated with cobimetinib for 24 hrs.
Figure 8:
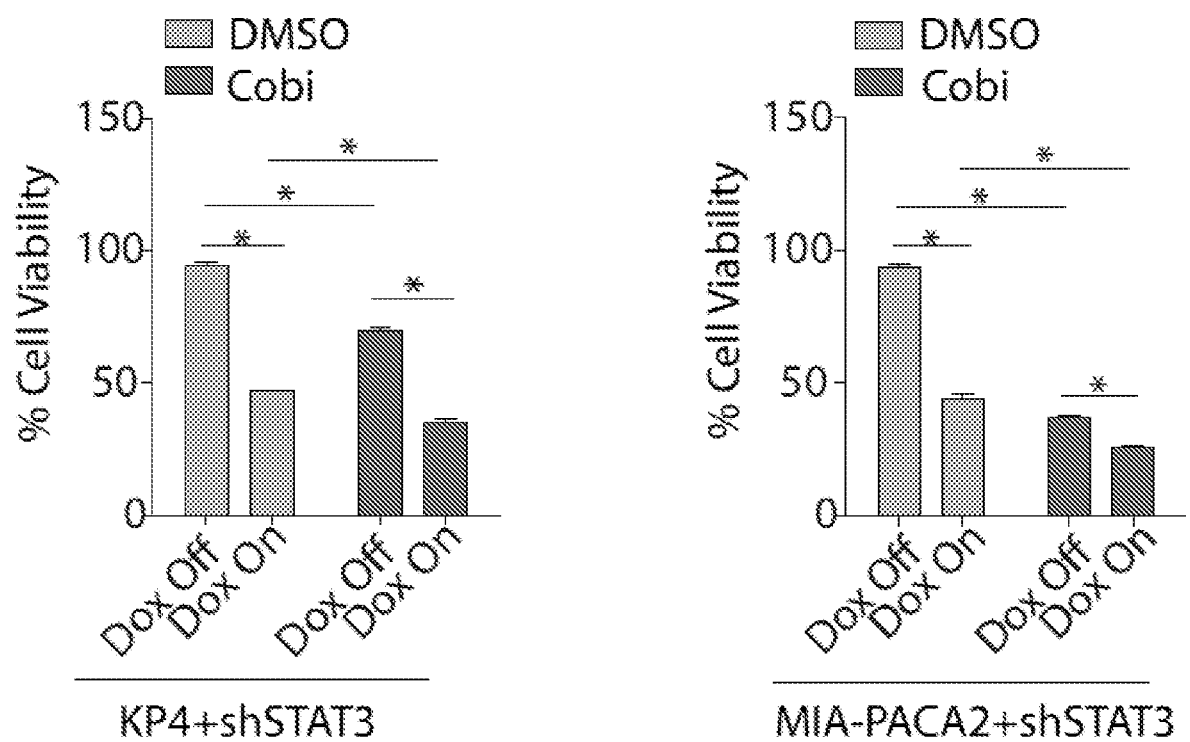
FIG. 8 depicts MEK inhibition induces PDGFRα, S6 and STAT3 activation: CTG assay measuring the effect of Dox-inducible STAT3 knockdown in combination with cobimetinib on KP4 and MIA-PACA2 cell viability.
Figure 9:
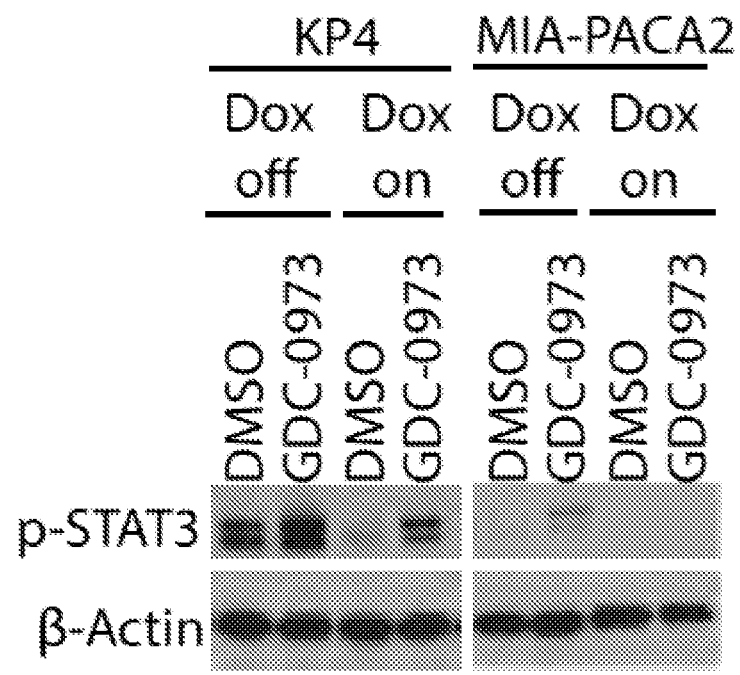
FIG. 9 depicts MEK inhibition induces PDGFRα, S6 and STAT3 activation: Western blot confirming efficient knockdown of STAT3 after 72 hour treatment with Dox (1 μg/ml).
Figure 10:
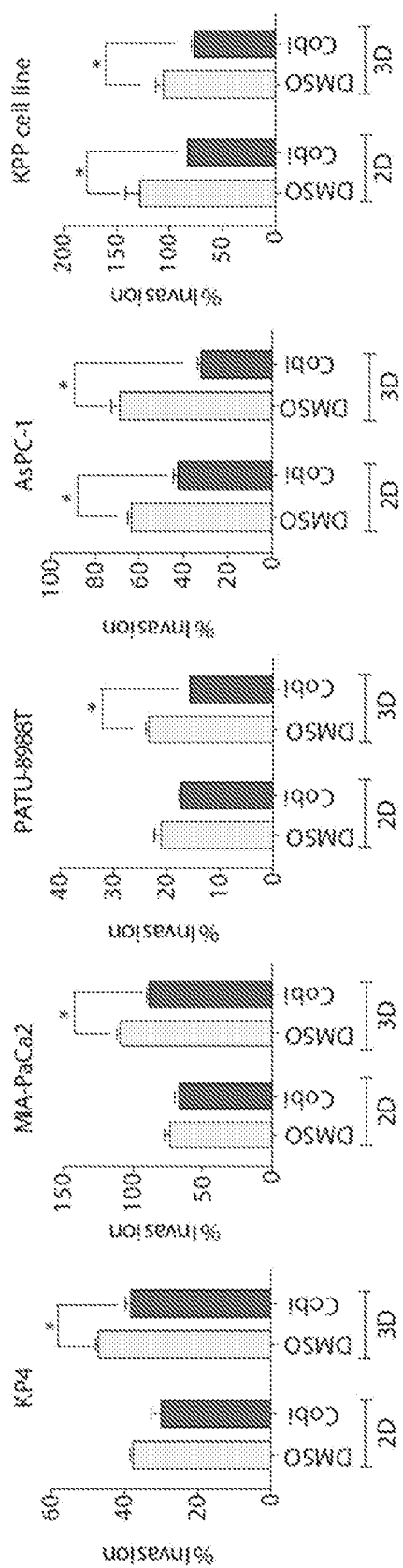
FIG. 10 depicts MEK inhibition induces PDGFRα, S6 and STAT3 activation: Quantification of invasion potential of pancreatic cancer cells cultured in 2D and 3D in response to 10% FBS in a Matrigel invasion assay.

The phospho-kinase array and gene expression array results were validated by western blot for p-PDGFRα, p-STAT3, p-Erk, p-S6 and p-RSK upon cobimetinib treatment of KP4 cells, and an increased level of activation of p-PDGFRα, p-STAT3 and p-S6 was observed (FIG. 6A). Increased p-STAT3 was also reproducibly detected upon cobimetinib treatment in multiple PDAC human cancer cell lines (FIG. 6B). Significantly, increased secretion of the IL-6 ligand, which can promote STAT3 activation, was also observed in multiple PDAC cell lines (FIG. 7). Consistent with a requirement for STAT3 activation, RNAi knockdown of STAT3 in KP4 and MIA-PACA2 cells induced cell death upon cobimetinib treatment (FIGS. 8 & 9). In addition, an in vitro cell invasion assay with multiple PDAC cell lines and a KPP GEMM tumor-derived cell line demonstrated decreased invasion potential of cancer cells upon MEK inhibition (FIG. 10). These results suggest that although MEK inhibition as a single agent is not sufficient to cause primary tumor regression, it can inhibit the invasion potential of cancer cells. Together, these results suggest that signaling pathways mediated by PDGFRα, S6, and STAT3 may enable cancer cell survival upon MEK inhibition in pancreatic cancer cells.

Figure 11:
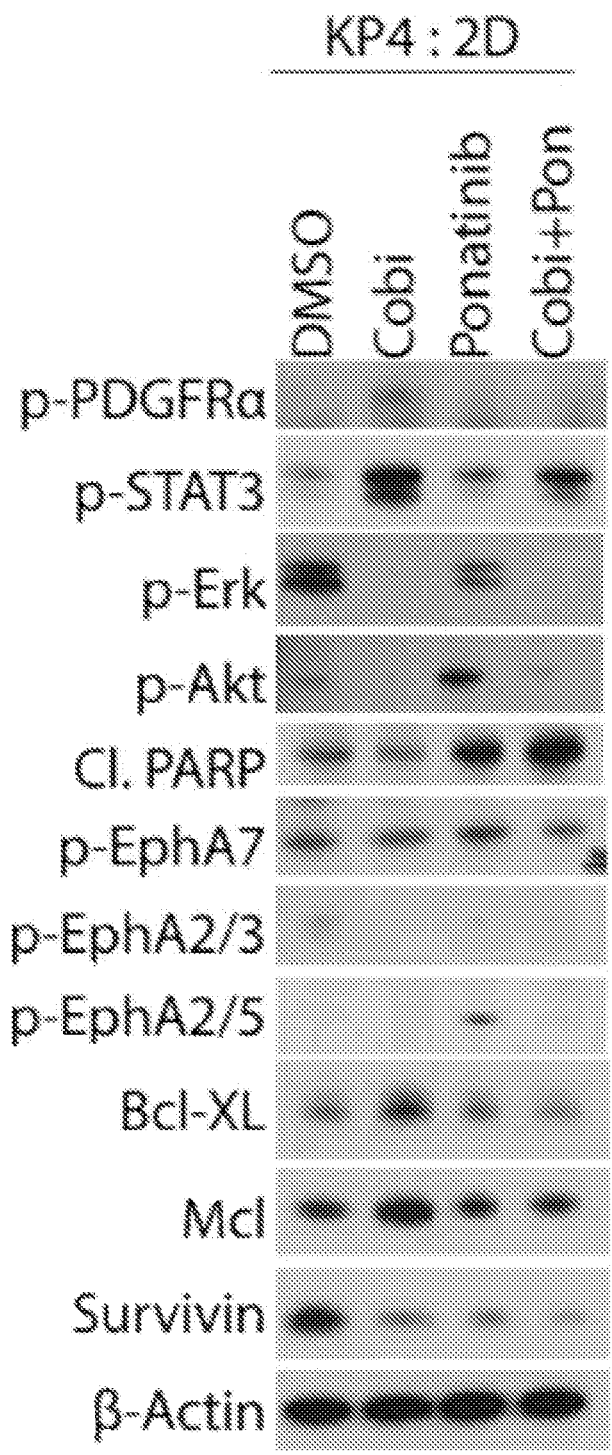
FIG. 11 depicts the inhibition of S6 and STAT3 in combination with cobimetinib increases death of pancreatic cancer cells: Effect of the multi-RTK inhibitor ponatinib in combination with cobimetinib on activation of signaling receptors and downstream targets was validated by western blot.
Figure 12:
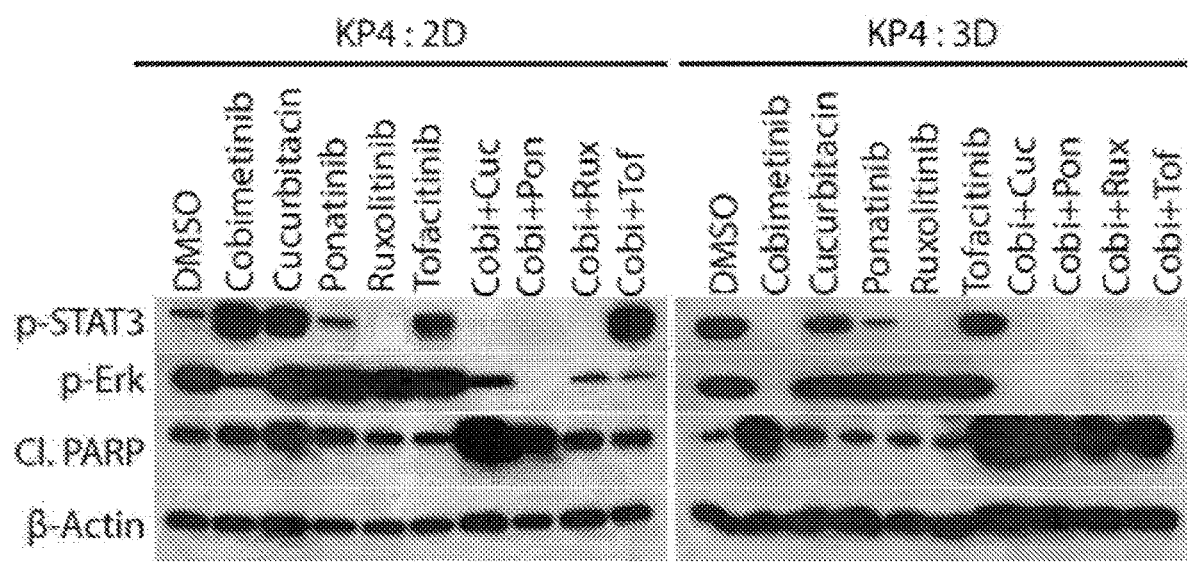
FIG. 12 depicts the inhibition of S6 and STAT3 in combination with cobimetinib increases death of pancreatic cancer cells: Effect on STAT3 activation and induction of cleaved PARP upon cobimetinib+/−ponatinib or JAK inhibitors was validated by western blot.
Figure 13:
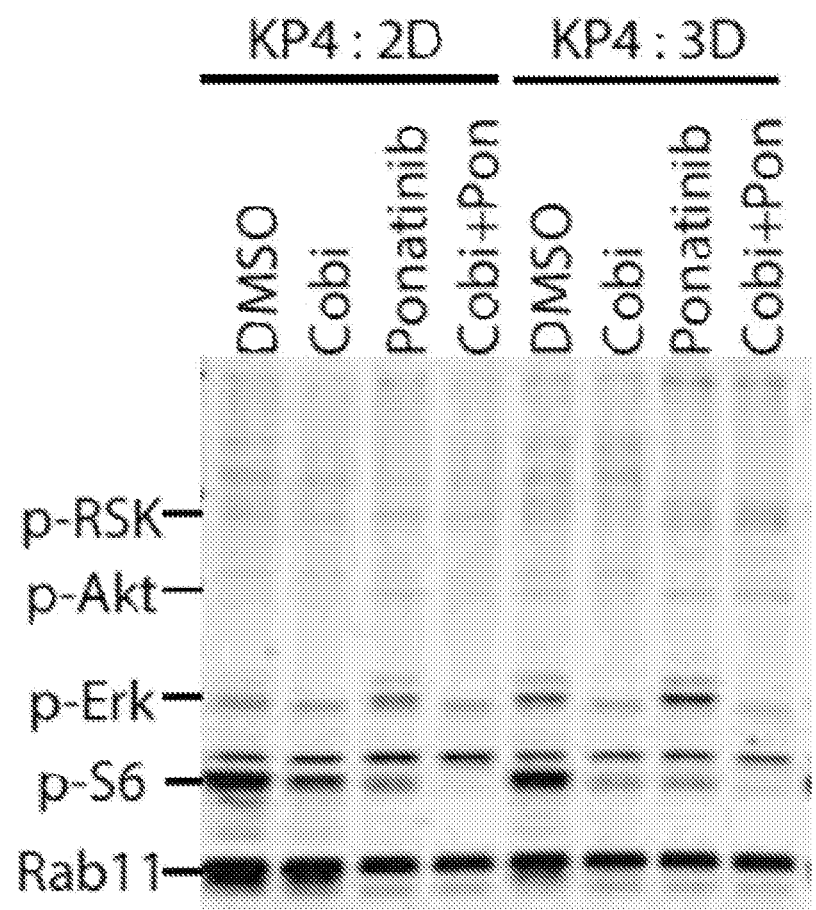
FIG. 13 depicts the inhibition of S6 and STAT3 in combination with cobimetinib increases death of pancreatic cancer cells: PathScan Multiplex western blot analysis of KP4 cells pretreated with cobimetinib+/−ponatinib in 2D and 3D cultures.

Example 3: Inhibition of PDGFRα, S6 and STAT3 Together with MEK Inhibition Effectively Promotes Apoptosis of PDAC Cells Previous studies have reported that MEK inhibition can lead to up-regulation and activation of multiple RTKs and the IL6/JAK/STAT pathway as a "bypass" survival mechanism (Duncan J S, Whittle M C, Nakamura K, Abell A N, Midland A A, Zawistowski J S, Dynamic reprogramming of the kinome in response to targeted MEK inhibition in triple-negative breast cancer, *Cell*, 2012; 149(2):307-21. Epub 2012/04/17; Lee H J, Zhuang G, Cao Y, Du P, Kim H J, Settleman J, Drug resistance via feedback activation of Stat3 in oncogene-addicted cancer cells, *Cancer Cell*, 2014; 26(2):207-21, Epub 2014/07/30; Dai B, Meng J, Peyton M, Girard L, Bornmann W G, Ji L, STAT3 mediates resistance to MEK inhibitor through microRNA miR-17, *Cancer Research*, 2011; 71(10):3658-68, Epub 2011/03/30). However, pancreatic cancer has not been implicated. The effectiveness of the multi-RTK inhibitor ponatinib, which targets both S6 and the JAK2/STAT3 cascade, alone or in combination with cobimetinib, was tested in a tumor cell growth assay. Cobimetinib treatment promoted STAT3 and S6 activation in PDAC cell lines (FIG. 6A), and combination treatment with cobimetinib/ponatinib inhibited activation of PDGFRα, STAT3, S6, ERK1/2, Akt, decreased expression of pro-survival proteins Bcl-XL, Mcl-1, survivin, and increased levels of cleaved PARP in 2D as well as 3D cultures (FIGS. 11, 12 and 13). Although ponatinib has previously been reported to inhibit the kinase activity of Ephrin receptors that could potentially regulate downstream signaling pathways in PDAC cells, the cobimetinib/ponatinib combination treatment did not affect the activity of Ephrin receptors (EphA2/3, EphA2/5 and EphA7) in the PDAC model (FIG. 11).

Figure 14:
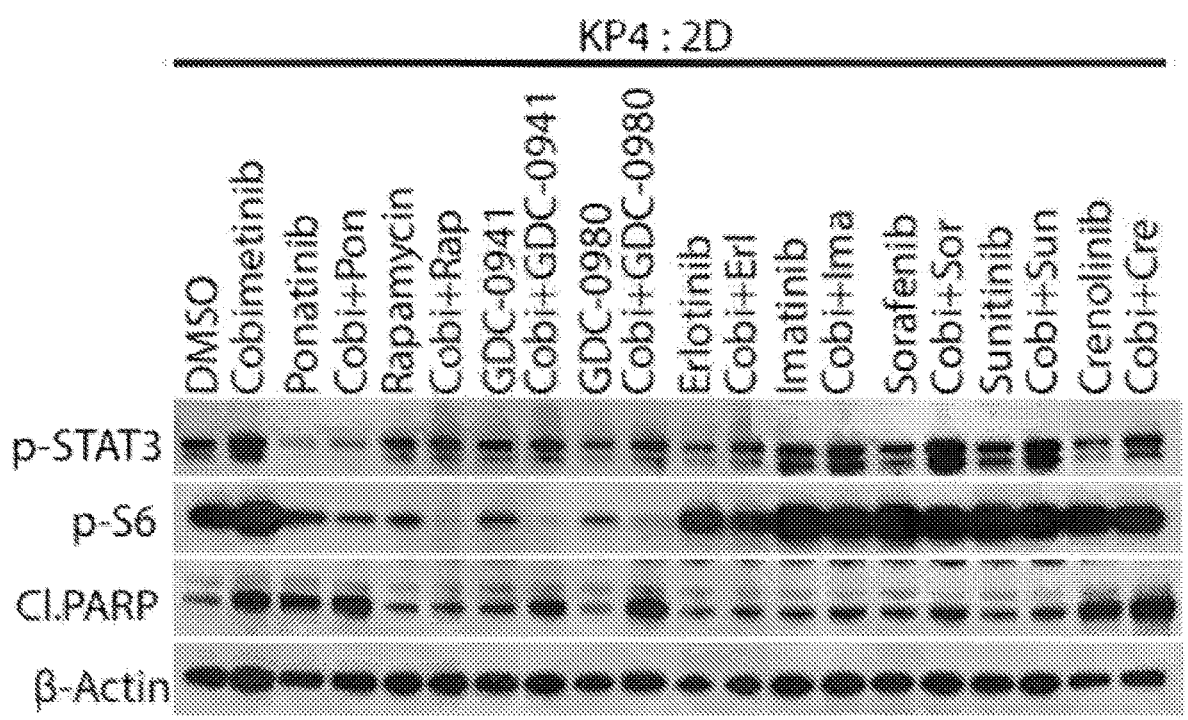
FIG. 14 depicts the inhibition of S6 and STAT3 in combination with cobimetinib increases death of pancreatic cancer cells: Effect on S6 activation and induction of cleaved PARP upon cobimetinib+/−ponatinib/S6/PDGFRα inhibitors was validated by western blot.
Figure 15:
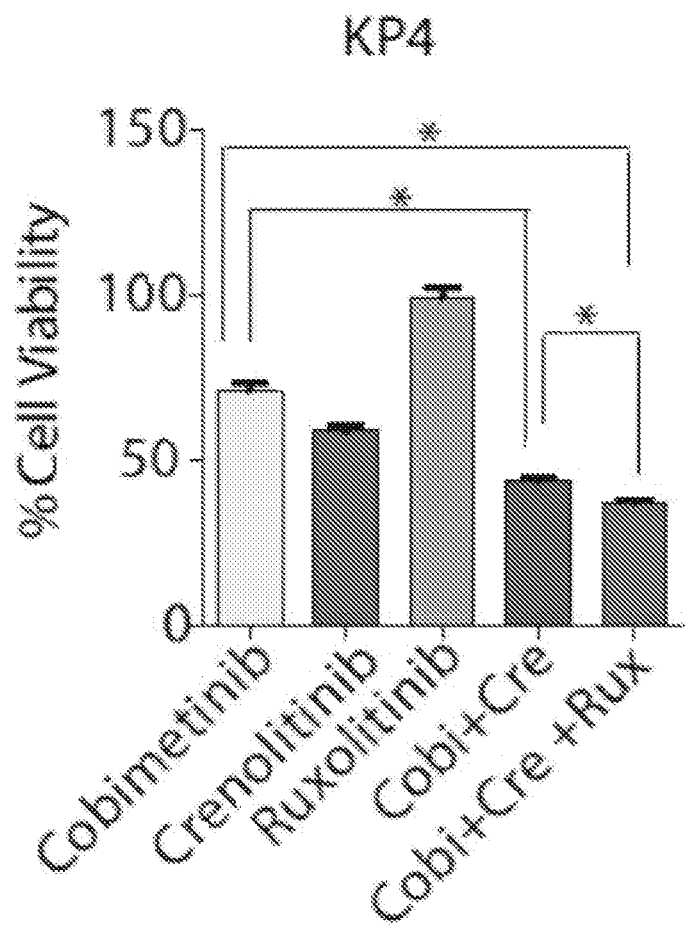
FIG. 15 depicts the inhibition of S6 and STAT3 in combination with cobimetinib increases death of pancreatic cancer cells: Effect of the PDGFR inhibitor crenolanib in combination with cobimetinib and ruxolitinib on KP4 cell viability was measured using the CTG assay.
Figure 16:
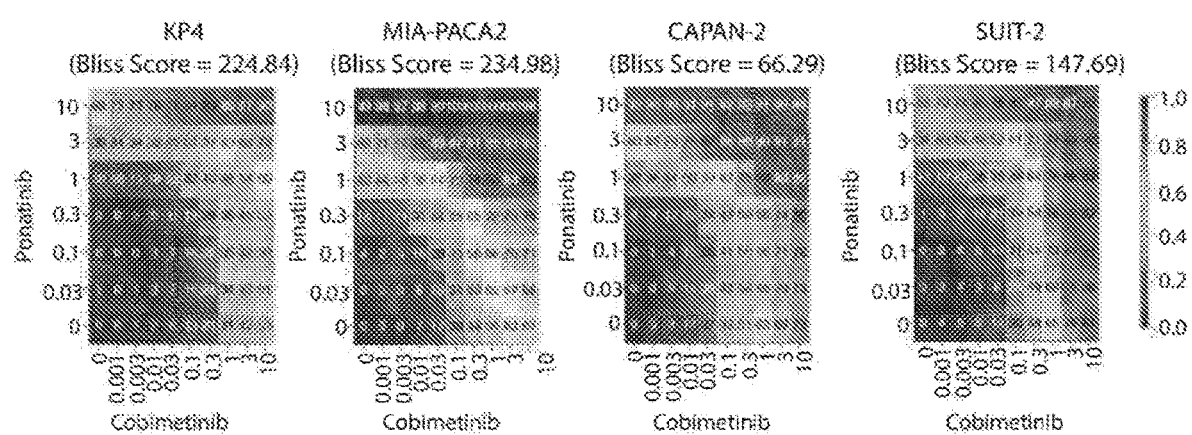
FIGS. 16 and 17 depict the inhibition of S6 and STAT3 in combination with cobimetinib increases death of pancreatic cancer cells: Synergy between cobimetinib and ponatinib was analyzed in pancreatic cancer cell lines using Bliss analysis.
Figure 17:
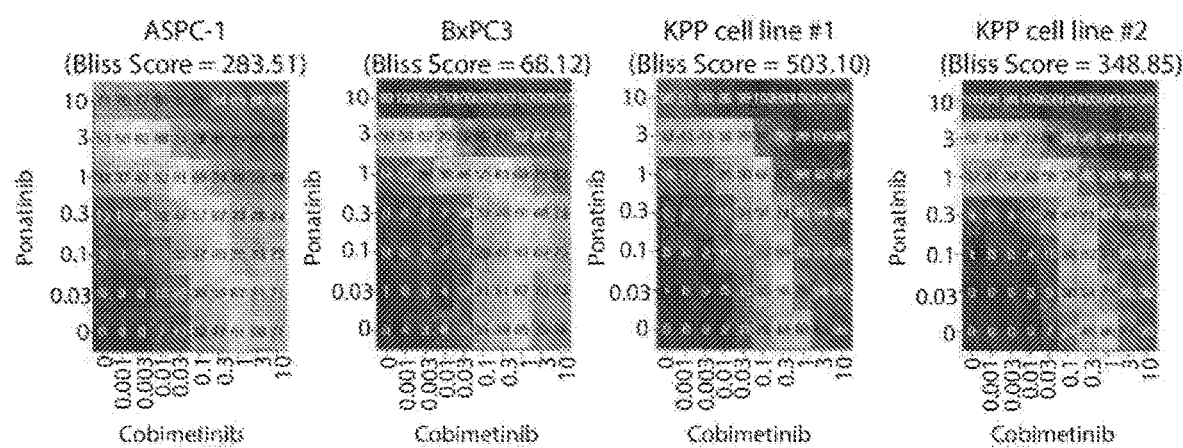
Figure 18:
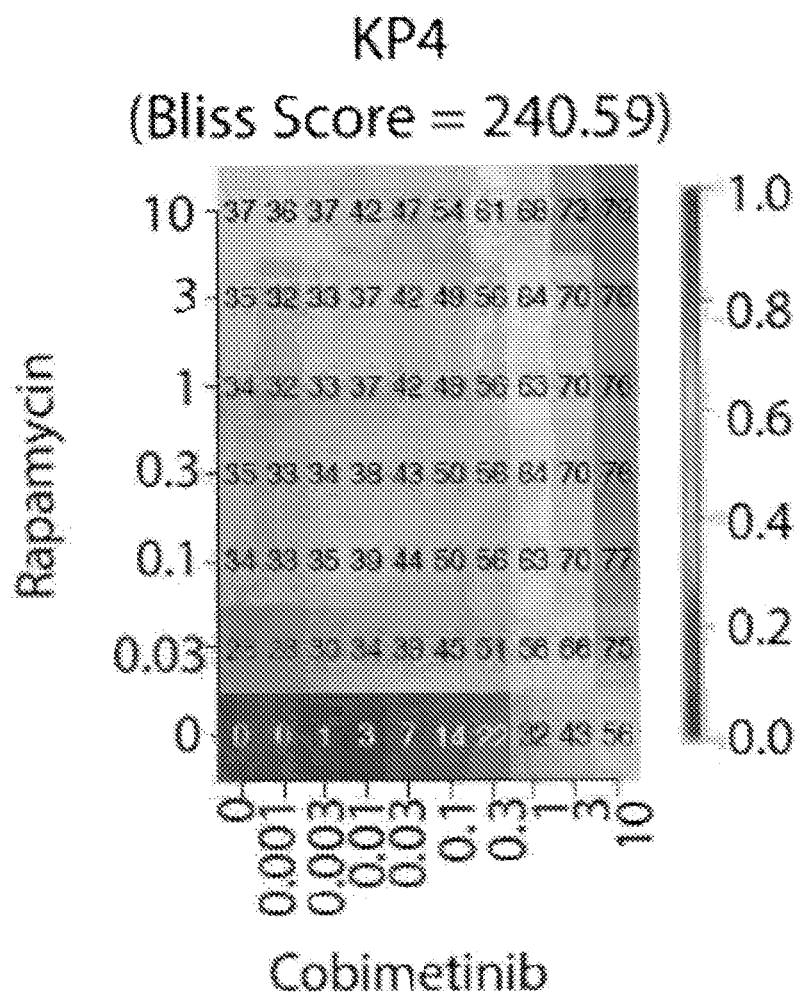
FIG. 18 depicts the inhibition of S6 and STAT3 in combination with cobimetinib increases death of pancreatic cancer cells: Bliss analysis of synergy between cobimetinib and the S6 inhibitor rapamycin in KP4 cells.
Figure 19:
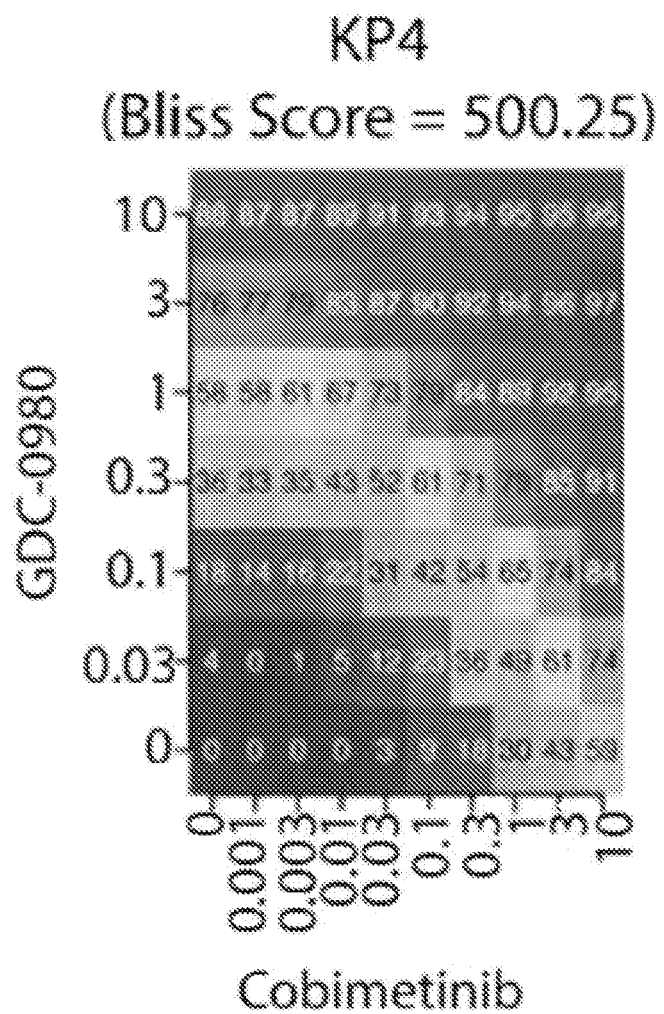
FIG. 19 depicts the inhibition of S6 and STAT3 in combination with cobimetinib increases death of pancreatic cancer cells: Bliss analysis of synergy between cobimetinib and GDC-0980 in KP4 cells.
Figure 20A:
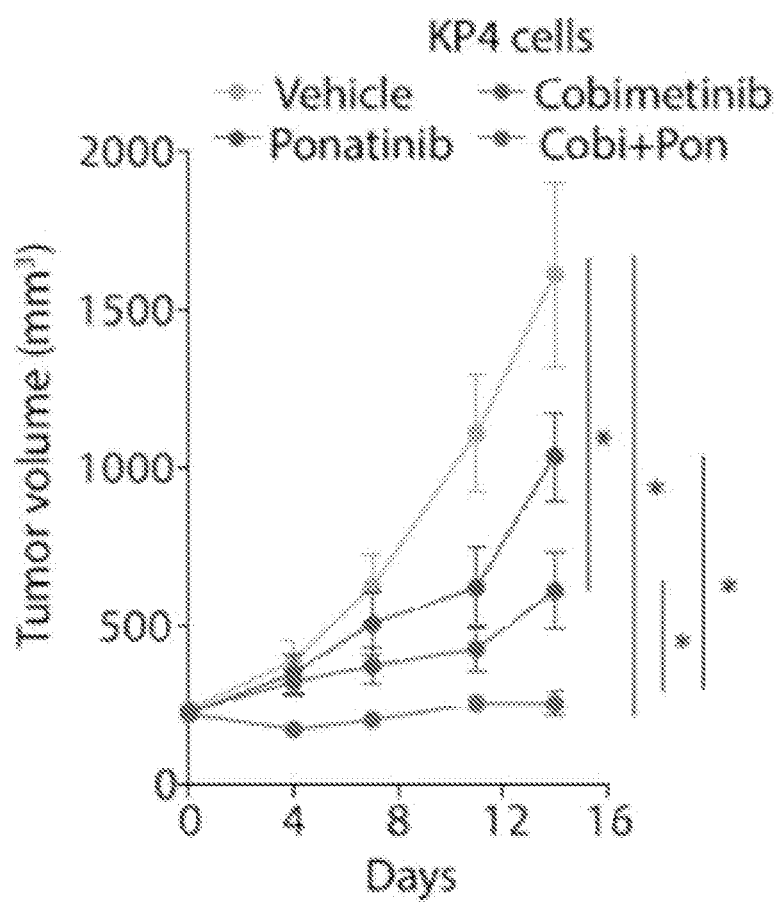
FIGS. 20A-B depict inhibition of PDGFRα/S6/STAT3 and MEK impairs tumor growth and decreases serum PDGFα.
Figure 20B:
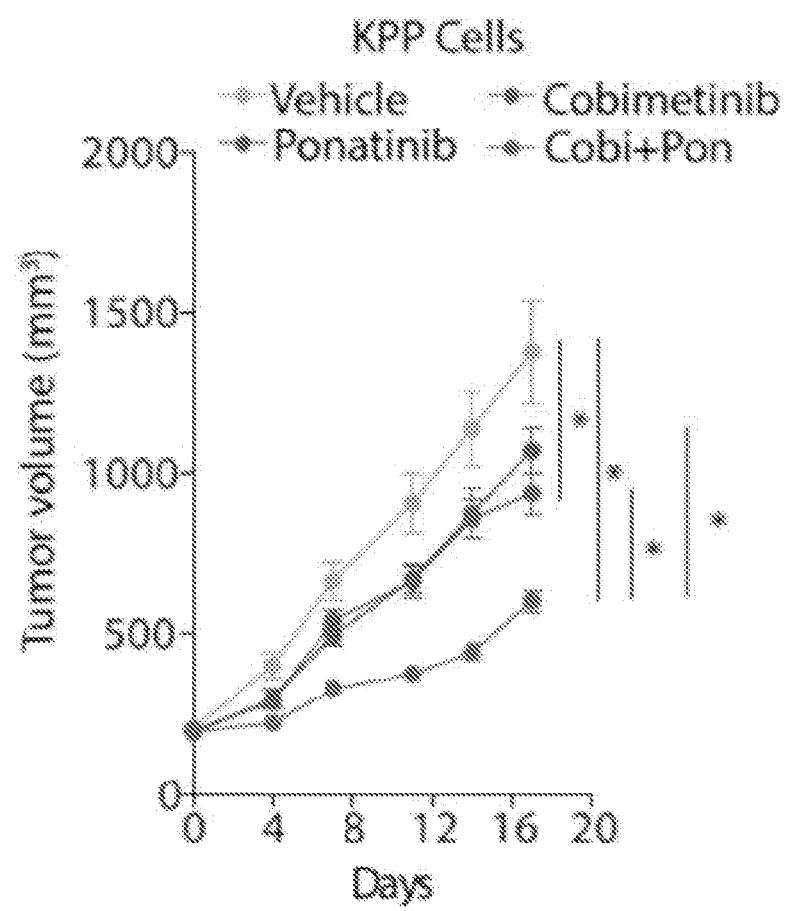

Since ponatinib inhibits PDGFRα in addition to FGFR, VEGFR, Ephrin receptors, as well as S6 and JAK2/STAT3 signaling, we further explored the selective activity of ponatinib by examining the effect of other PDGFRα, S6 and JAK2 inhibitors in combination with cobimetinib. In contrast to effects of the EGFR inhibitor erlotinib or PDGFR inhibitors, down-regulation of S6 activation by a combination treatment with cobimetinib and S6 inhibitors, rapamycin or GDC-0980 promoted cell death in KP4 cells (FIGS. 14, 18 and 19). Simultaneous down-regulation of PDGFRα and STAT3 activation following a triple combination treatment with the PDGFRα inhibitor, crenolanib, the JAK2 inhibitor ruxolitinib, and cobimetinib also inhibited KP4 cell growth and caused significant cell death (FIG. 15). However, we observed the strongest synergy with the cobimetinib/ponatinib treatment, which co-targets RTKs, S6 and JAK/STAT, and effectively inhibited the growth of PDAC cells (FIGS. 11, 12, 13, 14, 16 and 17). Treatment of PDAC cell lines with cobimetinib and/or ponatinib had no effect on cell viability as single agents, but was synergistic in inhibiting cell growth in combination in both 2D and 3D cultures, revealing the cobimetinib/ponatinib combination as a potentially effective therapeutic strategy for PDAC (FIGS. 12, 16 and 17).

Figure 22:
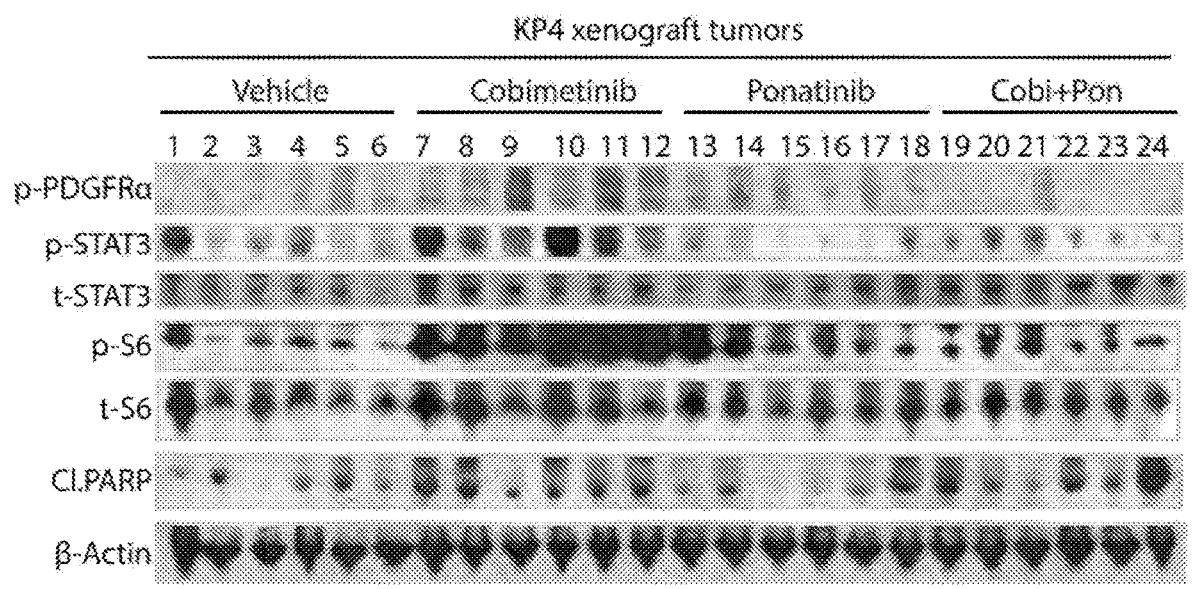
FIG. 22 depicts inhibition of PDGFRα/S6/STAT3 and MEK impairs tumor growth and decreases serum PDGFα: Immunoblot validating activation of PDGFRα, S6 and STAT3 upon cobimetinib/Ponatinib treatment of KP4 xenograft tumors.
Figure 23:
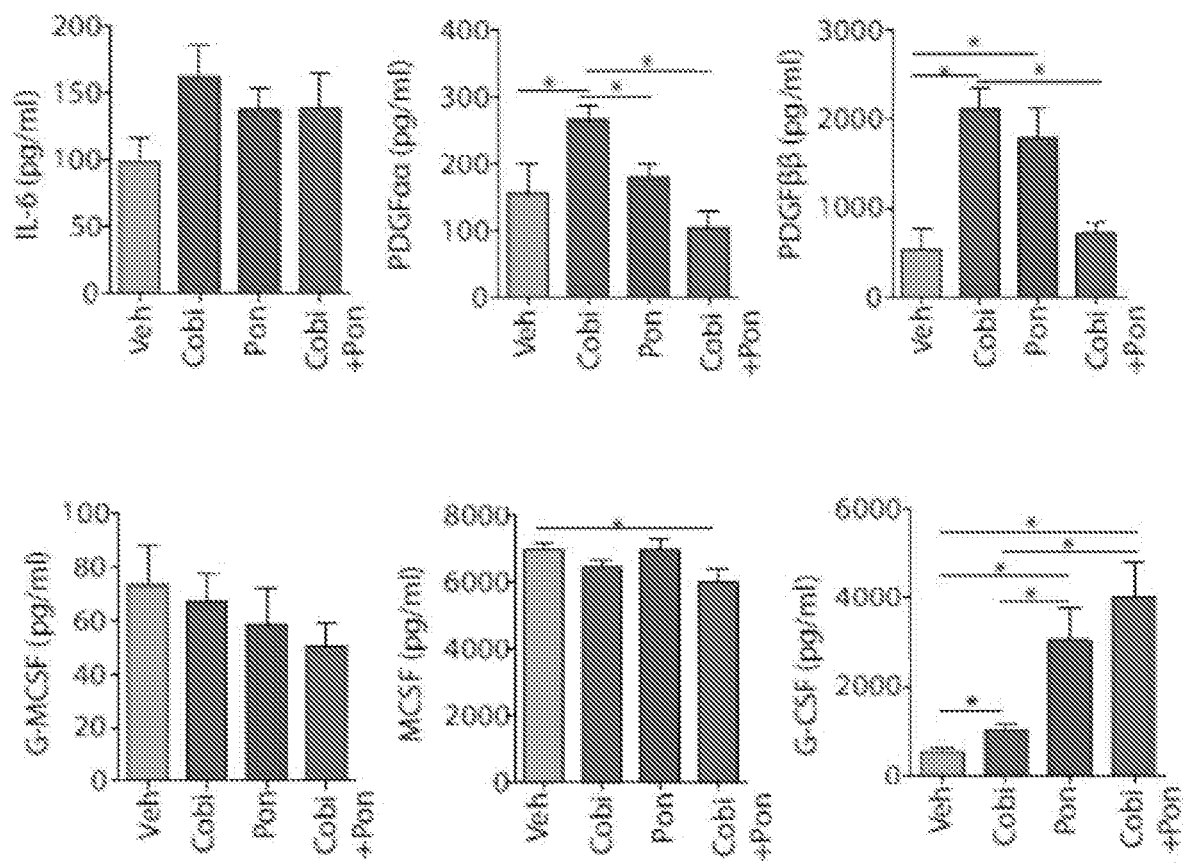
FIG. 23 depicts inhibition of PDGFRα/S6/STAT3 and MEK impairs tumor growth and decreases serum PDGFα: Luminex assay for growth factors and cytokines of plasma samples of KP4 xenograft mice.
Figure 31A:
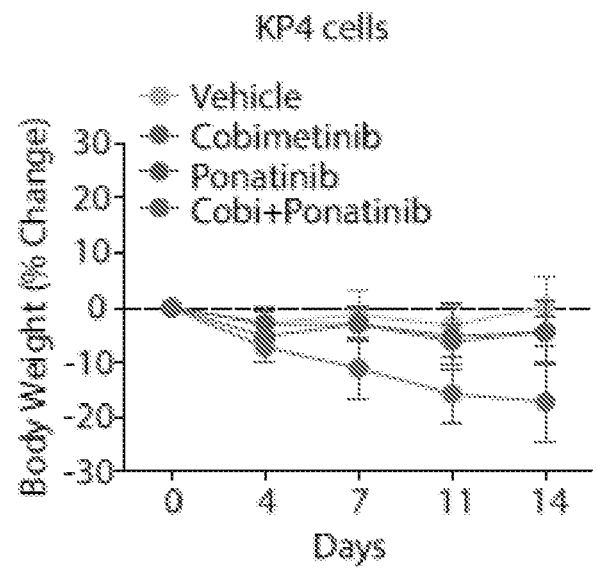
FIGS. 31A-B depict cobimetinib/ponatinib co-treatment impairs tumor growth and decreases tumor-associated macrophage infiltration: Change in body weight of mice treated with cobimetinib+/−ponatinib in KP4 and KPP xenograft models.
Figure 31B:
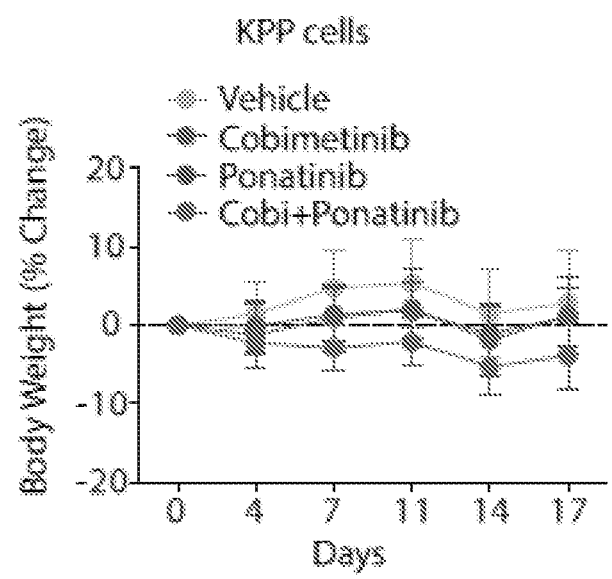
Figure 32:
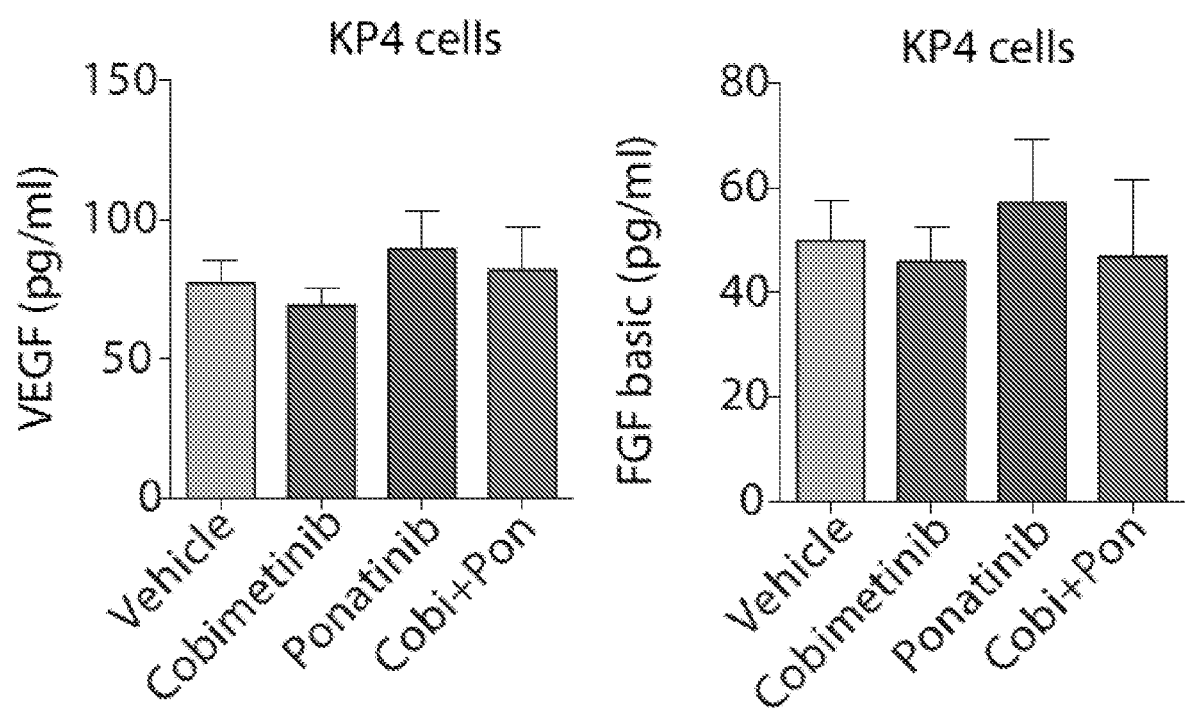
FIG. 32 depicts cobimetinib/ponatinib co-treatment impairs tumor growth and decreases tumor-associated macrophage infiltration: Luminex assay of growth factors of plasma samples of KP4 xenograft mice.
Figure 33:
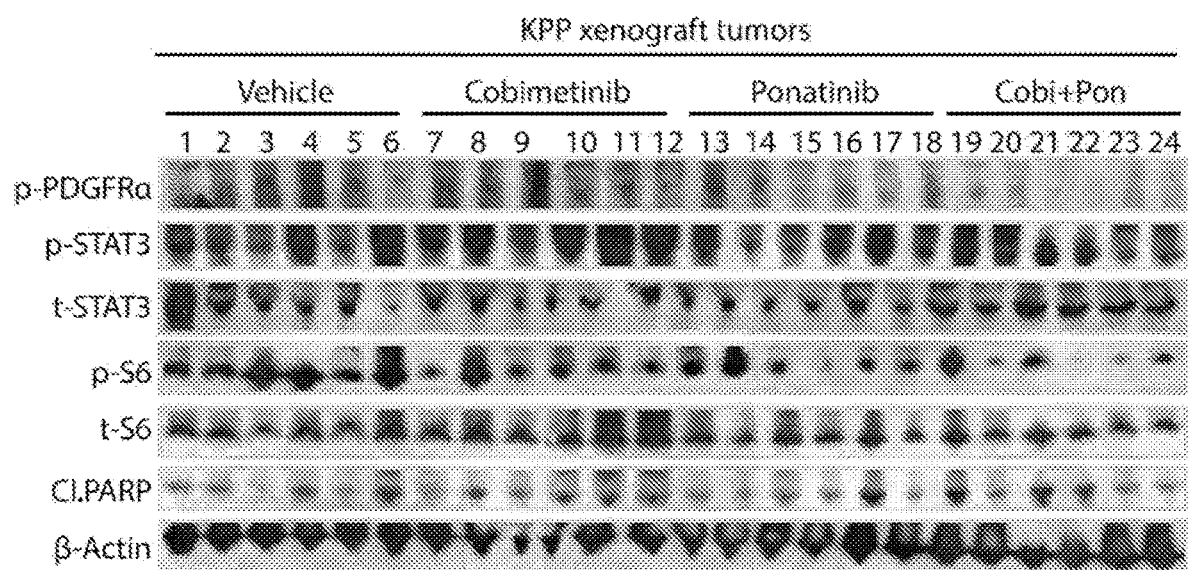
FIG. 33 depicts cobimetinib/ponatinib co-treatment impairs tumor growth and decreases tumor-associated macrophage infiltration: Immunoblot validating activation of PDGFRα, S6 and STAT3 upon cobimetinib/Ponatinib treatment of KPP xenograft tumors.

Example 4: Cobimetinib/Ponatinib Co-Treatment Induces Tumor Regression in Mouse Models To test the effectiveness of the cobimetinib/ponatinib combination in vivo, we performed xenograft studies with KP4 and KPP GEMM-derived tumor cells. Both cobimetinib and ponatinib were ineffective as single agents in KP4 xenografts, but co-treatment with cobimetinib and ponatinib caused significant inhibition of tumor growth and increased cell death with increased cleaved caspase 3 (FIGS. 20 (KP4 cells), 21 and 22). Similar results were obtained with KPP GEMM-derived cell line xenograft tumors, although we primarily observed a marked delay in tumor growth as opposed to tumor regression (FIG. 20 (KPP cells)). The cobimetinib/ponatinib combination treatment also resulted in 103% TGI (% Tumor Growth Inhibition) in KP4 xenografts and 71% TGI in KPP xenografts (Table 2). The cobimetinib/ponatinib combination treatment did drive some combinatorial body weight loss in mice in the KP4 xenograft study but not in KPP GEMM-derived xenograft study. In KP4 xenograft study, two mice had to be taken off early in the study due to >20% body weight loss. However, no significant weight loss beyond the acceptable threshold was observed in the remaining mice during the course of the combination treatment (FIG. 31A). Histopathological analysis, IHC staining and immunoblotting of the grafted tumors confirmed the expected induction of p-PDGFRα, p-STAT3 and pS6 upon cobimetinib treatment, which was significantly down-regulated following co-treatment with cobimetinib and ponatinib (FIGS. 21, 22, 30 and 33). Significantly elevated serum levels of PDGFα, PDGFβ, and increased levels of IL-6 were also observed in the cobimetinib-treated mice (FIG. 23). Cobimetinib/ponatinib co-treatment reduced serum PDGFα and PDGFβ levels but not VEGF or FGF levels, highlighting the specific relevance of the PDGFRα pathway by ponatinib in the PDAC cancer model (FIGS. 23 and 32).

Figure 21:
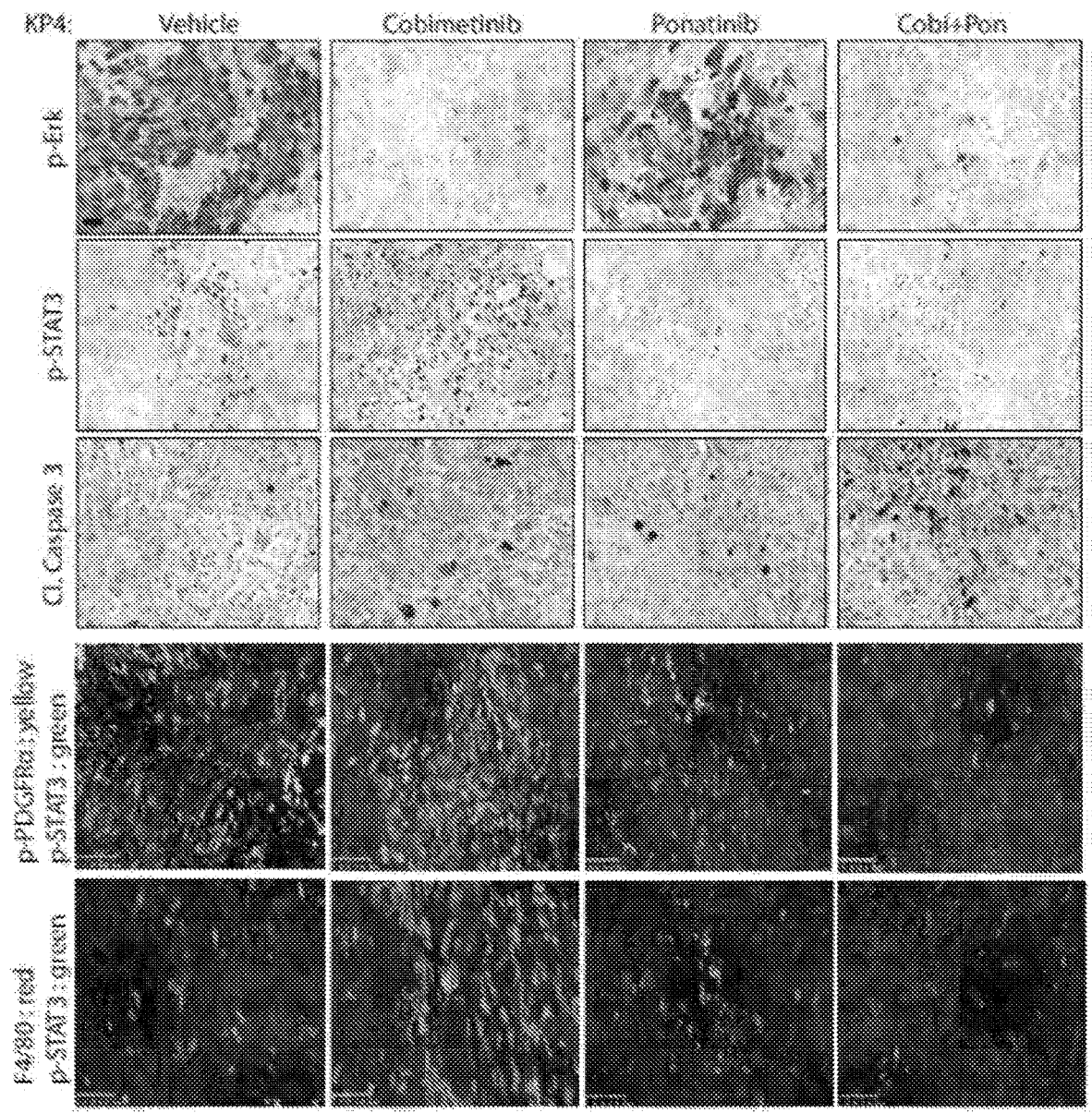
FIG. 21 depicts inhibition of PDGFRα/S6/STAT3 and MEK impairs tumor growth and decreases serum PDGFα: Representative tumor sections from KP4 xenografts stained to detect p-STAT3, p-Erk and cleaved caspase 3 by IHC, or co-stained with antibodies against p-STAT3 and F4/80 or p-PDGFRα by IF. Scale bar: 20 μm for IHC slides, 50 μm for IF slides.

Analysis of the myeloid cell compartment within PDAC tumors revealed that F4/80$^+$ tumor-associated macrophages (TAMs) were the most predominant myeloid population (FIG. 21). Cobimetinib/ponatinib co-treatment significantly reduced the number of TAMs in tumors, induced the serum levels of macrophage inhibiting factor GCSF, and reduced the levels of macrophage activating factors GM-CSF and MCSF (FIGS. 22 and 23). These findings indicate that cobimetinib/ponatinib co-treatment is effective in abrogating both tumor cell and myeloid cell populations by targeting the PDGFRα pathway in addition to downstream MEK, S6 and STAT3 survival pathways. In addition, the findings suggest that this combination treatment can promote tumor regression.

TABLE 2

Tumor growth inhibition (% TGI) of KP4 and KPP xenografts

| | n/group | n/last day | Tumor volume (last day) | % TGI (AUC vs. Vehicle) | % TGI 95$^{th}$ percentile Upper UI | % TGI 95$^{th}$ percentile Lower UI | TTP 2X |
|---|---|---|---|---|---|---|---|
| KP4 xenografts Treatment | | | | | | | |
| Vehicle | 10 | 10 | 1316 | 0 | 0 | 0 | 6 |
| Ponatinib (30 mg/kg, PO, QD) | 10 | 9 | 408 | 56 | −22 | 87 | 8.5 |
| Cobimetinib (5 mg/kg, PO, QD) | 10 | 10 | 532 | 70 | 7 | 97 | 13 |
| Cobi (5 mg/kg, PO, QD) + Pon (30 mg/kg, PO, QD) | 10 | 7 | 217 | 103 | 76 | 123 | NA |
| KPP xenografts Treatment | | | | | | | |
| Vehicle | 10 | 10 | 1305 | 0 | 0 | 0 | 4.5 |
| Ponatinib (30 mg/kg, PO, QD) | 10 | 10 | 1045 | 29 | 3 | 50 | 7 |
| Cobimetinib (5 mg/kg, PO, QD) | 10 | 10 | 917 | 31 | 5 | 50 | 6.5 |
| Cobi (5 mg/kg, PO, QD) + Pon (30 mg/kg, PO, QD) | 10 | 10 | 576 | 71 | 60 | 80 | 12.5 |

AUC = Area Under the Curve
UI = Uncertainty Interval
TTP = Time to Tumor Progression (2X original volume)

Figure 24:
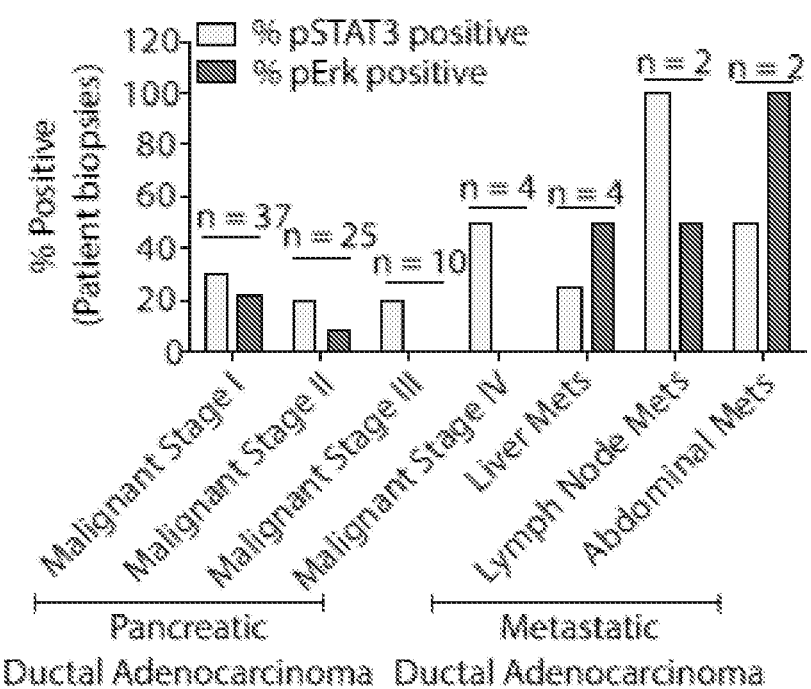
FIG. 24 depicts analysis of p-Erk and p-STAT3 in pancreatic tumors and metastases from PDAC patient samples: Distribution of p-Erk- and p-STAT3-positive samples in different stages of malignancies in primary tumors and metastases from 82 PDAC patients.
Figure 25:
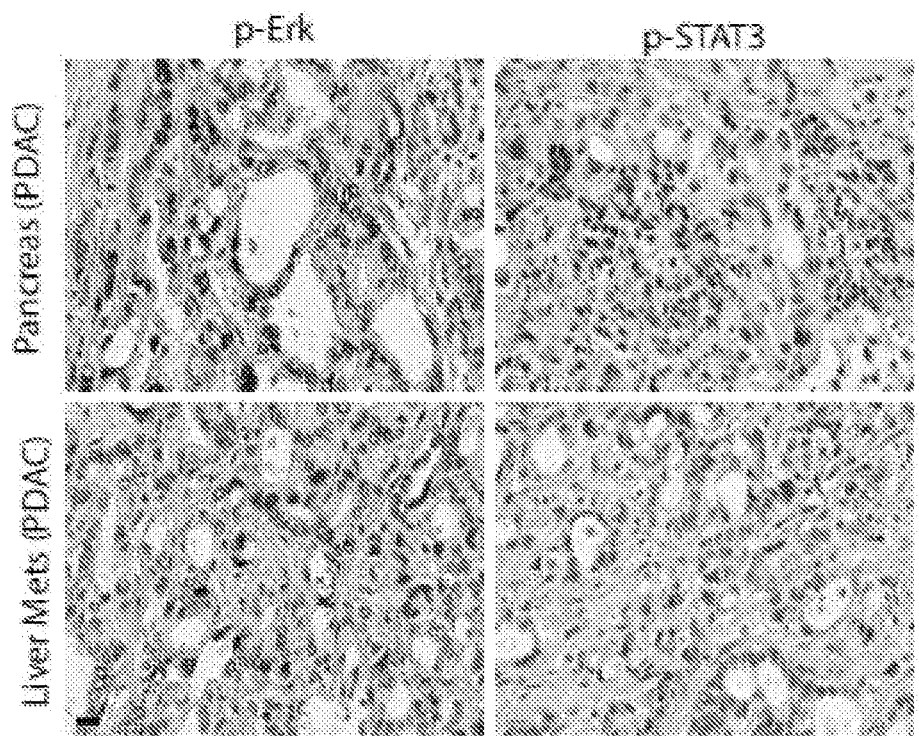
FIG. 25 depicts analysis of p-Erk and p-STAT3 in pancreatic tumors and metastases from PDAC patient samples: Representative primary tumor and liver sections stained for p-Erk and p-STAT3 in PDAC patient samples. Scale bar: 20 μm.
Figure 26:
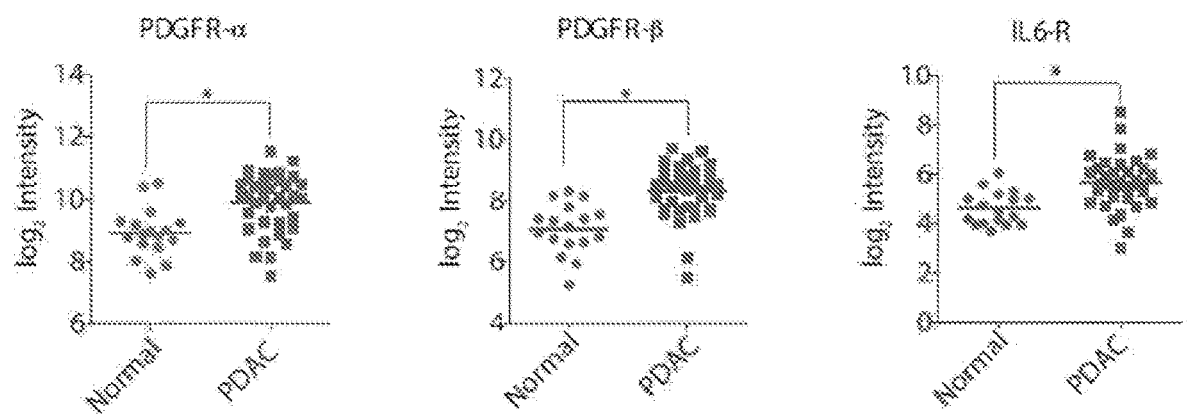
FIG. 26 depicts analysis of p-Erk and p-STAT3 in pancreatic tumors and metastases from PDAC patient samples: Microarray analysis of expression of PDGFR and IL-6R in PDAC patient tumor samples.

Example 5: Differential Activation of Erk and STAT3 in Liver Metastases in PDAC Patients To examine the potential clinical relevance of these findings, we performed IHC analysis of 76 human PDAC tissue samples and 4 liver metastases for p-Erk and p-STAT3. Erk was activated in 13% of PDAC tissues samples (10/76), mostly in patients with stage I and II malignancies, STAT3 activation was observed in 26% of samples (20/76), and 6.5% of samples (5/76) exhibited both activated Erk and STAT3, mainly in stage I malignancy (FIGS. 24 & 25). Furthermore, 50% of the liver metastases demonstrated Erk activation (2/4), and STAT3 activation was seen in 25% of the samples (1/4) (FIGS. 24 & 25). In addition, gene expression analysis further revealed that PDAC tumors from human patients expressed increased levels of the RTKs PDGFRα, PDGFRβ, as well as IL6-R, relative to normal tissue (FIG. 26, Table 3).

TABLE 3

Gene Expression Analysis Data

| PDGFRα Log2 (Probe Intensity) | Gene_id | Probeset | Sample Type | Tissue Group | Tissue Diagnosis | Tissue Diagnosis Group |
|---|---|---|---|---|---|---|
| 8.794943 | GeneID: 5156 | 203131_at | Tissue | Pancreas | Normal pancreas | Normal |
| 9.279793 | GeneID: 5156 | 203131_at | Tissue | Pancreas | Normal pancreas | Normal |
| 9.227017 | GeneID: 5156 | 203131_at | Tissue | Pancreas | Normal pancreas | Normal |
| 8.889409 | GeneID: 5156 | 203131_at | Tissue | Pancreas | Normal pancreas | Normal |
| 8.958932 | GeneID: 5156 | 203131_at | Tissue | Pancreas | Normal pancreas | Normal |
| 8.993035 | GeneID: 5156 | 203131_at | Tissue | Pancreas | Normal pancreas | Normal |
| 10.39963 | GeneID: 5156 | 203131_at | Tissue | Pancreas | Normal pancreas | Normal |
| 10.50218 | GeneID: 5156 | 203131_at | Tissue | Pancreas | Normal pancreas | Normal |
| 9.184865 | GeneID: 5156 | 203131_at | Tissue | Pancreas | Normal pancreas | Normal |
| 8.808953 | GeneID: 5156 | 203131_at | Tissue | Pancreas | Normal pancreas | Normal |
| 7.621978 | GeneID: 5156 | 203131_at | Tissue | Pancreas | Normal pancreas | Normal |
| 8.470824 | GeneID: 5156 | 203131_at | Tissue | Pancreas | Normal pancreas | Normal |
| 8.586969 | GeneID: 5156 | 203131_at | Tissue | Pancreas | Normal pancreas | Normal |
| 7.883403 | GeneID: 5156 | 203131_at | Tissue | Pancreas | Normal pancreas | Normal |
| 8.024827 | GeneID: 5156 | 203131_at | Tissue | Pancreas | Normal pancreas | Normal |
| 8.687401 | GeneID: 5156 | 203131_at | Tissue | Pancreas | Normal pancreas | Normal |
| 9.584143 | GeneID: 5156 | 203131_at | Tissue | Pancreas | Normal pancreas | Normal |
| 9.421285 | GeneID: 5156 | 203131_at | Tissue | Pancreas | Adenocarcinoma | Cancer |
| 10.09945 | GeneID: 5156 | 203131_at | Tissue | Pancreas | Adenocarcinoma | Cancer |
| 10.1031 | GeneID: 5156 | 203131_at | Tissue | Pancreas | Adenocarcinoma | Cancer |
| 10.92539 | GeneID: 5156 | 203131_at | Tissue | Pancreas | Adenocarcinoma | Cancer |
| 11.56405 | GeneID: 5156 | 203131_at | Tissue | Pancreas | Adenocarcinoma | Cancer |
| 8.581601 | GeneID: 5156 | 203131_at | Tissue | Pancreas | Adenocarcinoma | Cancer |
| 10.75649 | GeneID: 5156 | 203131_at | Tissue | Pancreas | Adenocarcinoma | Cancer |
| 10.77969 | GeneID: 5156 | 203131_at | Tissue | Pancreas | Adenocarcinoma | Cancer |
| 10.46082 | GeneID: 5156 | 203131_at | Tissue | Pancreas | Adenocarcinoma | Cancer |
| 9.26923 | GeneID: 5156 | 203131_at | Tissue | Pancreas | Adenocarcinoma | Cancer |
| 11.24358 | GeneID: 5156 | 203131_at | Tissue | Pancreas | Adenocarcinoma | Cancer |
| 10.43788 | GeneID: 5156 | 203131_at | Tissue | Pancreas | Adenocarcinoma | Cancer |
| 10.45637 | GeneID: 5156 | 203131_at | Tissue | Pancreas | Adenocarcinoma | Cancer |
| 10.82082 | GeneID: 5156 | 203131_at | Tissue | Pancreas | Adenocarcinoma | Cancer |
| 10.61548 | GeneID: 5156 | 203131_at | Tissue | Pancreas | Adenocarcinoma | Cancer |
| 10.05359 | GeneID: 5156 | 203131_at | Tissue | Pancreas | Adenocarcinoma | Cancer |
| 10.88377 | GeneID: 5156 | 203131_at | Tissue | Pancreas | Adenocarcinoma | Cancer |
| 10.03931 | GeneID: 5156 | 203131_at | Tissue | Pancreas | Adenocarcinoma | Cancer |
| 10.43891 | GeneID: 5156 | 203131_at | Tissue | Pancreas | Adenocarcinoma | Cancer |
| 9.878045 | GeneID: 5156 | 203131_at | Tissue | Pancreas | Adenocarcinoma | Cancer |
| 10.63892 | GeneID: 5156 | 203131_at | Tissue | Pancreas | Adenocarcinoma | Cancer |
| 9.042114 | GeneID: 5156 | 203131_at | Tissue | Pancreas | Adenocarcinoma | Cancer |
| 10.11472 | GeneID: 5156 | 203131_at | Tissue | Pancreas | Adenocarcinoma | Cancer |
| 9.814941 | GeneID: 5156 | 203131_at | Tissue | Pancreas | Adenocarcinoma | Cancer |
| 10.32152 | GeneID: 5156 | 203131_at | Tissue | Pancreas | Adenocarcinoma | Cancer |
| 9.091601 | GeneID: 5156 | 203131_at | Tissue | Pancreas | Adenocarcinoma | Cancer |
| 9.222542 | GeneID: 5156 | 203131_at | Tissue | Pancreas | Adenocarcinoma | Cancer |
| 10.70983 | GeneID: 5156 | 203131_at | Tissue | Pancreas | Adenocarcinoma | Cancer |
| 8.636107 | GeneID: 5156 | 203131_at | Tissue | Pancreas | Adenocarcinoma | Cancer |
| 10.39972 | GeneID: 5156 | 203131_at | Tissue | Pancreas | Adenocarcinoma | Cancer |
| 7.513814 | GeneID: 5156 | 203131_at | Tissue | Pancreas | Adenocarcinoma | Cancer |
| 9.729338 | GeneID: 5156 | 203131_at | Tissue | Pancreas | Adenocarcinoma | Cancer |
| 9.566706 | GeneID: 5156 | 203131_at | Tissue | Pancreas | Adenocarcinoma | Cancer |
| 8.181587 | GeneID: 5156 | 203131_at | Tissue | Pancreas | Adenocarcinoma | Cancer |
| 8.138516 | GeneID: 5156 | 203131_at | Tissue | Pancreas | Adenocarcinoma | Cancer |
| 8.845604 | GeneID: 5156 | 203131_at | Tissue | Pancreas | Adenocarcinoma | Cancer |
| 10.00465 | GeneID: 5156 | 203131_at | Tissue | Pancreas | Adenocarcinoma | Cancer |
| 7.556889 | GeneID: 5159 | 202273_at | Tissue | Pancreas | Normal pancreas | Normal |
| 5.260128 | GeneID: 5159 | 202273_at | Tissue | Pancreas | Normal pancreas | Normal |
| 7.409171 | GeneID: 5159 | 202273_at | Tissue | Pancreas | Normal pancreas | Normal |
| 6.764048 | GeneID: 5159 | 202273_at | Tissue | Pancreas | Normal pancreas | Normal |
| 7.422604 | GeneID: 5159 | 202273_at | Tissue | Pancreas | Normal pancreas | Normal |
| 7.341148 | GeneID: 5159 | 202273_at | Tissue | Pancreas | Normal pancreas | Normal |
| 8.150971 | GeneID: 5159 | 202273_at | Tissue | Pancreas | Normal pancreas | Normal |
| 8.320784 | GeneID: 5159 | 202273_at | Tissue | Pancreas | Normal pancreas | Normal |

TABLE 3-continued

Gene Expression Analysis Data

| PDGFRα Log2 (Probe Intensity) | Gene_id | Probeset | Sample Type | Tissue Group | Tissue Diagnosis | Tissue Diagnosis Group |
|---|---|---|---|---|---|---|
| 7.788783 | GeneID: 5159 | 202273_at | Tissue | Pancreas | Normal pancreas | Normal |
| 7.156454 | GeneID: 5159 | 202273_at | Tissue | Pancreas | Normal pancreas | Normal |
| 6.155598 | GeneID: 5159 | 202273_at | Tissue | Pancreas | Normal pancreas | Normal |
| 6.59976 | GeneID: 5159 | 202273_at | Tissue | Pancreas | Normal pancreas | Normal |
| 6.819837 | GeneID: 5159 | 202273_at | Tissue | Pancreas | Normal pancreas | Normal |
| 5.95445 | GeneID: 5159 | 202273_at | Tissue | Pancreas | Normal pancreas | Normal |
| 6.956264 | GeneID: 5159 | 202273_at | Tissue | Pancreas | Normal pancreas | Normal |
| 6.647721 | GeneID: 5159 | 202273_at | Tissue | Pancreas | Normal pancreas | Normal |
| 8.160778 | GeneID: 5159 | 202273_at | Tissue | Pancreas | Normal pancreas | Normal |
| 7.726896 | GeneID: 5159 | 202273_at | Tissue | Pancreas | Adenocarcinoma | Cancer |
| 7.46055 | GeneID: 5159 | 202273_at | Tissue | Pancreas | Adenocarcinoma | Cancer |
| 8.502994 | GeneID: 5159 | 202273_at | Tissue | Pancreas | Adenocarcinoma | Cancer |
| 9.322616 | GeneID: 5159 | 202273_at | Tissue | Pancreas | Adenocarcinoma | Cancer |
| 9.374715 | GeneID: 5159 | 202273_at | Tissue | Pancreas | Adenocarcinoma | Cancer |
| 7.797891 | GeneID: 5159 | 202273_at | Tissue | Pancreas | Adenocarcinoma | Cancer |
| 8.995366 | GeneID: 5159 | 202273_at | Tissue | Pancreas | Adenocarcinoma | Cancer |
| 9.644044 | GeneID: 5159 | 202273_at | Tissue | Pancreas | Adenocarcinoma | Cancer |
| 8.891796 | GeneID: 5159 | 202273_at | Tissue | Pancreas | Adenocarcinoma | Cancer |
| 8.50103 | GeneID: 5159 | 202273_at | Tissue | Pancreas | Adenocarcinoma | Cancer |
| 9.229039 | GeneID: 5159 | 202273_at | Tissue | Pancreas | Adenocarcinoma | Cancer |
| 8.961214 | GeneID: 5159 | 202273_at | Tissue | Pancreas | Adenocarcinoma | Cancer |
| 9.122539 | GeneID: 5159 | 202273_at | Tissue | Pancreas | Adenocarcinoma | Cancer |
| 8.841867 | GeneID: 5159 | 202273_at | Tissue | Pancreas | Adenocarcinoma | Cancer |
| 8.608741 | GeneID: 5159 | 202273_at | Tissue | Pancreas | Adenocarcinoma | Cancer |
| 8.56492 | GeneID: 5159 | 202273_at | Tissue | Pancreas | Adenocarcinoma | Cancer |
| 8.615495 | GeneID: 5159 | 202273_at | Tissue | Pancreas | Adenocarcinoma | Cancer |
| 8.229863 | GeneID: 5159 | 202273_at | Tissue | Pancreas | Adenocarcinoma | Cancer |
| 8.591798 | GeneID: 5159 | 202273_at | Tissue | Pancreas | Adenocarcinoma | Cancer |
| 9.707525 | GeneID: 5159 | 202273_at | Tissue | Pancreas | Adenocarcinoma | Cancer |
| 8.560279 | GeneID: 5159 | 202273_at | Tissue | Pancreas | Adenocarcinoma | Cancer |
| 7.758313 | GeneID: 5159 | 202273_at | Tissue | Pancreas | Adenocarcinoma | Cancer |
| 7.691537 | GeneID: 5159 | 202273_at | Tissue | Pancreas | Adenocarcinoma | Cancer |
| 8.339635 | GeneID: 5159 | 202273_at | Tissue | Pancreas | Adenocarcinoma | Cancer |
| 8.350952 | GeneID: 5159 | 202273_at | Tissue | Pancreas | Adenocarcinoma | Cancer |
| 7.564781 | GeneID: 5159 | 202273_at | Tissue | Pancreas | Adenocarcinoma | Cancer |
| 7.276369 | GeneID: 5159 | 202273_at | Tissue | Pancreas | Adenocarcinoma | Cancer |
| 8.803938 | GeneID: 5159 | 202273_at | Tissue | Pancreas | Adenocarcinoma | Cancer |
| 5.474688 | GeneID: 5159 | 202273_at | Tissue | Pancreas | Adenocarcinoma | Cancer |
| 7.747431 | GeneID: 5159 | 202273_at | Tissue | Pancreas | Adenocarcinoma | Cancer |
| 6.137455 | GeneID: 5159 | 202273_at | Tissue | Pancreas | Adenocarcinoma | Cancer |
| 8.855201 | GeneID: 5159 | 202273_at | Tissue | Pancreas | Adenocarcinoma | Cancer |
| 8.112997 | GeneID: 5159 | 202273_at | Tissue | Pancreas | Adenocarcinoma | Cancer |
| 7.976575 | GeneID: 5159 | 202273_at | Tissue | Pancreas | Adenocarcinoma | Cancer |
| 8.131375 | GeneID: 5159 | 202273_at | Tissue | Pancreas | Adenocarcinoma | Cancer |
| 7.670179 | GeneID: 5159 | 202273_at | Tissue | Pancreas | Adenocarcinoma | Cancer |
| 8.541986 | GeneID: 5159 | 202273_at | Tissue | Pancreas | Adenocarcinoma | Cancer |
| 5.553321 | GeneID: 3570 | 205945_at | Tissue | Pancreas | Normal pancreas | Normal |
| 4.120181 | GeneID: 3570 | 205945_at | Tissue | Pancreas | Normal pancreas | Normal |
| 3.985927 | GeneID: 3570 | 205945_at | Tissue | Pancreas | Normal pancreas | Normal |
| 4.267829 | GeneID: 3570 | 205945_at | Tissue | Pancreas | Normal pancreas | Normal |
| 4.991783 | GeneID: 3570 | 205945_at | Tissue | Pancreas | Normal pancreas | Normal |
| 3.940651 | GeneID: 3570 | 205945_at | Tissue | Pancreas | Normal pancreas | Normal |
| 4.715778 | GeneID: 3570 | 205945_at | Tissue | Pancreas | Normal pancreas | Normal |
| 6.031536 | GeneID: 3570 | 205945_at | Tissue | Pancreas | Normal pancreas | Normal |
| 5.290729 | GeneID: 3570 | 205945_at | Tissue | Pancreas | Normal pancreas | Normal |
| 4.473181 | GeneID: 3570 | 205945_at | Tissue | Pancreas | Normal pancreas | Normal |
| 4.173704 | GeneID: 3570 | 205945_at | Tissue | Pancreas | Normal pancreas | Normal |
| 3.933525 | GeneID: 3570 | 205945_at | Tissue | Pancreas | Normal pancreas | Normal |
| 5.157238 | GeneID: 3570 | 205945_at | Tissue | Pancreas | Normal pancreas | Normal |
| 4.945232 | GeneID: 3570 | 205945_at | Tissue | Pancreas | Normal pancreas | Normal |
| 3.684718 | GeneID: 3570 | 205945_at | Tissue | Pancreas | Normal pancreas | Normal |
| 3.924458 | GeneID: 3570 | 205945_at | Tissue | Pancreas | Normal pancreas | Normal |
| 4.979816 | GeneID: 3570 | 205945_at | Tissue | Pancreas | Normal pancreas | Normal |
| 4.631535 | GeneID: 3570 | 205945_at | Tissue | Pancreas | Adenocarcinoma | Cancer |
| 5.525271 | GeneID: 3570 | 205945_at | Tissue | Pancreas | Adenocarcinoma | Cancer |
| 5.343428 | GeneID: 3570 | 205945_at | Tissue | Pancreas | Adenocarcinoma | Cancer |
| 5.365025 | GeneID: 3570 | 205945_at | Tissue | Pancreas | Adenocarcinoma | Cancer |
| 6.389725 | GeneID: 3570 | 205945_at | Tissue | Pancreas | Adenocarcinoma | Cancer |
| 6.064351 | GeneID: 3570 | 205945_at | Tissue | Pancreas | Adenocarcinoma | Cancer |
| 4.978231 | GeneID: 3570 | 205945_at | Tissue | Pancreas | Adenocarcinoma | Cancer |
| 5.265962 | GeneID: 3570 | 205945_at | Tissue | Pancreas | Adenocarcinoma | Cancer |
| 4.801198 | GeneID: 3570 | 205945_at | Tissue | Pancreas | Adenocarcinoma | Cancer |
| 5.478386 | GeneID: 3570 | 205945_at | Tissue | Pancreas | Adenocarcinoma | Cancer |
| 6.81306 | GeneID: 3570 | 205945_at | Tissue | Pancreas | Adenocarcinoma | Cancer |

TABLE 3-continued

Gene Expression Analysis Data

| PDGFRα Log2 (Probe Intensity) | Gene_id | Probeset | Sample Type | Tissue Group | Tissue Diagnosis | Tissue Diagnosis Group |
|---|---|---|---|---|---|---|
| 6.182141 | GeneID: 3570 | 205945_at | Tissue | Pancreas | Adenocarcinoma | Cancer |
| 4.817283 | GeneID: 3570 | 205945_at | Tissue | Pancreas | Adenocarcinoma | Cancer |
| 5.62403 | GeneID: 3570 | 205945_at | Tissue | Pancreas | Adenocarcinoma | Cancer |
| 5.553858 | GeneID: 3570 | 205945_at | Tissue | Pancreas | Adenocarcinoma | Cancer |
| 6.210491 | GeneID: 3570 | 205945_at | Tissue | Pancreas | Adenocarcinoma | Cancer |
| 5.7035 | GeneID: 3570 | 205945_at | Tissue | Pancreas | Adenocarcinoma | Cancer |
| 5.551391 | GeneID: 3570 | 205945_at | Tissue | Pancreas | Adenocarcinoma | Cancer |
| 7.040005 | GeneID: 3570 | 205945_at | Tissue | Pancreas | Adenocarcinoma | Cancer |
| 4.326793 | GeneID: 3570 | 205945_at | Tissue | Pancreas | Adenocarcinoma | Cancer |
| 6.092874 | GeneID: 3570 | 205945_at | Tissue | Pancreas | Adenocarcinoma | Cancer |
| 5.327012 | GeneID: 3570 | 205945_at | Tissue | Pancreas | Adenocarcinoma | Cancer |
| 4.138626 | GeneID: 3570 | 205945_at | Tissue | Pancreas | Adenocarcinoma | Cancer |
| 5.365025 | GeneID: 3570 | 205945_at | Tissue | Pancreas | Adenocarcinoma | Cancer |
| 5.924268 | GeneID: 3570 | 205945_at | Tissue | Pancreas | Adenocarcinoma | Cancer |
| 6.036687 | GeneID: 3570 | 205945_at | Tissue | Pancreas | Adenocarcinoma | Cancer |
| 5.053131 | GeneID: 3570 | 205945_at | Tissue | Pancreas | Adenocarcinoma | Cancer |
| 6.451621 | GeneID: 3570 | 205945_at | Tissue | Pancreas | Adenocarcinoma | Cancer |
| 2.964388 | GeneID: 3570 | 205945_at | Tissue | Pancreas | Adenocarcinoma | Cancer |
| 4.699464 | GeneID: 3570 | 205945_at | Tissue | Pancreas | Adenocarcinoma | Cancer |
| 7.824091 | GeneID: 3570 | 205945_at | Tissue | Pancreas | Adenocarcinoma | Cancer |
| 6.540267 | GeneID: 3570 | 205945_at | Tissue | Pancreas | Adenocarcinoma | Cancer |
| 3.617126 | GeneID: 3570 | 205945_at | Tissue | Pancreas | Adenocarcinoma | Cancer |
| 5.350239 | GeneID: 3570 | 205945_at | Tissue | Pancreas | Adenocarcinoma | Cancer |
| 8.541102 | GeneID: 3570 | 205945_at | Tissue | Pancreas | Adenocarcinoma | Cancer |
| 5.96024 | GeneID: 3570 | 205945_at | Tissue | Pancreas | Adenocarcinoma | Cancer |
| 6.767234 | GeneID: 3570 | 205945_at | Tissue | Pancreas | Adenocarcinoma | Cancer |

The data in Table 3 suggest that PDAC tumors can be driven by PDGFR, IL-6 and STAT3 signaling, and that these pathways may limit the response to MEK pathway inhibition. These findings also indicate that the MEK pathway may play an important role in the survival of tumor cells in liver metastases that do not switch to a STAT3-mediated survival cascade upon metastasis in human pancreatic cancer patients.

All technical and scientific terms used herein have the same meaning. Efforts have been made to ensure accuracy with respect to numbers used (e.g. amounts, temperature, etc.) but some experimental errors and deviations should be accounted for.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of treating pancreatic cancer, in a subject in need thereof, the method comprising:
administering to said subject a therapeutically effective amount of a combination of active agents, wherein said combination comprises or a pharmaceutically acceptable salt thereof, and ponatinib or a pharmaceutically acceptable salt thereof.

2. The method of claim 1, wherein said pancreatic cancer is endocrine.

3. The method of claim 1, wherein said pancreatic cancer is exocrine.

4. The method of claim 3, wherein said pancreatic cancer is adenocarcinomas, acinar cell carcinomas, adenosquamous carcinomas, colloid carcinomas, undifferentiated carcinomas with osteoclast-like giant cells, hepatoid carcinomas, intraductal papillary-mucinous neoplasms, mucinous cystic neoplasms, pancreatoblastomas, serous cystadenomas, signet ring cell carcinomas, solid and pseuodpapillary tumors, pancreatic ductal carcinomas, or undifferentiated carcinomas.

5. The method of claim 4, wherein said pancreatic cancer is pancreatic ductal adenocarcinoma.

6. The method of claim 1, wherein said combination is synergistic.

7. The method of claim 1, wherein said active agents are administered sequentially.

8. The method of claim 1, wherein said active agents are administered concomitantly.

9. The method of claim 1, wherein cobimetinib and ponatinib are administered as a combined formulation.

10. The method of claim 1, wherein cobimetinib is administered in an amount of from about 45 mg to about 75 mg and ponatinib is administered in an amount of from about 30 mg to about 60 mg.

11. The method of claim 10, wherein said amounts are administered once daily.

12. A pharmaceutical composition comprising a therapeutically effective amount of a combination of cobimetinib or a pharmaceutically acceptable salt thereof, and ponatinib or a pharmaceutically acceptable salt thereof, and a pharmaceutically acceptable excipient.

13. The composition of claim 12, wherein cobimetinib, or a pharmaceutically acceptable salt thereof, is present in an amount of from about 45 mg to about 75 mg and ponatinib, or a pharmaceutically acceptable salt thereof, is present in an amount of from about 30 mg to about 60 mg.

14. A kit comprising a therapeutically effective amount of a combination of cobimetinib or a pharmaceutically acceptable salt thereof, and ponatinib or a pharmaceutically acceptable salt thereof, a container, and a package insert or label.

15. The method of claim 1, wherein cobimetinib is administered at a dose between about 1 mg/kg and about 50 mg/kg and ponatinib is administered at a dose between about 1 mg/kg and about 50 mg/kg.

16. The method of claim 15, wherein cobimetinib is administered at a dose between about 1 mg/kg and about 10 mg/kg and ponatinib is administered at a dose between about 10 mg/kg and about 40 mg/kg.

* * * * *

UNITED STATES PATENT AND TRADEMARK OFFICE
CERTIFICATE OF CORRECTION

| | | |
|---|---|---|
| PATENT NO. | : 10,933,058 B2 | Page 1 of 1 |
| APPLICATION NO. | : 16/283203 | |
| DATED | : March 2, 2021 | |
| INVENTOR(S) | : Jeff Settleman et al. | |

It is certified that error appears in the above-identified patent and that said Letters Patent is hereby corrected as shown below:

In the Claims

Claim 1, Column 41, Line 21, "combination comprises or" should read --combination comprises cobimetinib or--.

Signed and Sealed this
Twenty-sixth Day of April, 2022

Katherine Kelly Vidal
*Director of the United States Patent and Trademark Office*